(12) United States Patent
Wischik et al.

(10) Patent No.: US 9,211,294 B2
(45) Date of Patent: Dec. 15, 2015

(54) PHENOTHIAZINE COMPOUNDS FOR TREATING MILD COGNITIVE IMPAIRMENT

(75) Inventors: Claude Michel Wischik, Aberdeen (GB); Dominic Venay Harbaran, Aberdeen (GB); Gernot Riedel, Aberdeen (GB); Serena Deiana, Aberdeen (GB); Elizabeth Anne Goatman, Aberdeen (GB); Damon Jude Wischik, London (GB); Alison Dorothy Murray, Aberdeen (GB); Roger Todd Staff, Aberdeen (GB)

(73) Assignee: WisTa Laboratories Ltd., Singapore (SG)

( * ) Notice: Subject to any disclaimer, the term of this patent is extended or adjusted under 35 U.S.C. 154(b) by 685 days.

(21) Appl. No.: 12/665,608

(22) PCT Filed: Jun. 17, 2008

(86) PCT No.: PCT/GB2008/002066
§ 371 (c)(1),
(2), (4) Date: Dec. 18, 2009

(87) PCT Pub. No.: WO2008/155533
PCT Pub. Date: Dec. 24, 2008

(65) Prior Publication Data
US 2010/0184752 A1     Jul. 22, 2010

Related U.S. Application Data

(60) Provisional application No. 60/945,006, filed on Jun. 19, 2007.

(51) Int. Cl.
*A61K 31/5415*     (2006.01)
(52) U.S. Cl.
CPC .................................. *A61K 31/5415* (2013.01)
(58) Field of Classification Search
CPC .................................................. A61K 31/5415
USPC ......................................... 514/224.8; 546/35
See application file for complete search history.

(56) References Cited

U.S. PATENT DOCUMENTS

| 7,888,350 | B2 | 2/2011 | Wischik et al. | |
|---|---|---|---|---|
| 2006/0287523 | A1* | 12/2006 | Wischik et al. | 544/37 |
| 2011/0118242 | A1 | 5/2011 | Wischik et al. | |

FOREIGN PATENT DOCUMENTS

| JP | 2004-524831 | | 8/2004 |
|---|---|---|---|
| WO | WO 96/30766 | | 10/1996 |
| WO | WO 0203972 A2 | * | 1/2002 |
| WO | WO 02/055720 A2 | | 7/2002 |
| WO | WO 2004087160 A1 | * | 10/2004 |
| WO | WO 2006/032879 A2 | | 3/2006 |
| WO | WO 2006091728 A2 | * | 8/2006 |
| WO | WO 2007/110627 A2 | | 10/2007 |
| WO | WO 2007/110629 A1 | | 10/2007 |
| WO | WO 2007/110630 A1 | | 10/2007 |
| WO | WO 2008/007074 A2 | | 1/2008 |

OTHER PUBLICATIONS

Small et. al., The New England Journal of Medicine, 2006, Massachusetts Medical Society, vol. 355, pp. 2652-2663.*
Salloway et. al., Neurology, 2004, AAN Enterprises, vol. 63, pp. 651-657.*
Vippagunta et. al., Advanced Drug Delivery Reviews, 2001, Elsevier, vol. 48, pp. 3-26.*
Suzuki et. al., Journal of Medicinal Chemistry, 1993, American Chemical Society, vol. 36, pp. 2508-2518.*
Wishka et. al., Journal of Medicinal Chemistry, 2006, American Chemical Society, vol. 49, pp. 4425-4436.*
Gould, International Journal of Pharmaceutics, 1986, Elsevier, vol. 33, issues 1-3, pp. 201-217.*
International Search Report for PCT/GB2008/002066; mailed Dec. 12, 2006. (4 pages).
Callaway et al., "Methylene Blue Restores Spatial Memory Retention Impaired by an Inhibitor of Cytochrome Oxidase in Rats," *Neuroscience Letters*, 2002, vol. 332, pp. 83-86.
Callaway et al., "Methylene Blue Improves Brain Oxidative Metabolism and Memory Retention in Rats," *Pharmacology, Biochemistry and Behavior*, 2004, vol. 77, pp. 175-181.
Dickey et al., "Pharmacologic Reductions of Total tau Levels; Implications for the Role of Microtubule Dynamics in Regulating tau Expression," *Molecular Neurodegeneration*, 2006, vol. 1, p. 9. 1-9.
Riha et al., "Memory Facilitation by Methylene Blue: Dose-dependent Effect on Behavior and Brain Oxygen Consumption," *European Journal of Pharmacology*, 2005, vol. 511, pp. 151-158.
Wrubel et al., "The Brain Metabolic Enhancer Methylene Blue Improves Discrimination Learning in Rats," *Pharmacology, Biochemistry and Behavior*, 2007, vol. 86, pp. 712-717.
International Preliminary Report on Patentability for PCT/GB2008/002066; mailed Jan. 7, 2010. (9 pages).
Julio C. Rojas et al., Methylene Blue Provides Behavioral and Metabolic Neuroprotection Against Optic Neuropathy, Neurotox Res (2009) 15:260-273.
M. Contineanu et al., Radiolysis of Methylene Blue Studied by ESR, Radiochem. Radioanal. Letters (1983) 57 /1/ 9-22.
H.D.K. Drew et al., Derivatives of Methylene-blue, Journal of the Chemical Society (1933) pp. 248-253.
W.H. Tayor et al., An X-Ray Examination of Methylene Blue, Z. Krist., 91 (1935) pp. 451-465.
J.O. Warwicker, The Crystal Structure of Methylene-blue, J. Chem. Soc. (1955) p. 2531.
G.F. Davidson, The Determination of Methylene Blue, J. Textile Institute 38 (1947) pp. T408-T418.

(Continued)

*Primary Examiner* — Sarah Pihonak
(74) *Attorney, Agent, or Firm* — Foley & Lardner LLP

(57) ABSTRACT

The present invention relates generally to methods and materials based on diaminophenothiazines for use in the treatment of Mild Cognitive Impairment (MCI).

14 Claims, 21 Drawing Sheets

(56) References Cited

OTHER PUBLICATIONS

Figure 1:
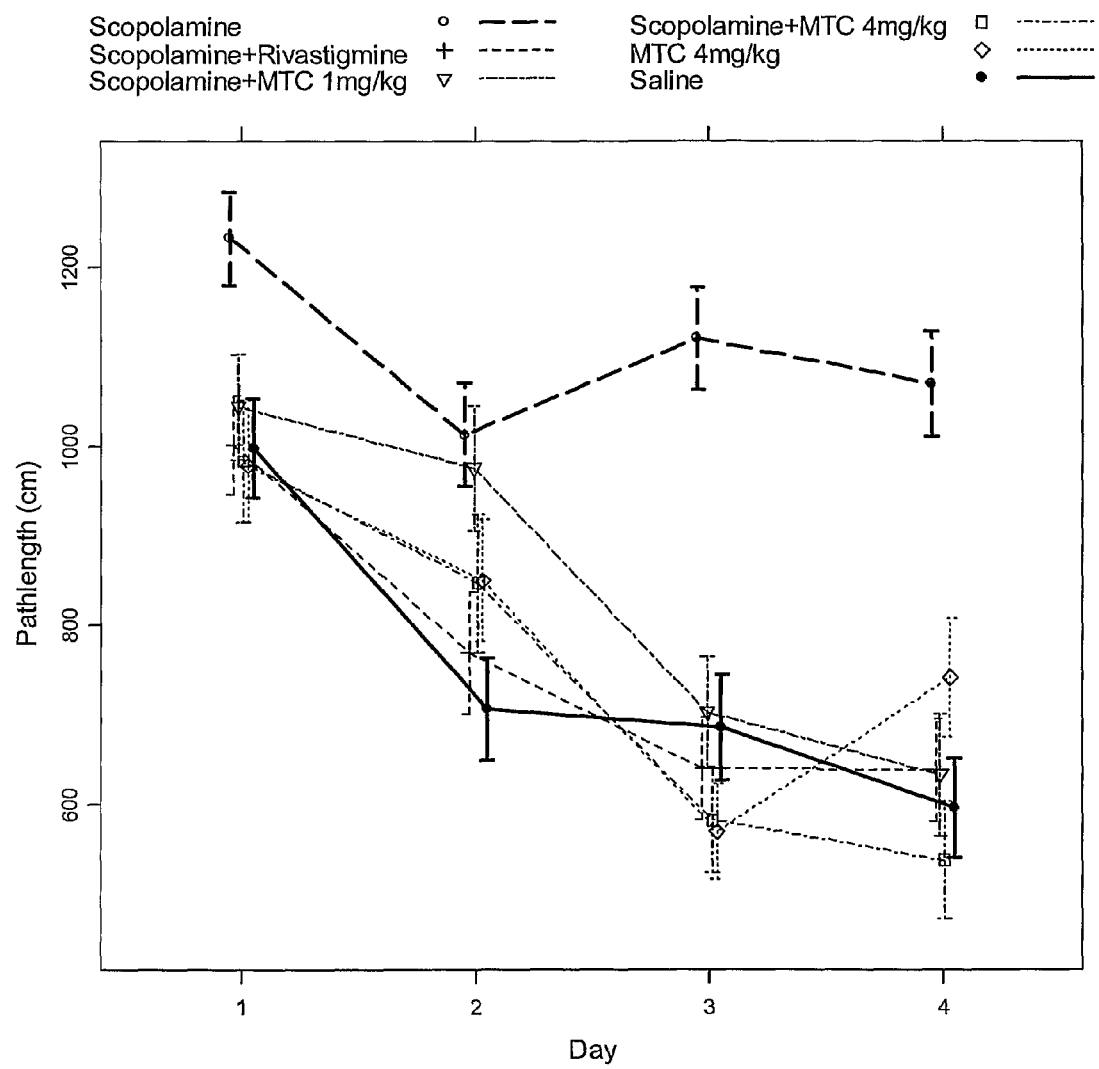

H.E. Marrr III et al., The Crystal Structure of Methylene Blue Pentahydrate, Acta Cryst. B29 (1973) pp. 847-853.

The Office Action (Notification of Reasons for Rejection) received in the related Japanese patent application No. JP 2010-512761, dated May 21, 2013.

Callaway, et al., "Methylene blue improves brain oxidative metabolism and memory retention in rats", *Pharm. Biochem. Behav.*, 2004, vol. 77, No. 1, p. 175-181.

Riha, et al., "Memory facilitation by methylene blue: Dose-dependent effect on behavior and brain oxygen consumption", *Eur. J. Pharma.*, 2005, vol. 511, No. 2-3, pp. 151-158.

Wrubel, et al., "The brain metabolic enhancer methylene blue improves discrimination learning in rats", *Pharm. Biochem. Behav.*, 2007, vol. 86, No. 4, pp. 712-717.

Takashi Asada, Weekly Story, (Isshu Ichiwa), "Views on Mild Cognitive Impairment" (Keido ninnchi shougai no kangaekata), *Japanese medical journal* (Nihon Iji Shinpo), 2003, No. 4153, p. 1010.

Shunichiro Shinagawa and another, Feather Story, Early diagnosis and treatment of dementia and comprehensive functional evaluation—the present state and roles of the outpatient clinics for forgetfulness (*Chihou no souki sinndann/chiryouto sougouteki kinouhyoka-monowasure gairai no gennjyo to yukuwari*)—IV. Topics "1. MCI: Mild Cognitive Impairment", *Prog. Med.*, Oct. 2004, vol. 24, No. 10, p. 2485-2488.

Satoshi Takehashi and another, Special Features, Dotage/Dementia-Care and Prevention "Is Mild Cognitive Impairment the beginning of dementia?" (Boke/Chinhou-Sinnryou to Yobou "Keindoninnchi shougai (mild cognitive impairment) wa chihou no hajimarika"), *The Japanese Journal of clinical and experimental medicine* (*Rinsho to Kenkyu*), Jun. 2002, vol. 79., No. 6. pp. 919-922.

Hiroyuki Arai, Alzheimer's disease-[I] Clinical Topics "3. Early diagnosis of Mild Cognitive Impairment and dementia (*Alzheimer byou-[I] Rinsho no wadai 3. keindoninnchi shougai to chinhou no souki sindan*"), Syllabus of the 125th symposium of the Japanese Associate of Medical Science (*Dai 125 kai nihon igakugakkai symposium kirokushu*), 2004, p. 21-28.

* cited by examiner

Saline 2-3 months
 MTC 1 mg/kg 2-3 months
 Saline 13 months
 MTC 1 mg/kg 13 months

PHENOTHIAZINE COMPOUNDS FOR TREATING MILD COGNITIVE IMPAIRMENT

CROSS-REFERENCE TO RELATED PATENT APPLICATIONS

The application is a National Phase Entry of PCT Application No. PCT/GB2008/002066 filed Jun. 17, 2008, which claims priority to U.S. Provisional Application No. 60/945,006 filed Jun. 19, 2007, incorporated herein by reference in its entirety.

TECHNICAL FIELD

The present invention relates generally to methods and materials for use in the treatment of Mild Cognitive Impairment (MCI).

BACKGROUND ART

Mild Cognitive Impairment (MCI) is a subset of a broader clinical entity termed "Cognitive Impairment Non-Dementia", or CIND.

There are many potential causes of CIND including: depression, alcohol/drug use, psychiatric disease, delirium, mental retardation, vascular causes, Parkinson's disease, epilepsy, multiple sclerosis, social factors, and sensory impairment.

MCI subjects are not demented, but are at risk of developing dementia such as Alzheimer's Disease (AD)(Larieu, S. et al. (2002) Incidence and outcome of mild cognitive impairment in a population-based prospective cohort. Neurology, 59: 1594-1599; Bennett, D. A. et al. (2002) Natural history of mild cognitive impairment in older persons. Neurology, 59: 198-205. In fact it has been estimated that 10% of those with MCI convert to AD (Bruscoli and Lovestone (2004), Is MCI really just early dementia? A systematic review of conversion studies. Int Psychogeriat. 16:2, 129-140).

MCI has been recognised by the FDA as a valid treatment target (FDA (2001), fda.gov/ohrms/dockets/ac/01/slides/3724s1_6_grundman/).

This has led to the emergence of a number of clinical trials for MCI (for example That et al., (2005), A randomized double-blind study of Rofecoxib in patients with Mild Cognitive Impairment, Neuropsychopharm, 30: 1204-1215).

DISCLOSURE OF THE INVENTION

It can be seen that the provision of alternative treatment modalities for MCI for the purpose of relief of MCI or the symptoms of MCI would provide a contribution to the art.

It is has now been unexpectedly found by the present inventors that diaminophenothiazine (DAPTZ) compounds may be used to provide symptomatic relief of cognitive impairment independently of the presence of any underlying pathology of the AD-type. Improved spatial reference memory has been demonstrated in a model comparing young and aged mice, and also normal and scopolamine-treated mice.

This represents an alternative treatment modality to existing MCI treatments.

Previous Uses of Diaminophenothiazine Compounds

Diaminophenothiazines have previously been shown to inhibit tau protein aggregation and to disrupt the structure of PHFs, and reverse the proteolytic stability of the PHF core (see WO96/30766, F Hoffman-La Roche). Such compounds were disclosed for use in the treatment and prophylaxis of various diseases, including AD and Lewy Body Disease.

Additionally WO 02/055720 (The University Court of the University of Aberdeen) discusses the use of reduced forms of diaminophenothiazines specifically for the treatment of a variety of protein aggregating diseases, although the disclosure is primarily concerned with tauopathies.

WO 2005/030676 (The University Court of the University of Aberdeen) discusses radiolabelled phenothiazines, and their use in diagnosis and therapy e.g. of tauopathies.

By contrast with the above, the present invention relates to the treatment of MCI specifically.

Several studies have proposed that it would be desirable if drugs (such as Methyl Thioninium Chloride (MTC), also known as Methylene Blue) had effects on memory which could be mediated by enhancement of mitochondrial respiration (e.g. Callaway et al., 2002; Callaway et al., 2004; Riha et al., 2005). None of these, however, disclose the use of MTC in symptomatic treatment of MCI.

Martinez et al. ("Methylene blue alters retention of inhibitory avoidance responses". Physiol Psychol 1978, 6:387-390) investigated the effects of MTC in a one-trial inhibitory avoidance step-through task. The authors conclude that methylene blue has both an amnestic effect (i.e. causing amnesia) and a memory-enhancing effect within the conceptual framework of the paper. They claim that the different effects are seen at different doses, amnestic effect at high dose pre-training, and learning enhancing effect post-training at low dose. The key conclusion of the paper is that manipulation of the pentose phosphate pathway may act to modulate memory storage processes.

Callaway et al. ("Methylene blue restores spatial memory retention impaired by an inhibitor of cytochrome oxidase in rats". Neurosci. Lett. 2002, 332:83-86) proposed that MB corrected behavioural impairments induced by a mitochondrial inhibitory agent (sodium azide). However, an objective review of the technical disclosure shows that there is no evidence that MB corrected a learning defect produced by sodium azide, and also that the interpretation of the data suggesting that there is nevertheless a selective effect on memory without an effect on learning is implausible in the light of defects in the experimental design. Specifically, the experimental design did not control for the change in the task from olfactory cue detection during the training phase to a different task during the probe phase of the experiment.

Notwithstanding the above, the authors present the inference that: "The results from this study suggest that MB has the potential to positively affect the clinical outcome of memory retention difficulties in neurodegenerative disorders associated with mitochondrial dysfunction." However neither the data nor the authors suggested the use of MB could act as a cognitive enhancer in the absence of mitochondrial dysfunction.

Gonzalez-Lima F and Bruchey A K ("Extinction memory improvement by the metabolic enhancer methylene blue". Learning and Memory, 2004 11(5):633-640) examined post-extinction administration of MTC to determine whether MTC could enhance retention of an extinguished conditioned response. The authors draw the inference: "MB administration in conjunction with extinction behavioural therapy in humans may be a useful therapeutic agent to facilitate retention of extinction of conditioned fear or other traumatic memories." That is, the authors are advocating a targeted use of MTC to achieve an amnestic effect in certain specific circumstances.

Callaway et al. ("Methylene blue improves brain oxidative metabolism and memory retention in rats Pharmacol". Biochem. Behav. 2004, 77:175-181) used the same behavioural paradigm as in Callaway et al. (2002). However an objective review of the technical content of the paper reveals no evidence that MB improved learning in otherwise unimpaired animals. The interpretation of the data suggesting that there is nevertheless a selective effect on memory without an effect on learning is implausible in the light of defects in the experimental design. Specifically, the experimental design did not control for the change in the task from olfactory cue detection during the training phase to a different task during the probe phase of the experiment. Therefore, there is no evidence that MB improved memory in otherwise unimpaired animals. The authors also showed that cytochrome oxidase c activity was increased in brain tissues obtained 24 hr, but not 1 hr or 2 hr, after a single dose 1 mg/kg dose, and that MB introduced in vitro into a preparation of cytochrome c and brain tissue increased cytochrome c oxidation. However, as discussed in Example 3, the brain levels of MB are maximal at 1-4 hr post administration, and it is therefore implausible to argue that MB produces specific cytochrome oxidase effects of MB at 24 hr but not at 1 hr or 2 hr. From these findings the authors draw the inference that "the mechanism of action of MB in memory retention may be related to enhancement of cytochrome c oxidation".

Riha et al. ("Memory facilitation by methylene blue: Dose-dependent effect on behaviour and brain oxygen consumption". Eur. J. Pharmacol. 2005, 511:151-158) report that rats treated with 1-4 mg/kg MB were not different from saline-treated rats in locomotion or feeding behaviour, but that the 4 mg/kg dose improved behavioural habituation and object memory recognition. However, an objective review of the technical disclosure fails to provide support for the contention that there is any specific effect on behavioural habituation as distinct from non-specific effects on locomotion. Furthermore, the results fail to demonstrate that MB enhances detection of a familiar object relative to saline treatment as measured by reduction of exploration in the vicinity of the familiar object. Therefore, there is no evidence of memory facilitation in otherwise unimpaired rats. They also reported that low concentrations of MB increased brain oxygen consumption in vitro and 24 hr after in vivo administration, but not at 1 hr or 2 hr post administration. From this, the concluded that "methylene blue doses that increase brain oxygen consumption also facilitate memory retention." From this they draw the following inference: "Based on our findings, it is possible that methylene blue may also be useful as a memory enhancer in humans with reduced brain oxidative metabolism, such as individuals with Alzheimer's and vascular dementia."

Wrubel et al. (2007) ("Methylene blue facilitates the extinction of fear in an animal model of susceptibility of learned helplessness." Neurobiol. Learn. Mem. 2007, 87: 209-217) examine the effect on methylene blue on conditioned fear extinction in female congenitally helpless rats. The authors found that methylene blue did not enhance memory retention of extinction if administered during the acquisition of extinction. That is, MB did not have an effect on learning of extinction. Nevertheless, the authors reported that MB enhanced forgetting of previously traumatic stimuli. They draw the inference that "methylene blue may facilitate fear extinction as an adjunct to exposure therapy." That is, the authors again advocate the use of MTC to achieve an amnestic effect in certain specific circumstances.

Callaway et al. (2002), Riha et al. (2005) and Callaway et al. (2004) use approximately the same form of words to articulate the following general mechanism: "While traditional pharmacological treatments to improve memory focus on specific synaptic transmitters, metabolic enhancers like methylene blue may improve overall brain energy production and memory retention by targeting mitochondrial oxidative metabolism, without producing side effects associated with modifying a particular neurotransmitter system" (Callaway et al., 2002). Thus the clinical conditions for which they suggest the use of methylene blue are: "neurodegenerative disorders associated with mitochondrial dysfunction", enumerated more specifically as Leigh's disease and Alzheimer's disease (Callaway et al., 2002), or "humans with reduced brain oxidative metabolism, such as individuals with Alzheimer's and vascular dementia" (Riha et al., 2005).

None of the studies enumerated have drawn the inference, nor have they provided grounds for drawing the inference, that MTC could be used symptomatically in treating MCI.

However in the Examples below, the use of a diaminophenothiazine (exemplified by MTC) has been demonstrated in discrete cognitive impairment models, including aged wild-type mice, in which no tau pathology, neurodegenerative disorder, vascular dementia, disease of impaired oxygen-consumption, or mitochondrial defect would exist, and thus is entirely unexpected in the light of its known prior art effects in these contexts. Specifically, diaminophenothiazines (exemplified by MTC) are shown to improve memory in situations where there is no expectation of mitochondrial dysfunction, reduced brain oxidative metabolism or vascular impairment.

Present Invention

This unexpected discovery thus has implications for providing symptomatic relief of MCI, for which (as discussed above) there is a significant need for novel treatments.

Thus in various aspects the invention provides:

i) Use of a DAPTZ compound in the preparation (or manufacturing process) of a medicament for the treatment of MCI in a patient. Said medicament so prepared or manufactured will include the DAPTZ compound as the or one active ingredient.

ii) A method for the treatment of MCI in a patient, which method comprises administering an effective amount of a DAPTZ compound.

iii) A DAPTZ compound for use in the treatment of MCI in a patient, which method comprises administering an effective amount of DAPTZ compound.

Preferred DAPTZ compounds are discussed in more detail hereinafter.

The administration of the effective amount will be such as to bring benefit to the patient e.g. amelioration of amnestic symptoms.

Diaminophenothizines may be administered alone, or in combination with other treatments, either simultaneously or sequentially.

Interestingly, since the action of MTC in the Examples below was specific for within-session improvements and there was a trend towards between-session memory enhancements too, it is believed that that the reversal of memory impairment by DAPTZ compounds is not through an action on the cholinergic system. Thus the treatment may be such as to provide benefit via a non-cholinergic mechanism. Likewise, the treatment may be such as to provide benefit via a non-tau-aggregation-inhibition mechanism.

Interestingly, not only did MTC show a better therapeutic index than rivastigmine when the drugs were administered individually, but co-administration of sub-effective doses of both rivastigmine and MTC acted synergistically in reversing learning deficits and scopolamine-induced memory impairments. Thus, when combined with ChEI therapy, the effect of MTC appears to be amplified supporting the fact that this combination therapy could potentially improve not only symptoms but also contribute beneficially to neuronal metabolism thereby enabling the use of lower doses of drugs that might minimise the risk of side effects.

The use of DAPTZ compounds such as MTC in combination with cholinergic drugs (e.g. those that enhance or mimics the action of acetylcholine) for the symptomatic treatment of MCI is one embodiment of the present invention.

Thus in one embodiment, treatment may optionally be in combination with one or more other agents, for example, one or more cholinesterase inhibitors (such as donepezil (also known as Aricept™), rivastigmine (also known as Exelon™), galantamine (also known as Reminyl™), NMDA receptor antagonists (such as memantine (also known as Ebixa™, Namenda™), muscarinic receptor agonists, and/or inhibitors of amyloid precursor protein processing that leads to enhanced generation of beta-amyloid.

Assessing and Diagnosing MCI

While there is still discussion in the literature as to the nature of the MCI concept (see Gauthier S. et al., Mild Cognitive Impairment, Lancet, 2006; 367: 1262-1270; Petersen R C et al. Neuropathological features of amnestic mild cognitive impairment. Arch Neurol 2006; 63: 665-672) MCI is recognised as a valid disease target by the FDA. It is defined by having a minor degree of cognitive impairment not yet meeting clinical criteria for a diagnosis of dementia.

Representative criteria for syndromal MCI include features listed below:
A. The patient is neither normal nor demented.
B. There is evidence of cognitive deterioration shown by either objectively measured decline over time and/or subjective report of decline by self and/or informant in conjunction with objective cognitive tests (e.g. secondary tests if memory).
C. Activities of daily living are preserved and complex instrumental functions are either intact or minimally impaired.

(See also Winbiad, B. et al. (2004) Mild cognitive impairment—beyond controversies, towards a concensus: report of the International Working Group on Mild Cognitive Impairment. J. Intern. Med. 256: 240-246).

As used above, the term "dementia" refers to a psychiatric condition in its broadest sense, as defined in American Psychiatric Association: Diagnostic and Statistical Manual of Mental Disorders, Fourth Edition, Washington, D.C., 1994 ("DSM-IV"). The DSM-IV defines "dementia" as characterized by multiple cognitive deficits that include impairments in memory and lists various dementias according to presumed etiology. The DSM-IV sets forth a generally accepted standard for such diagnosing, categorizing and treating of dementia and associated psychiatric disorders.

The MCI may be "amnestic".

By one preferred definition, individuals with amnestic MCI have general cognitive measures within 0.5 standard deviations of control subjects and also have memory performance 1.5 standard deviations below control subjects. An objective, documented decline in memory is useful in determining which individuals have MCI.

"MCI-nonamnestic" or "MCI-other" may be defined as deficits in two or more areas of cognition greater than 1.5 standard deviations below the mean, corrected for age and education.

Preferred Patient Groups

The patient will generally be one diagnosed with MCI, but be one not diagnosed with AD (i.e. will not show dementia). The patient will benefit from the symptomatic relief as described above.

The patient may, for example, be aged over 45, 50, 55 years.

The patient may be one meeting one or all of the following criteria in respect of: (i) Braak stage; (ii) MMSE score.
(i) Braak Stage In the Braak stageing scheme, disease progression is divided into 7 stages (Braak stage 0 (herein designated as "BST 0" or "B0") to Braak stage 6 ("BST 6" or "B6")). The system is based on the characteristic neuroanatomical progression of the neurofibrillary pathology of AD (Braak and Braak (Neuropathological stageing of Alzheimer-related changes. Acta Neuropathol (Berl). 1991; 82(4):239-59).

Methods for assessing neurofibrillary degeneration are disclosed in WO02/075318.

In one embodiment the MCI patient group which it is desired to treat by the methods of the present invention is at BST 3 or less, BST 2 or less, more preferably 1 or less, more preferably 0. The preferred patient group will have a relatively low probability of clinical dementia and a relatively low probability of representing early stages of AD, but nevertheless still suffer MCI.
(ii) MMSE Score Patients may demonstrate a stable or declining cognitive impairment characteristic of MCI (along with the further relevant clinical features) at a point in time.

The Mini-Mental State Examination (MMSE) is a standardised test which was proposed as a simple and quickly administered method for grading cognitive function (Folstein M F, Folstein S E & McHugh P R. 'Mini-mental state'. A practical method for grading the cognitive state of patients for the clinician. *Journal of Psychiatric Research* 1975 12 189-198.). The MMSE is the most widely used cognitive screening instrument for the detection of cognitive dysfunction due to dementia in geriatric and psychiatric patients (Tombaugh T N & McIntyre N J. The mini-mental state examination: a comprehensive review. *Journal of the American Geriatric Society* 1992 40 922-935). The MMSE evaluates orientation, memory, attention and language functions.

Patients for whom the present invention may preferably be used may be those with less than or equal to MMSE 24, 25, 26, 27, 28 or 29, more preferably less than or equal to MMSE 24, 25, 26, most preferably less than or equal to MMSE 24 or 25.

Benefit and Treatment

By "treatment of" or "bringing benefit to" the patient is meant amelioration of a condition, including any objective or subjective parameter such as abatement; remission; diminishing of symptoms; slowing in the rate of degeneration or decline.

The treatment or amelioration of symptoms can be based on objective or subjective parameters; including the results of a neuropsychiatric examination, and/or a psychiatric evaluation e.g. improving performance of memory task tests demonstrating relief of mild memory loss or impairment and/or relief of other mild cognitive deficit.

Products and Kits

In another aspect, the invention provides a drug product for the treatment of MCI in a patient suffering therefrom, comprising a container labelled or accompanied by a label indicating that the drug product is for the treatment of MCI, the container containing one or more dosage units each comprising at least one pharmaceutically acceptable excipient and, as an active ingredient, an isolated pure DAPTZ compound selected from those described herein.

The invention further provides a kit for treating MCI in a human including a DAPTZ compound and instructional material teaching the indications, dosage and schedule of administration of the MTC for treatment of MCI.

Diaminophenothiazine (DAPTZ) Compounds

The invention pertains to certain diaminophenothiazine compounds and analogs thereof, having one of the following formulae, and pharmaceutically acceptable salts, hydrates, and solvates thereof (collectively referred to herein as "diaminophenothiazines" or "diaminophenothiazine compounds"):

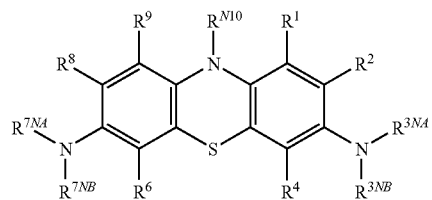
(1)

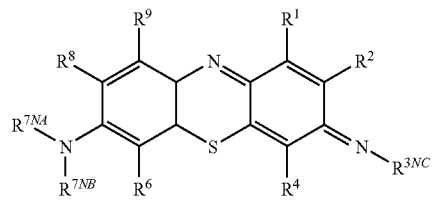
(2)

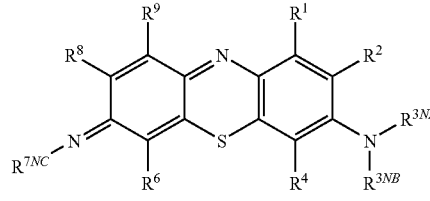
(3)

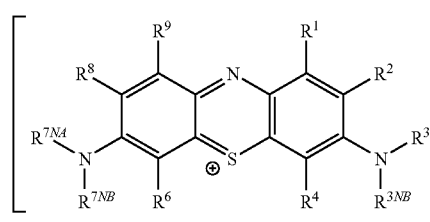
(4)

Formula (1) depicts compounds in a reduced form, whereas each of Formulae (2), (3), and (4) depicts compounds in an oxidized form.

In one embodiment, the compounds are selected from compounds of formula (1), and pharmaceutically acceptable salts, hydrates, and solvates thereof.

In one embodiment, the compounds are selected from compounds of formula (2) or (3), and pharmaceutically acceptable salts, hydrates, and solvates thereof.

In one embodiment, the compounds are selected from compounds of formula (4), and pharmaceutically acceptable salts, hydrates, and solvates thereof.

Each one of the above structures is only one of many equivalent resonance structures, and all of which are intended to be encompassed by that representative structure. For example, structure (4) is only one of many equivalent resonance structures, some of which are shown below, and all of which are intended to be encompassed by structure (4):

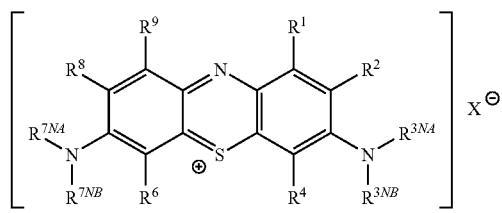
(4-B)

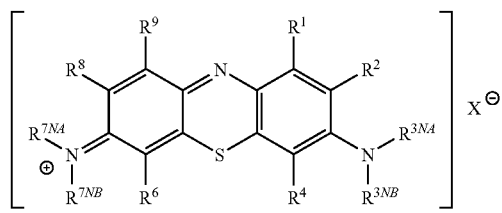
(4-C)

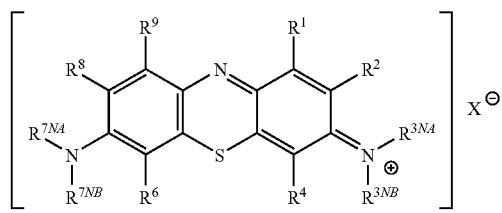
(4-D)

Carbon Ring Atom Substituents

In each one of the above formulae, each one of $R^1$, $R^2$, $R^4$, $R^6$, $R^8$, and $R^9$ is independently selected from:
—H;
—F; —Cl; —Br; —I;
—OH; —OR;
—SH; —SR;
—NO$_2$;
—C(=O)R;
—C(=O)OH; —C(=O)OR;
—C(=O)NH$_2$; —C(=O)NHR; —C(=O)NR$_2$;
—C(=O)NR$^{N1}$R$^{N2}$;
—NH$_2$; —NHR; —NR$_2$; —NR$^{N2}$;
—NHC(=O)H; —NRC(=O)H; —NHC(=O)R; —NRC(=O)R;
—R;

wherein each R is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
unsubstituted $C_{6-10}$carboaryl; substituted $C_{6-10}$carboaryl;
unsubstituted $C_{5-10}$heteroaryl; substituted $C_{5-10}$heteroaryl;
unsubstituted $C_{6-10}$carboaryl-$C_{1-4}$alkyl; substituted $C_{6-10}$carboaryl-$C_{1-4}$alkyl;

wherein, in each group —NR$^{N1}$R$^{N2}$, independently, R$^{N1}$ and R$^{N2}$ taken together with the nitrogen atom to which they are attached form a ring having from 3 to 7 ring atoms.

Examples of groups —NR$^{N1}$R$^{N2}$, wherein R$^{N1}$ and R$^{N2}$ taken together with the nitrogen atom to which they are attached form a ring having from 3 to 7 ring atoms, include: pyrrolidino, piperidino, piperazino, morpholino, pyrrolyl, and substituted forms, such as N-substituted forms, such as N-methyl piperazino.

In one embodiment, each one of $R^1$, $R^2$, $R^4$, $R^6$, $R^8$, and $R^9$ is independently selected from:

—H;
—F; —Cl; —Br; —I;
—OH; —OR;
—C(=O)OH; —C(=O)OR;
—R.

In one embodiment, each one of $R^1$, $R^2$, $R^4$, $R^6$, $R^8$, and $R^9$ is independently selected from:
—H;
—R.

In one embodiment, each R is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl.

In one embodiment, each R is independently selected from:
unsubstituted aliphatic $C_{1-6}$alkyl; substituted aliphatic $C_{1-6}$alkyl.

In one embodiment, each R is independently selected from: -Me, -Et, -nPr, and -iPr.

In one embodiment, each R is independently selected from: -Me and -Et.

In one embodiment, the $C_{1-6}$alkyl group is a $C_{1-4}$alkyl group.

In one embodiment, the $C_{2-6}$alkenyl group is a $C_{2-4}$alkenyl group.

In one embodiment, the $C_{3-6}$cycloalkyl group is a $C_{3-4}$cycloalkyl group.

Examples of unsubstituted aliphatic $C_{1-6}$alkyl groups include: methyl, ethyl, n-propyl, iso-propyl, n-butyl, iso-butyl, sec-butyl, tert-butyl, n-pentyl, iso-pentyl, tert-pentyl, neo-pentyl, hexyl, iso-hexyl, etc.

Examples of unsubstituted aliphatic $C_{2-6}$alkenyl groups include: propen-1-yl, propen-2-yl, buten-1-yl, buten-2-yl, buten-3-yl, etc.

Examples of unsubstituted $C_{3-6}$cycloalkyl groups include: cyclopropyl, cyclopropyl-methyl, cyclobutyl, cyclopentyl, cyclohexyl, etc.

In one embodiment, the $C_{6-10}$carboaryl group is a $C_6$carboaryl group.

In one embodiment, the $C_{5-10}$heteroaryl group is a $C_{5-6}$heteroaryl group.

In one embodiment, the $C_{6-10}$carboaryl-$C_{1-4}$alkyl group is a $C_6$carboaryl-$C_{1-2}$alkyl group.

Examples of unsubstituted $C_{6-10}$carboaryl groups include: phenyl, naphthyl.

Examples of unsubstituted $C_{5-10}$heteroaryl groups include: pyrrolyl, thienyl, furyl, imidazolyl, oxazolyl, isoxazolyl, thiazolyl, isothiazolyl, pyrazolyl, pyridyl, pyrazinyl, pyrimidinyl, pyridazinyl.

Examples of unsubstituted $C_{6-10}$carboaryl-$C_{1-4}$alkyl groups include: benzyl, phenylethyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are independently selected from:
—F; —Cl; —Br; —I;
—OH; —OR';
—SH; —SR';
—NO$_2$;
—C(=O)R';
—C(=O)OH; —C(=O)OR';
—C(=O)NH$_2$; —C(=O)NHR'; —C(=O)NR'$_2$;
—C(=O)NR'$^{N1}$R'$^{N2}$;
—NH$_2$; —NHR'; —NR'$_2$; —NR'$^{N1}$R'$^{N2}$;
—NHC(=O)H; —N'RC(=O)H; —NHC(=O)'R;
—N'RC(=O)'R;
—R';

wherein each R' is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
unsubstituted $C_{6-10}$carboaryl; substituted $C_{6-10}$carboaryl;
unsubstituted $C_{5-10}$heteroaryl; substituted $C_{5-10}$heteroaryl;
unsubstituted $C_{6-10}$carboaryl-$C_{1-4}$alkyl; substituted $C_{6-10}$carboaryl-$C_{1-4}$alkyl;
wherein, in each group —NR'$^{N1}$R'$^{N2}$, independently, R'$^{N1}$ and R'$^{N2}$ taken together with the nitrogen atom to which they are attached form a ring having from 3 to 7 ring atoms.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are independently selected from:
—F; —Cl; —Br; —I;
—OH; —OR';
—C(=O)OH; —C(=O)OR';
—R'.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from:
unsubstituted aliphatic $C_{1-6}$alkyl;
unsubstituted aliphatic $C_{2-6}$alkenyl;
unsubstituted $C_{3-6}$cycloalkyl;
unsubstituted $C_{6-10}$carboaryl;
unsubstituted $C_{5-10}$heteroaryl;
unsubstituted $C_{6-10}$carboaryl-$C_{1-4}$alkyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from:
unsubstituted aliphatic $C_{1-6}$alkyl;
unsubstituted aliphatic $C_{2-6}$alkenyl;
unsubstituted $C_{3-6}$cycloalkyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from:
unsubstituted aliphatic $C_{1-6}$alkyl; substituted aliphatic $C_{1-6}$alkyl.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from: -Me, -Et, -nPr, and -iPr.

In one embodiment, optional substituents (e.g., on aliphatic $C_{1-6}$alkyl, aliphatic $C_{1-6}$alkenyl, $C_{3-6}$cycloalkyl, $C_{6-10}$carboaryl, $C_{5-10}$heteroaryl, $C_{6-10}$carboaryl-$C_{1-4}$alkyl) are as defined above, except that each R' is independently selected from: -Me and -Et.

In one embodiment, each one of $R^1$, $R^2$, $R^4$, $R^6$, $R^8$, and $R^9$ is independently selected from: —H, -Me, -Et, -nPr, and -iPr.

In one embodiment, each one of $R^1$, $R^2$, $R^4$, $R^6$, $R^8$, and $R^9$ is independently selected from: —H, -Me, and -Et.

In one embodiment, each one of $R^1$, $R^2$, $R^4$, $R^6$, $R^8$, and $R^9$ is independently selected from: —H and -Me.

In one embodiment, all except four of $R^1$, $R^2$, $R^4$, $R^6$, $R^8$, and $R^9$ is —H.

In one embodiment, all except two of $R^1$, $R^2$, $R^4$, $R^6$, $R^8$, and $R^9$ is —H.

In one embodiment, all except one of $R^1$, $R^2$, $R^4$, $R^6$, $R^8$, and $R^9$ is —H.

In one embodiment, each of $R^1$, $R^2$, $R^4$, $R^6$, $R^8$, and $R^9$ is —H.

Amino Groups

In each one of the above formulae, in each group —$NR^{3NA}R^{3NB}$, if present, each one of $R^{3NA}$ and $R^{3NB}$ is independently —H or as defined above for R; or $R^{3NA}$ and $R^{3NB}$ taken together with the nitrogen atom to which they are attached form a ring having from 3 to 7 ring atoms.

For example, in one embodiment, in each group —$NR^{3NA}R^{3NB}$, if present, each one of $R^{3NA}$ and $R^{3NB}$ is independently as defined above for R; or $R^{3NA}$ and $R^{3NB}$ taken together with the nitrogen atom to which they are attached form a ring having from 3 to 7 ring atoms.

For example, in one embodiment, in each group —$NR^{3NA}R^{3NB}$, if present, each one of $R^{3NA}$ and $R^{3NB}$ is independently selected from:
—H;
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
unsubstituted $C_{6-10}$carboaryl; substituted $C_{6-10}$carboaryl;
unsubstituted $C_{5-10}$heteroaryl; substituted $C_{5-10}$heteroaryl;
unsubstituted $C_{6-10}$carboaryl-$C_{1-4}$alkyl; substituted $C_{6-10}$carboaryl-$C_{1-4}$alkyl;
or $R^{3NA}$ and $R^{3NB}$ taken together with the nitrogen atom to which they are attached form a ring having from 3 to 7 ring atoms.

For example, in one embodiment, in each group —$NR^{3NA}R^{3NB}$, if present, each one of $R^{3NA}$ and $R^{3NB}$ is independently selected from:
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
unsubstituted $C_{6-10}$carboaryl; substituted $C_{6-10}$carboaryl;
unsubstituted $C_{5-10}$heteroaryl; substituted $C_{5-10}$heteroaryl;
unsubstituted $C_{6-10}$carboaryl-$C_{1-4}$alkyl; substituted $C_{6-10}$carboaryl-$C_{1-4}$alkyl;
or $R^{3NA}$ and $R^{3NB}$ taken together with the nitrogen atom to which they are attached form a ring having from 3 to 7 ring atoms.

In another example, in one embodiment, in each group —$NR^{3NA}R^{3NB}$, if present, each one of $R^{3NA}$ and $R^{3NB}$ is independently selected from:
—H;
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
or $R^{3NA}$ and $R^{3NB}$ taken together with the nitrogen atom to which they are attached form a ring having from 3 to 7 ring atoms.

In another example, in one embodiment, in each group —$NR^{3NA}R^{3NB}$, if present, each one of $R^{3NA}$ and $R^{3NB}$ is independently selected from:
—H;
unsubstituted aliphatic $C_{1-6}$alkyl;
unsubstituted aliphatic $C_{2-6}$alkenyl;
unsubstituted $C_{3-6}$cycloalkyl;
or $R^{3NA}$ and $R^{3NB}$ taken together with the nitrogen atom to which they are attached form a ring having from 3 to 7 ring atoms.

In another example, in one embodiment, in each group —$NR^{3NA}R^{3NB}$, if present, each one of $R^{3NA}$ and $R^{3NB}$ is independently selected from:
unsubstituted aliphatic $C_{1-6}$alkyl;
unsubstituted aliphatic $C_{2-6}$alkenyl;
unsubstituted $C_{3-6}$cycloalkyl;
or $R^{3NA}$ and $R^{3NB}$ taken together with the nitrogen atom to which they are attached form a ring having from 3 to 7 ring atoms.

In another example, in one embodiment, in each group —$NR^{3NA}R^{3NB}$, if present, each one of $R^{3NA}$ and $R^{3NB}$ is independently selected from: —H, -Me, -Et, -nPr, and -iPr.

In another example, in one embodiment, in each group —$NR^{3NA}R^{3NB}$, if present, each one of $R^{3NA}$ and $R^{3NB}$ is independently selected from: —H, -Me, and -Et (e.g., —$NR^{3NA}R^{3NA}$ is —$NH_2$, —NHMe, —$NMe_2$, —NHEt, —$NEt_2$, or —NMeEt).

In another example, in one embodiment, in each group —$NR^{3NA}R^{3NB}$, if present, each one of $R^{3NA}$ and $R^{3NB}$ is independently selected from: —H and -Me (e.g., —$NR^{3NA}R^{3NA}$ is —$NH_2$, —NHMe, or —$NMe_2$).

In precise analogy, in each one of the above formulae, in each group —$NR^{7NA}R^{7NB}$, if present, each one of $R^{7NA}$ and $R^{7NB}$ is independently —H or as defined above for R; or $R^{7NA}$ and $R^{7NB}$ taken together with the nitrogen atom to which they are attached form a ring having from 3 to 7 ring atoms.

For example, in one embodiment, in each group —$NR^{7NA}R^{7NB}$, if present, each one of $R^{7NA}$ and $R^{7NB}$ is independently as defined above for R; or $R^{7NA}$ and $R^{7NB}$ taken together with the nitrogen atom to which they are attached form a ring having from 3 to 7 ring atoms.

In one embodiment, —$NR^{3NA}R^{3NB}$ and —$NR^{7NA}R^{7NB}$, if both present, are the same.

In one embodiment, —$NR^{3NA}R^{3B}$ and —$NR^{7NA}R^{7NB}$, if both present, are different.

In each one of the above formulae, in each group =$NR^{3NC}$, if present, $R^{3NC}$ is independently —H or as defined above for R.

For example, in one embodiment, in each group =$NR^{3NC}$, if present, $R^{3NC}$ is independently as defined above for R.

For example, in one embodiment, in each group =$NR^{3NC}$, if present, $R^{3NC}$ is independently selected from:
—H;
unsubstituted aliphatic $C_{1-6}$alkyl; substituted aliphatic $C_{1-6}$alkyl;
unsubstituted aliphatic $C_{2-6}$alkenyl; substituted aliphatic $C_{2-6}$alkenyl;
unsubstituted $C_{3-6}$cycloalkyl; substituted $C_{3-6}$cycloalkyl;
unsubstituted $C_{6-10}$carboaryl; substituted $C_{6-10}$carboaryl;
unsubstituted $C_{5-10}$heteroaryl; substituted $C_{5-10}$heteroaryl;
unsubstituted $C_{6-10}$carboaryl-$C_{1-4}$alkyl; substituted $C_{6-10}$carboaryl-$C_{1-4}$alkyl.

For example, in one embodiment, in each group =$NR^{3NC}$, if present, $R^{3NC}$ is independently selected from:
  unsubstituted aliphatic $C_{1-6}$alkyl; substituted aliphatic $C_{1-6}$alkyl;
  unsubstituted aliphatic $C_{2-6}$alkenyl; substituted aliphatic $C_{2-6}$alkenyl;
  unsubstituted $C_{3-6}$cycloalkyl; substituted $C_{3-6}$cycloalkyl;
  unsubstituted $C_{6-10}$carboaryl; substituted $C_{6-10}$carboaryl;
  unsubstituted $C_{5-10}$heteroaryl; substituted $C_{5-10}$heteroaryl;
  unsubstituted $C_{6-10}$carboaryl-$C_{1-4}$alkyl; substituted $C_{6-10}$carboaryl-$C_{1-4}$alkyl.

In another example, in one embodiment, in each group =$NR^{3NC}$, if present, $R^{3NC}$ is independently selected from:
  —H;
  unsubstituted aliphatic $C_{1-6}$alkyl; substituted aliphatic $C_{1-6}$alkyl;
  unsubstituted aliphatic $C_{2-6}$alkenyl; substituted aliphatic $C_{2-6}$alkenyl;
  unsubstituted $C_{3-6}$cycloalkyl; substituted $C_{3-6}$cycloalkyl.

In another example, in one embodiment, in each group =$NR^{3NC}$, if present, $R^{3NC}$ is independently selected from:
  unsubstituted aliphatic $C_{1-6}$alkyl; substituted aliphatic $C_{1-6}$alkyl;
  unsubstituted aliphatic $C_{2-6}$alkenyl; substituted aliphatic $C_{2-6}$alkenyl;
  unsubstituted $C_{3-6}$cycloalkyl; substituted $C_{3-6}$cycloalkyl.

In another example, in one embodiment, in each group =$NR^{3NC}$, if present, $R^{3NC}$ is independently selected from:
  —H;
  unsubstituted aliphatic $C_{1-6}$alkyl;
  unsubstituted aliphatic $C_{2-6}$alkenyl;
  unsubstituted $C_{3-6}$cycloalkyl.

In another example, in one embodiment, in each group =$NR^{3NC}$, if present, $R^{3NC}$ is independently selected from:
  unsubstituted aliphatic $C_{1-6}$alkyl;
  unsubstituted aliphatic $C_{2-6}$alkenyl;
  unsubstituted $C_{3-6}$cycloalkyl.

In another example, in one embodiment, in each group =$NR^{3NC}$, if present, $R^{3NC}$ is independently selected from: —H, -Me, -Et, -nPr, and -iPr.

In another example, in one embodiment, in each group =$NR^{3NC}$, if present, $R^{3NC}$ is independently selected from: —H, -Me, and -Et (e.g., =$NR^{3NC}$ is =NH, =NMe, or =NEt).

In another example, in one embodiment, in each group =$NR^{3NC}$, if present, $R^{3NC}$ is independently selected from: —H and -Me (e.g., =$NR^{3NC}$ is =NH or =NMe).

In precise analogy, in each one of the above formulae, in each group =$NR^{7NC}$, if present, $R^{7NC}$ is independently as defined above for $R^{3NC}$.

Nitrogen Ring Atom Substituent

Also, in precise analogy, in each one of the above formulae, $R^{N10}$, if present, is independently as defined above for $R^{3NC}$ (or $R^{7NC}$).

For example, in one embodiment, $R^{N10}$, if present, is independently selected from: —H and unsubstituted aliphatic $C_{1-6}$alkyl.

For example, in one embodiment, $R^{N10}$, if present, is independently selected from: —H, -Me, and -Et.

For example, in one embodiment, $R^{N10}$, if present, is independently selected from: —H and -Me.

For example, in one embodiment, $R^{N10}$, if present, is independently —H.

Counter Ion $X^-$, if present, is one or more anionic counter ions to achieve electrical neutrality.

Examples of suitable anionic counter ions are discussed below under the heading "Salts".

In one embodiment, $X^-$ is independently a halogen anion (i.e., a halide).
In one embodiment, $X^-$ is independently $Cl^-$, $Br^-$, or $I^-$.
In one embodiment, $X^-$ is independently $Cl^-$.
In one embodiment, $X^-$ is independently $NO_3^-$.

Combinations

All plausible combinations of the embodiments described above are disclosed herein as if each combination was individually and explicitly recited.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

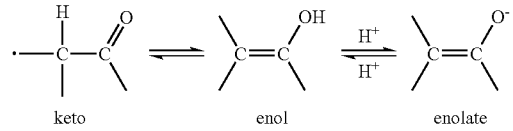

keto    enol    enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{11}C$, $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

The compound may also be provided in the form of a mixed salt (i.e., the compound in combination with a salt, or another salt). For example, methyl-thioninium chloride zinc chloride mixed salt (MTZ) is a mixed salt of methyl-thioninium chloride (MTC), a chloride salt, and another salt, zinc chloride. Such mixed salts are intended to be encompassed by the term "and pharmaceutically acceptable salts thereof".

Unless otherwise specified, a reference to a particular compound also includes salt forms thereof.

Hydrates and Solvates

It may be convenient or desirable to prepare, purify, and/or handle a corresponding solvate of the active compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate forms thereof.

Some Preferred Examples

Some preferred diaminophenothiazines include the following, and pharmaceutically acceptable salts, hydrates, and solvates thereof:

A  MTC

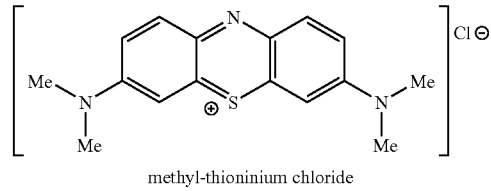

methyl-thioninium chloride

B  ETC

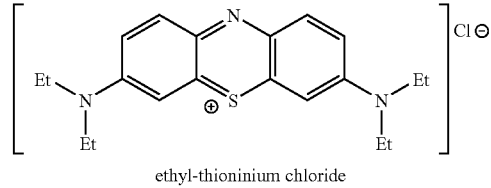

ethyl-thioninium chloride

C  DMMTC

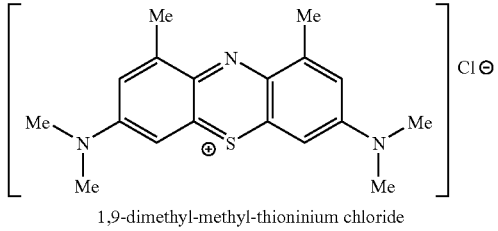

1,9-dimethyl-methyl-thioninium chloride

| | | |
|---|---|---|
| D | DEMTC | 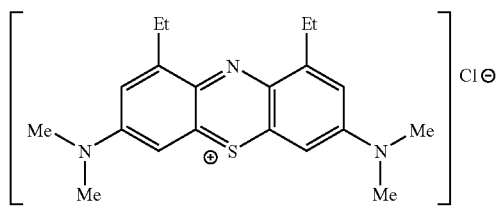
1,9-diethyl-methyl-thioninium chloride |
| E | DMETC | 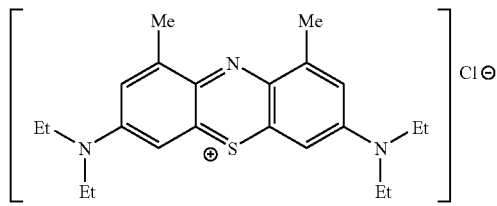
1,9-dimethyl-ethyl-thioninium chloride |
| F | DEETC | 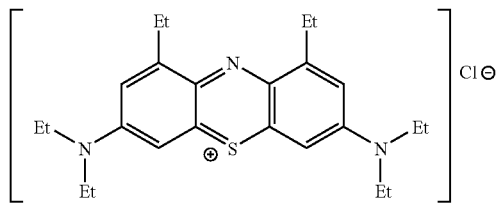
1,9-diethyl-ethyl-thioninium chloride |
| G | MTZ | 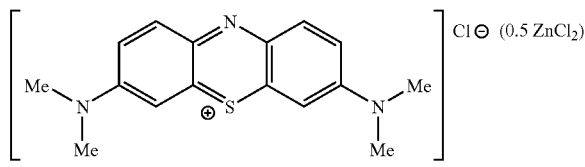
methyl-thioninium chloride zinc chloride mixed salt |
| H | ETZ | 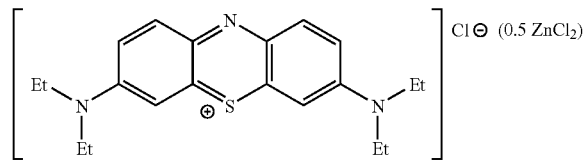
ethyl-thioninium chloride zinc chloride mixed salt |
| I | MTI | 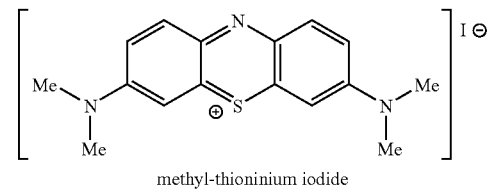
methyl-thioninium iodide |
| J | MTI.HI | 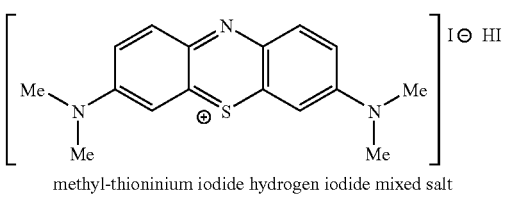
methyl-thioninium iodide hydrogen iodide mixed salt |

-continued

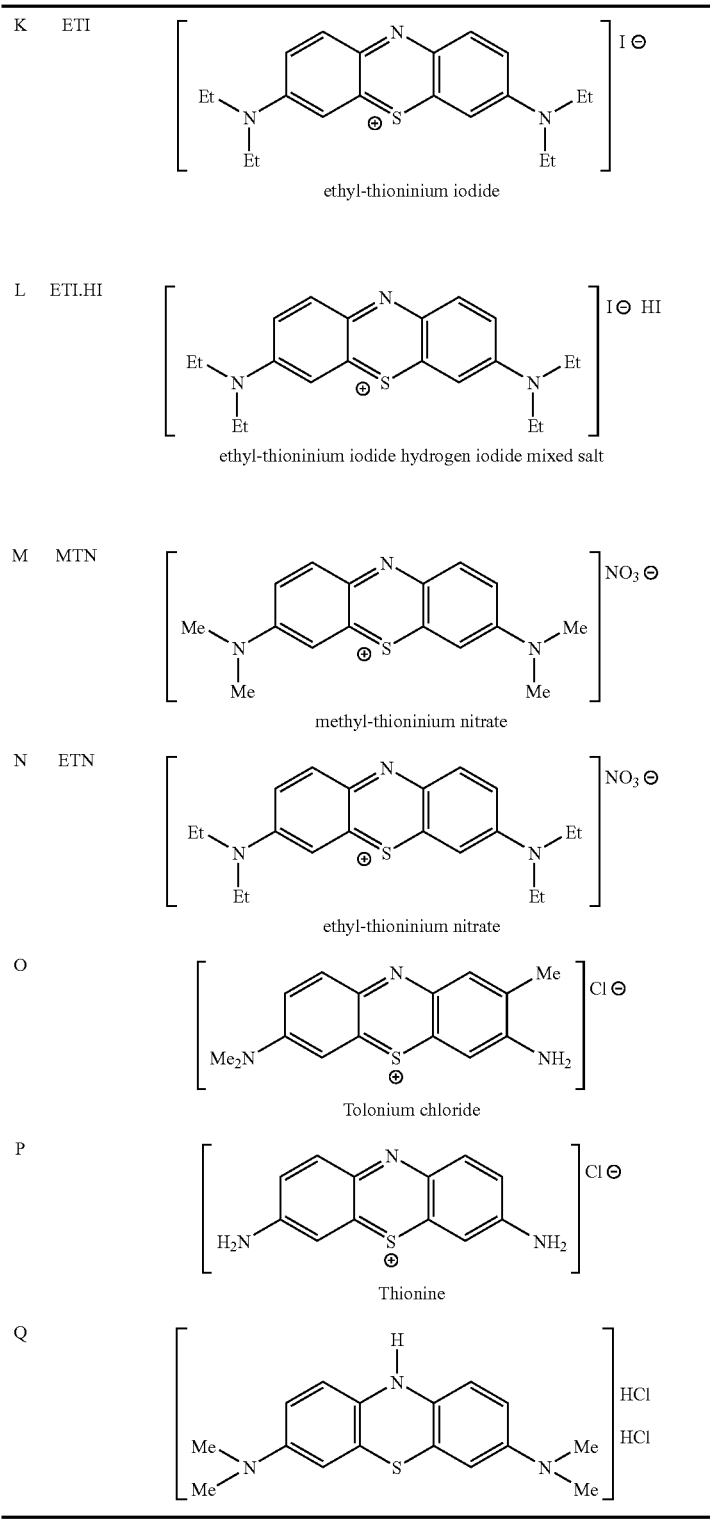

In one embodiment, the diaminophenothiazine is selected from: MTC, ETC, DEMTC, DEETC, Thionine, and Tolonium Chloride (also known as Toluidine Blue O), and compound Example 'Q above. Compound Q may be prepared as described in co-pending applications based on U.S. Provisional Patent Application No. 60/786,690 filed 29 Mar. 2006 entitled "3,7-Diamino-10H-Phenothiazine Salts and Their Use" (Wischik et al.—published as WO2007-110627).

Dosage Units, and Formulation and Administration of Compounds

Administration of compounds, compositions or medicaments as described herein is preferably in a "therapeutically effective amount", this being sufficient to show benefit to the individual as discussed above.

For medicaments the actual amount administered, and rate and time-course of administration, will depend on the nature and severity of the MCI being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

Example phenothiazines of the present invention are known in the art and may be manufactured by the processes referred to in standard texts (e.g. Merck Manual, Houben-Weyl, Beilstein E III/IV 27, 1214 ff, J. Heterocycl. Chem. 21, 613 (1984), etc.). The compounds of the above formulae, their pharmaceutically acceptable salts, or other compounds found to have the properties defined in the assays provided, could be used as medicaments after further testing for toxicity (e.g. in the form of pharmaceutical preparations).

The prior pharmaceutical use of methylene blue in a wide range of medical indications has been described, including treatment of methaemoglobineamia and the prophylaxis of manic depressive psychosis (Naylor (1986) Biol. Psychiatry 21, 915-920), and CNS penetration following systemic administration has been described (Muller (1992) Acta Anat., 144, 39-44). The production of Azure A and B occur as normal metabolic degradation products of methylene blue (Di Santo and Wagner (1972a) J. Pharm. Sci. 61, 598-602; Di Santo and Wagner (1972b) J. Pharm. Sci. 61 1086-1094). The administration of pharmaceuticals can be effected parentally such as orally, in the form of tablets, coated tablets, dragees, hard and soft gelatine capsules, solutions, emulsions or suspensions), nasally (e.g. in the form of nasal sprays) or rectally (e.g. in the form of suppositories). However, the administration can also be effected parentally such as intramuscularly or intravenously (e.g. in the form of injection solutions).

The compositions may include, in addition to the above constituents, pharmaceutically-acceptable excipients, preserving agents, solubilizers, viscosity-increasing substances, stabilising agents, wetting agents, emulsifying agents, sweetening agents, colouring agents, flavouring agents, salts for varying the osmotic pressure, buffers, or coating agents. Such materials should be non-toxic and should not interfere with the efficacy of the active ingredient. The precise nature of the carrier or other material may depend on the route of administration. Examples of techniques and protocols can be found in "Remington's Pharmaceutical Sciences", 16$^{th}$ edition, Osol, A. (ed.), 1980.

Where the composition is formulated into a pharmaceutical composition, the administration thereof can be effected parentally such as orally, in the form of powders, tablets, coated tablets, dragees, hard and soft gelatine capsules, solutions, emulsions or suspensions, nasally (e.g. in the form of nasal sprays) or rectally (e.g. in the form of suppositories). However, the administration can also be effected parentally such as intramuscularly, intravenously, cutaneously, subcutaneously, or intraperitoneally (e.g. in the form of injection solutions).

Thus, for example, where the pharmaceutical composition is in the form of a tablet, it may include a solid carrier such as gelatine or an adjuvant. For the manufacture of tablets, coated tablets, dragees and hard gelatine capsules, the active compounds and their pharmaceutically-acceptable acid addition salts can be processed with pharmaceutically inert, inorganic or organic excipients. Lactose, maize, starch or derivatives thereof, talc, stearic acid or its salts etc. can be used, for example, as such excipients for tablets, dragees and hard gelatine capsules. Suitable excipients for soft gelatine capsules are, for example, vegetable oils, waxes, fats, semi-solid and liquid polyols etc. Where the composition is in the form of a liquid pharmaceutical formulation, it will generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may also be included. Other suitable excipients for the manufacture of solutions and syrups are, for example, water, polyols, saccharose, invert sugar, glucose, trehalose, etc. Suitable excipients for injection solutions are, for example, water, alcohols, polyols, glycerol, vegetable oils, etc. For intravenous, cutaneous or subcutaneous injection, or intracatheter infusion into the brain, the active ingredient will be in the form of a parenterally-acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers and/or other additives may be included, as required.

Uses of the compounds herein as ligands may utilise similar carriers or compositions.

Thus in aspects of the invention wherein a diaminophenothiazine (for example MTC) is used in a method of treatment or therapy of the human or animal body, that method will preferably involve administration of the effective amount of diaminophenothiazine orally.

Preferably the medicament is adapted for oral administration, and preferably is in solid dosage unit form.

Preferably the dosage will be administered orally. Preferably it will be less than or equal to 400, 300, 200, or 100 mg daily total dose. For example it may consist of dosage units of 10, 20, 30, 40, 50, 60, 60, 80, 90, 100, 110, 120, or 130 mg t.i.d. (three times a day)

Alternatively it may consist of dosage units of 10, 20, 30, 40, 50, 60, 60, 80, 90, 100, 110, 120, 130, 140, 150, 160, 170, 180, 190, or 200 mg b.i.d. (twice a day).

Preferably the treatment is continued for equal to or at least 2, 3, or 4 weeks.

Instructions in respect of these dosages may be included in written form on or within the container of a drug product of the invention.

Where administration is in intravenous, it is preferred that the diaminophenothiazine is not MTC.

The disclosure of any cross-reference made herein, inasmuch as it may be required by one skilled in the art to supplement the present disclosure, is hereby specifically incorporated herein.

The invention will now be further described with reference to the following non-limiting Figures and Examples. Other embodiments of the invention will occur to those skilled in the art in the light of these.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1: Effect of drugs in the spatial reference memory task. The ordinate represents the daily path length (mean values of 6 trials±SE) for all drug groups.

Figure 2:
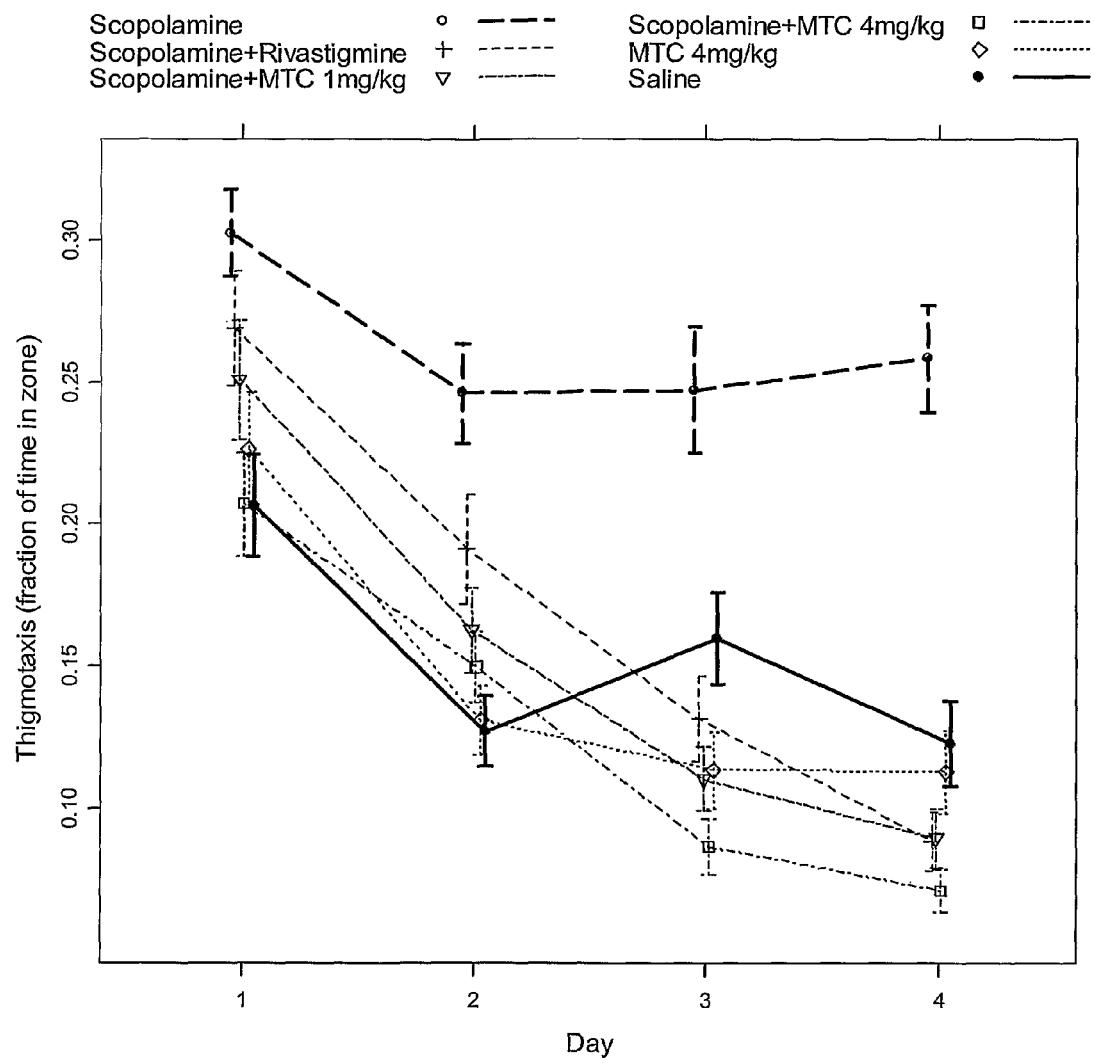

FIG. 2: Effect of drugs on thigmotaxis, expressed as fraction of time spent in the outer 10% area of the pool; daily mean values±SE.

Figure 3:
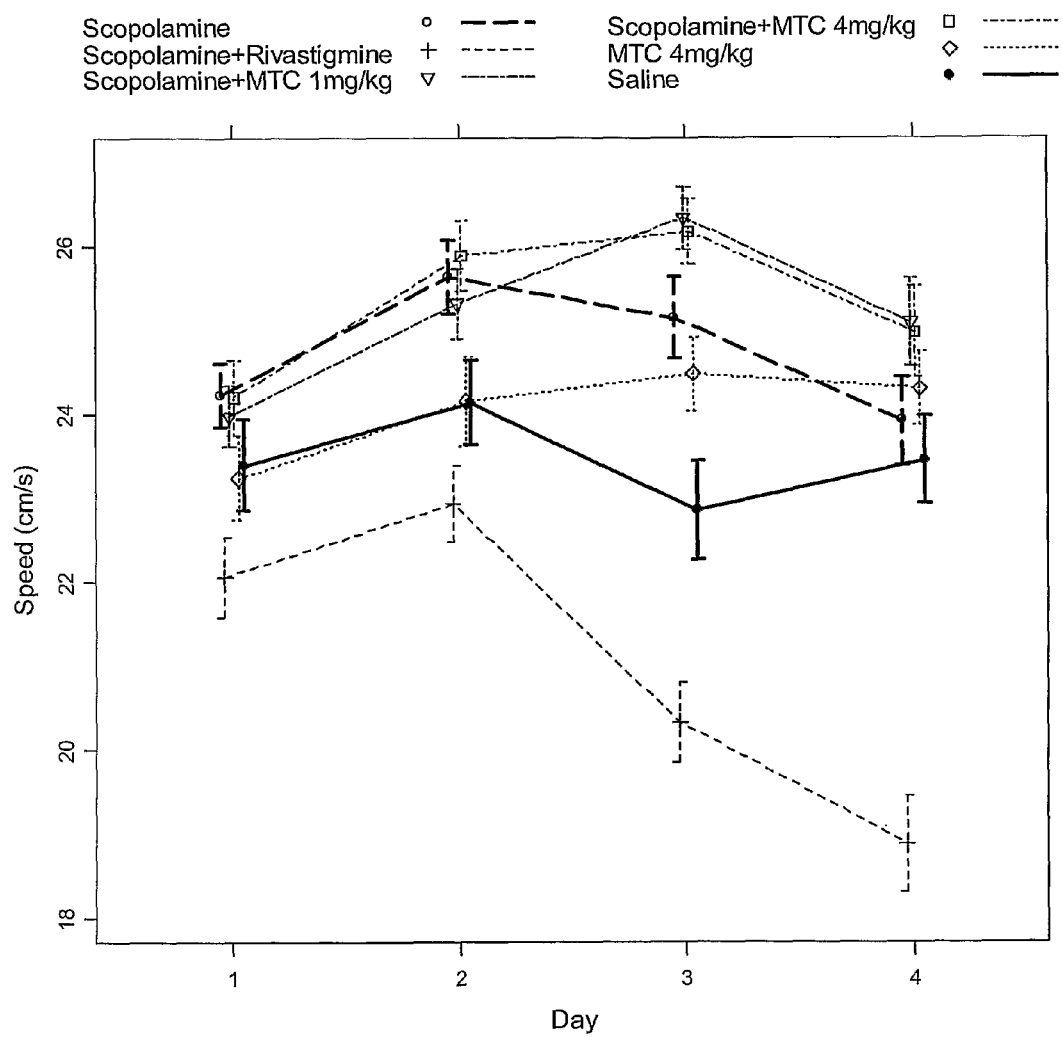

FIG. 3: Effect of the drugs on the swim speed of animals in the water maze. Mean values±SE.

Figure 4:
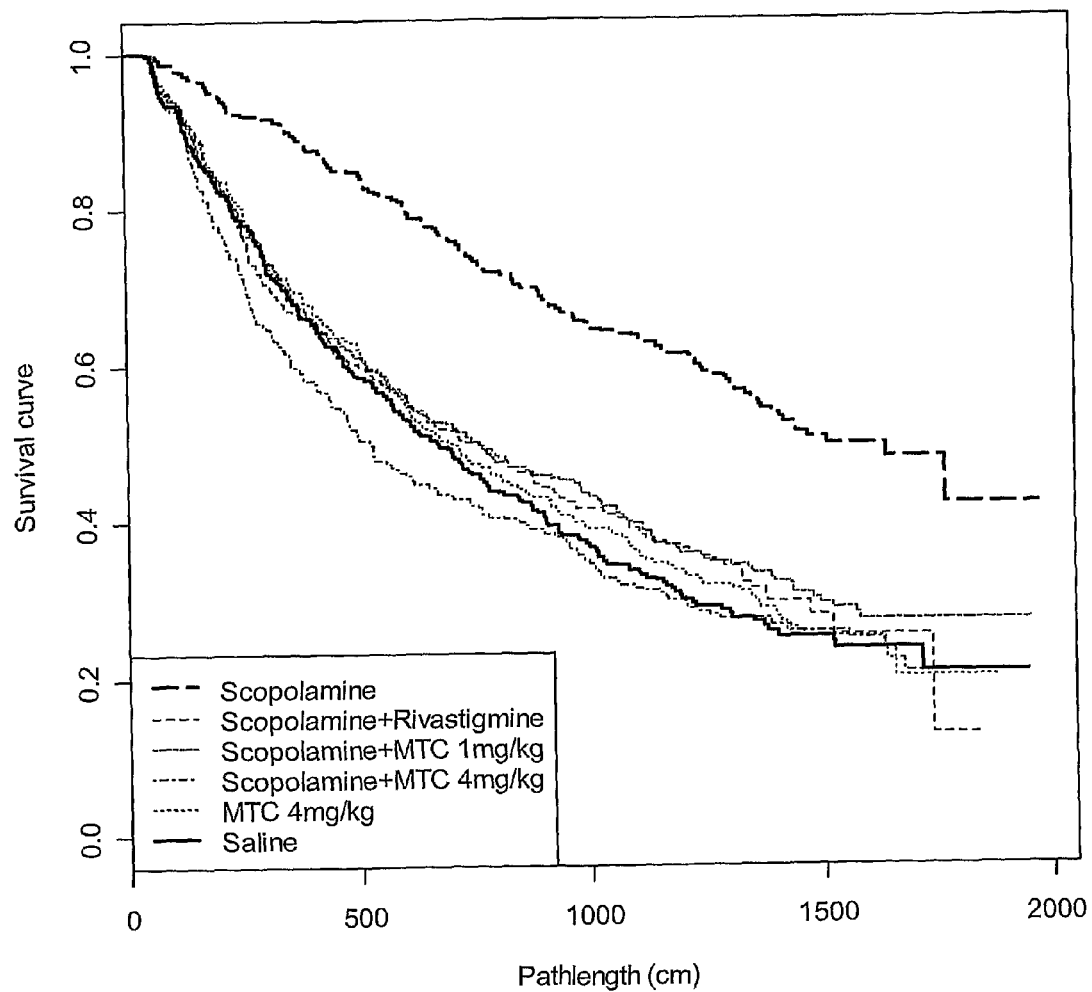

FIG. 4: Survival plot of swim status of animals in learning-phase of water-maze task. The vertical axis shows probability of remaining a swimmer (i.e. not having found the platform) against pathlength (i.e. distance swum) for different treatment groups.

Figure 5:
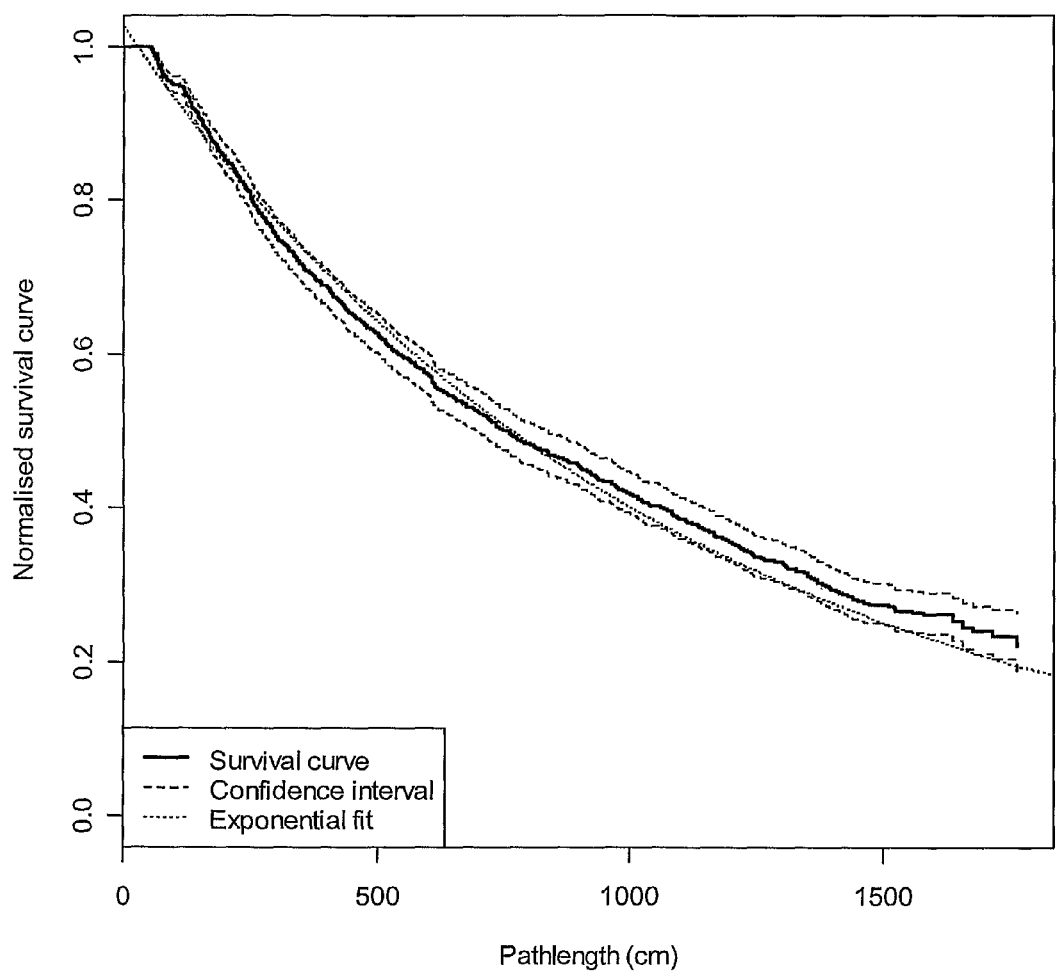

FIG. 5: After treatment effects have been normalised using the parameters determined from Cox proportional hazard analysis, the residual distribution shows that the pathlength is very close to a predicted underlying exponential function.

Figure 6:
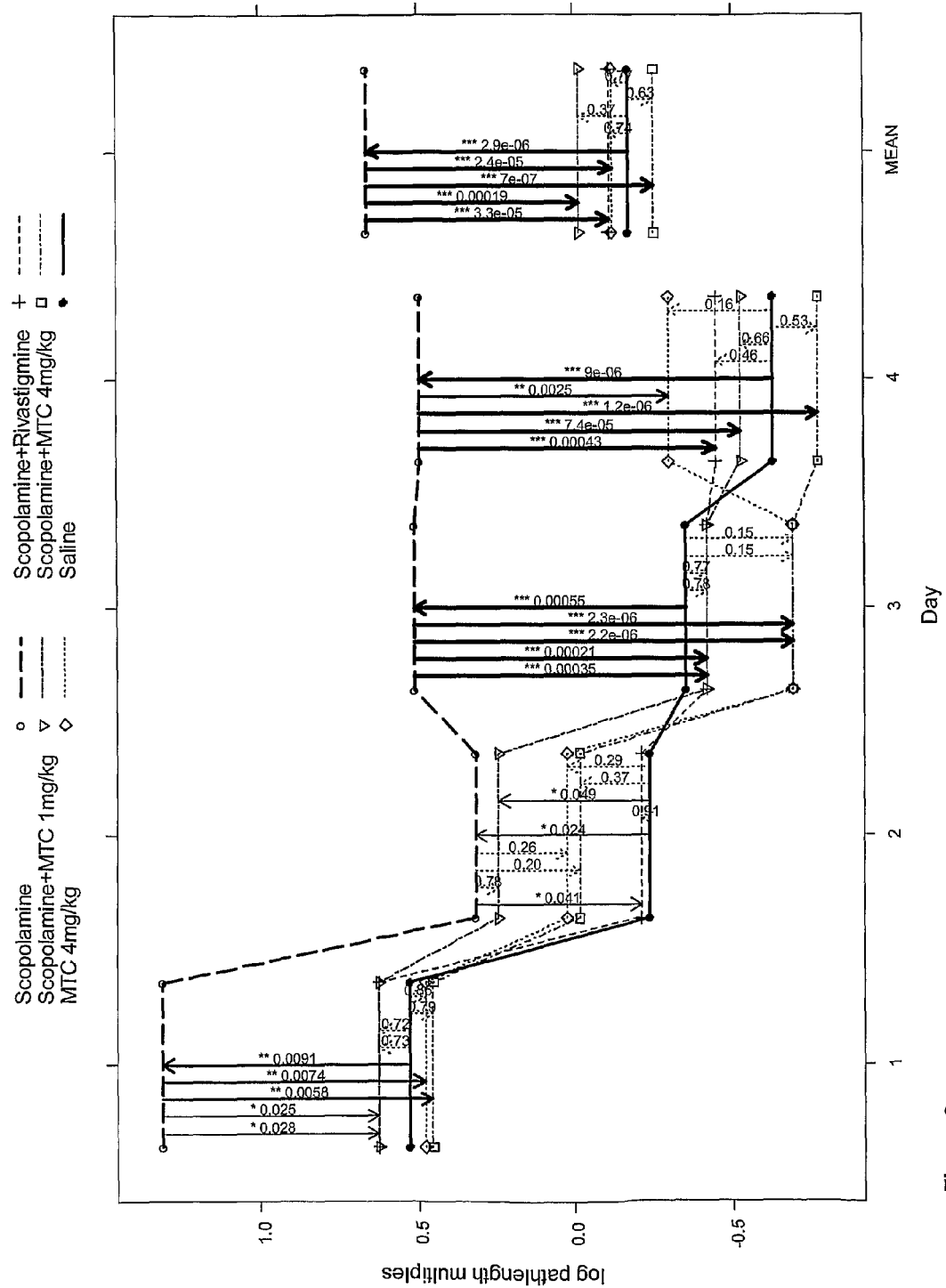

FIG. 6: In the graph, a measure representing pathlength is plotted for each treatment group over days, with the overall treatment differences (average over days) being shown above the heading "MEAN". The p values corresponding to differences between certain treatment groups are given.

Figure 7:
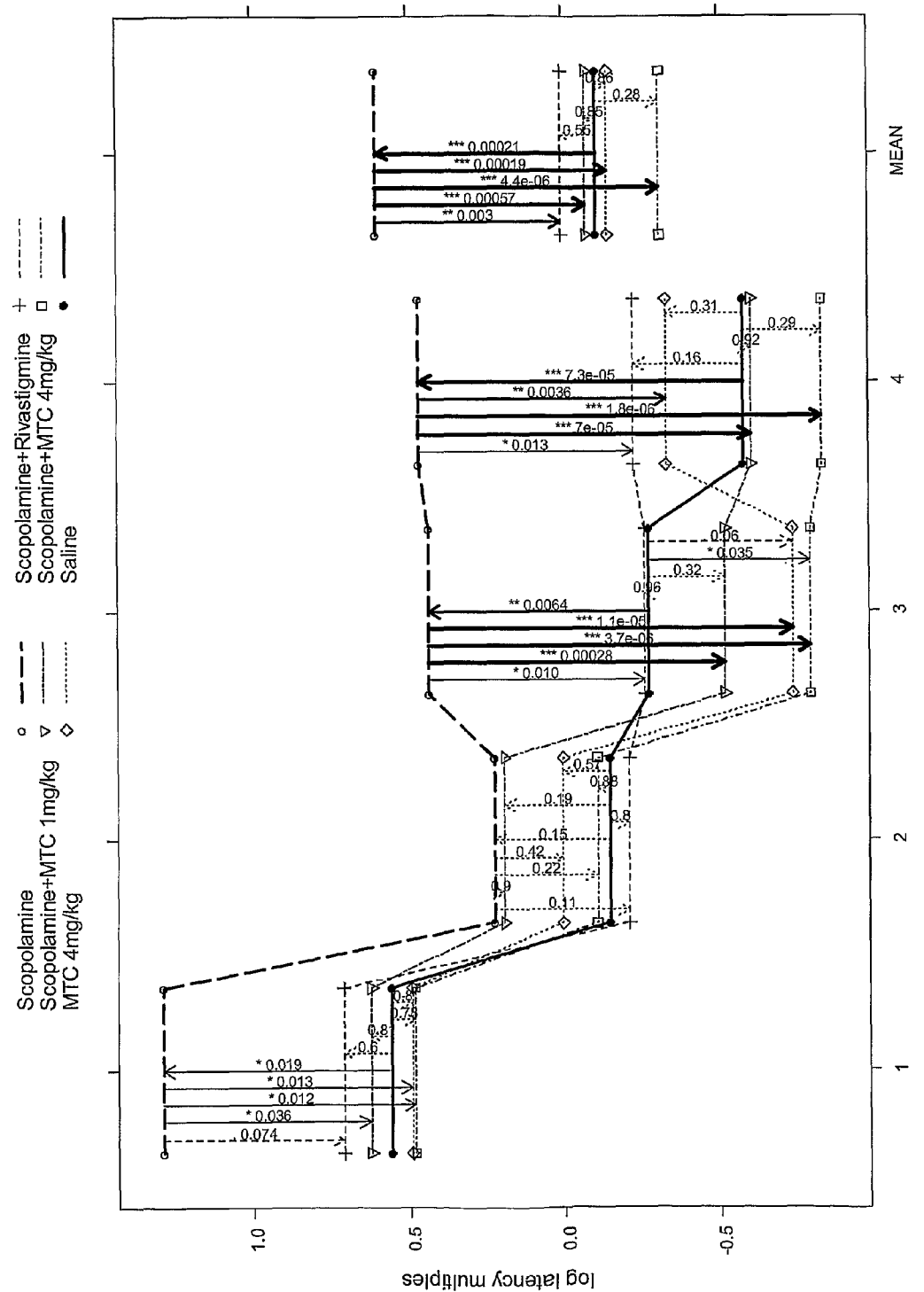

FIG. 7: A measure representing latency is plotted for each treatment group over days, with the overall treatment differences (average over days) being shown above the heading "MEAN". The p-values corresponding to differences between certain treatment groups are given.

Figure 8:
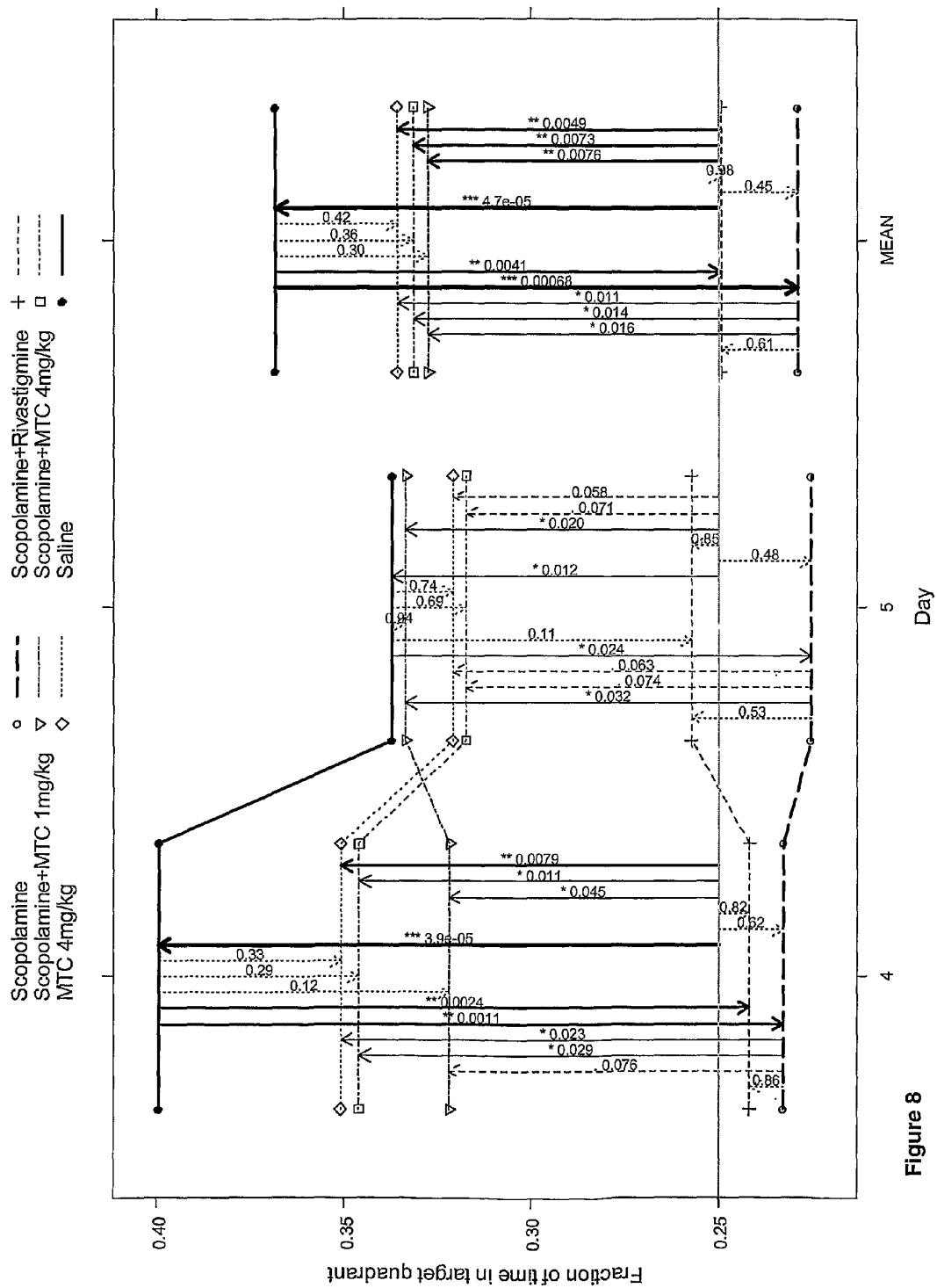

FIG. 8: Fraction of time spent in target quadrant after removal of the platform. Days 4 and 5 represent performance 1.5 hours and 24 hours after completion of the learning phase respectively. p-values for the statistical significance of the difference between treatment groups and the chance level of 25% are shown both day-wise and overall on an average over days ("MEAN").

Figure 9:
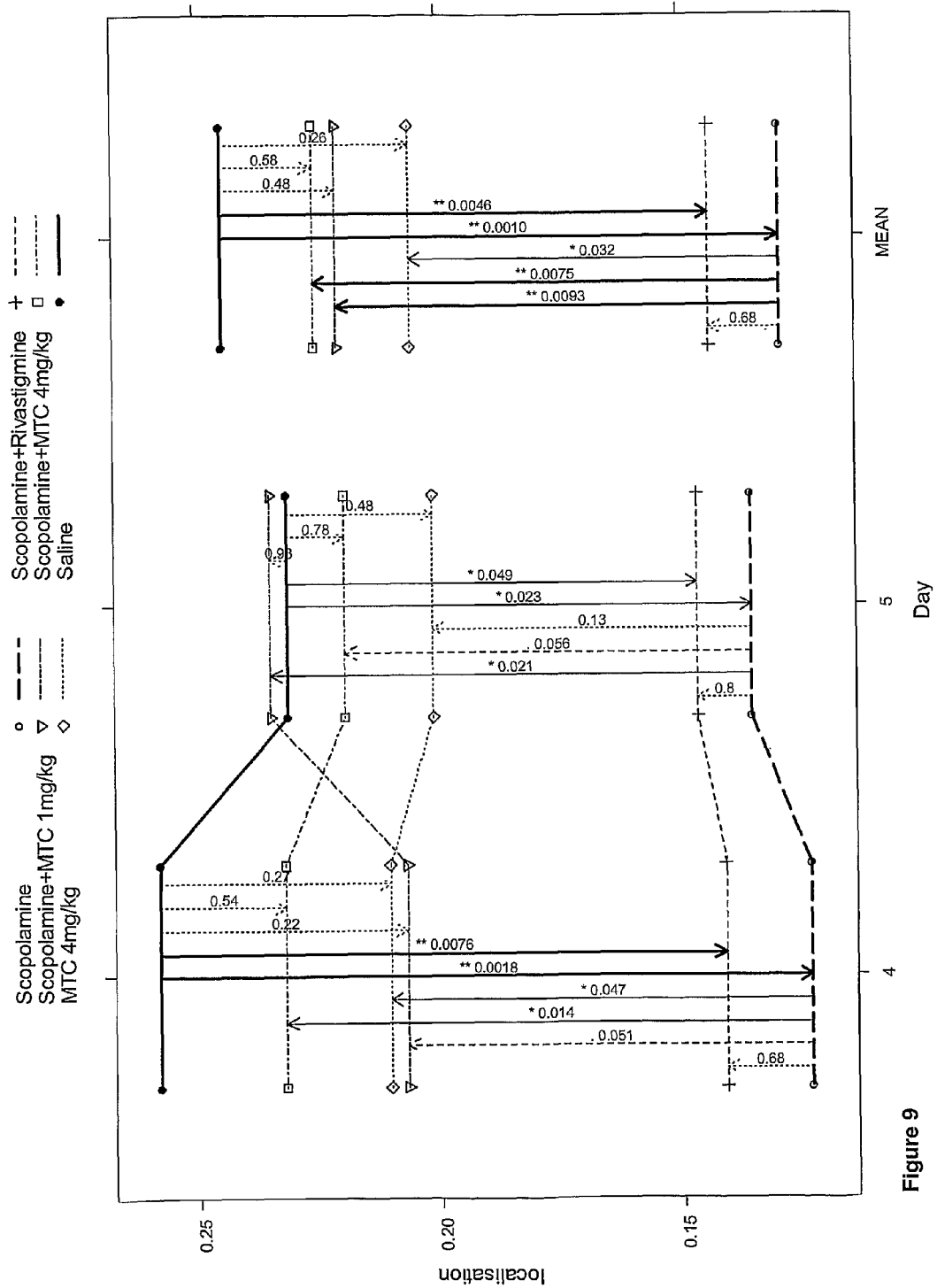

FIG. 9: Calculated "localisation", a composite parameter based on: number of visits to the previous platform location; number of visits to the surrounding area defined as an area twice the diameter of the platform; time in this surrounding area; and time in target quadrant. Day 4 represents performance 1.5 hours after completion of the learning phase. Day 5 represents 24 hours after completion of the learning phase. p-values for the statistical significance of differences between treatment groups both day-wise and overall on an average over days ("MEAN") are shown.

Figure 10:
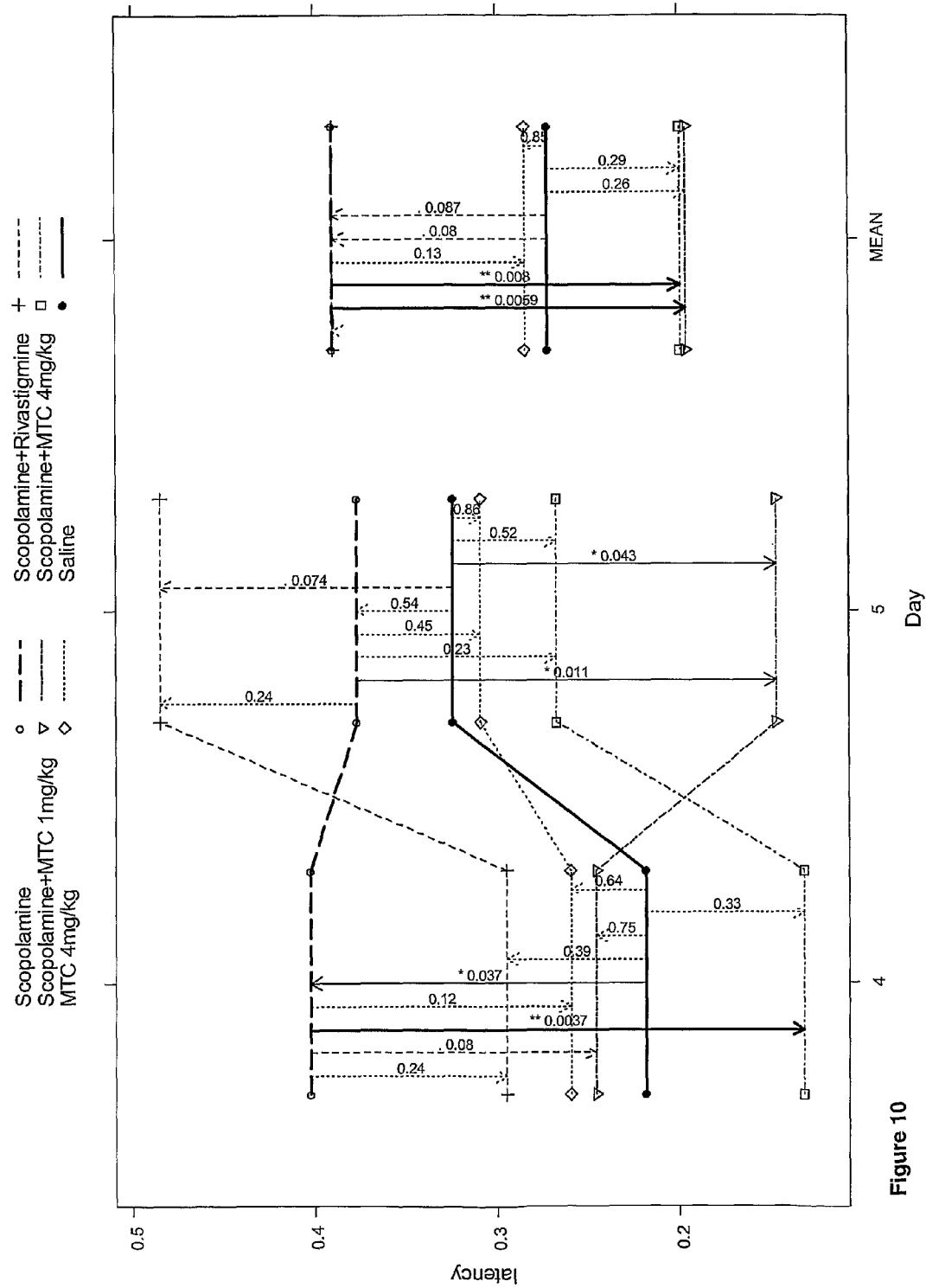

FIG. 10: Calculated "latency", a composite parameter based on the time taken to attain the platform area and the time taken to attain an area defined as twice the platform diameter. Day 4 represents performance 1.5 hours after completion of the learning phase. Day 5 represents 24 hours after completion of the learning phase. p-values for the statistical significance of differences between treatment groups both day-wise and overall on an average over days ("MEAN") are shown.

Figure 11:
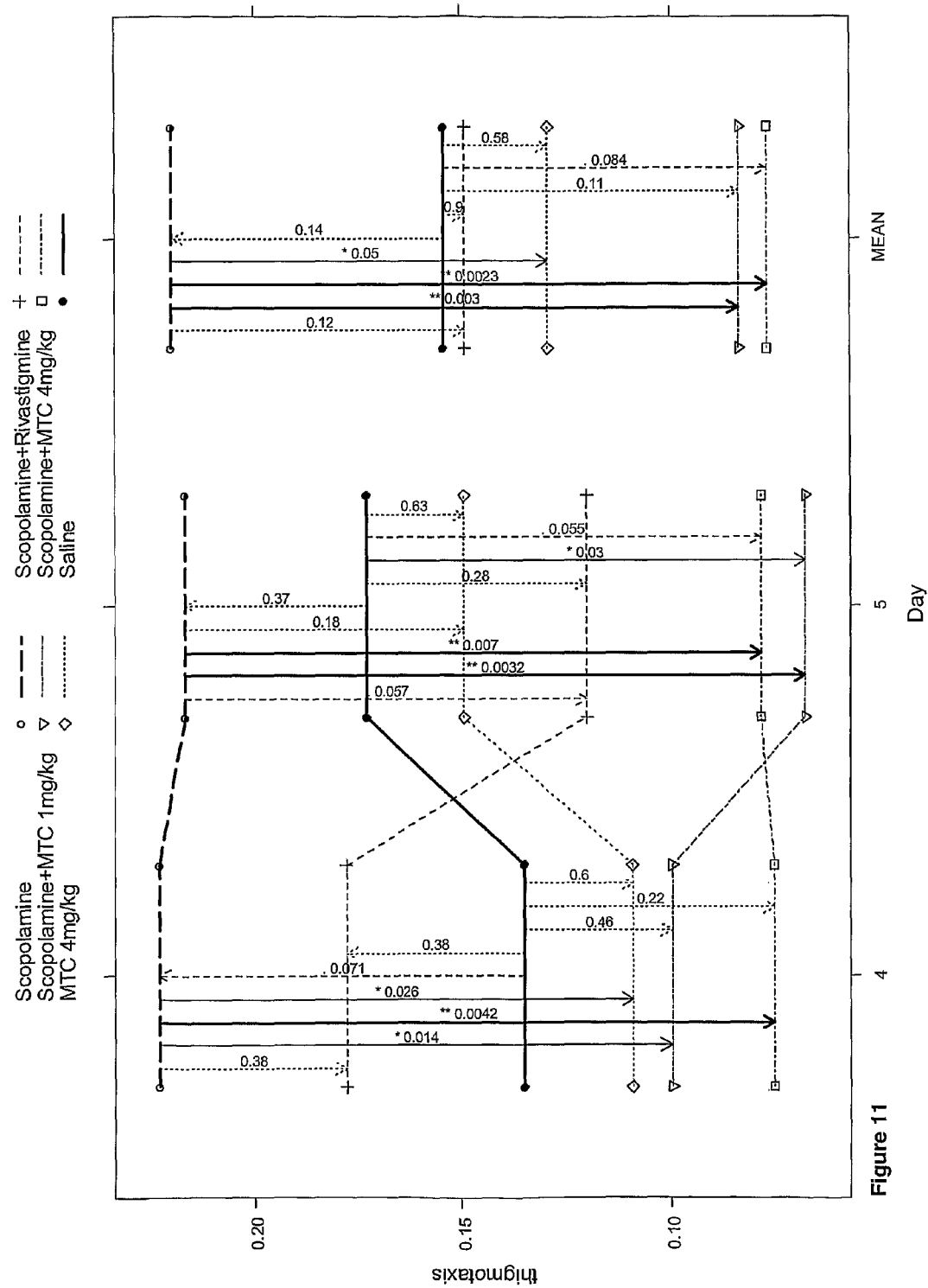

FIG. 11: Fraction of time spent in the thigmotaxis zone (defined as the outer 10% of the pool area) on Day 4 (1.5 hr after completion of learning phase) and on Day 5 (24 hr after completion of learning phase). p-values for the statistical significance of differences between treatment groups both day-wise and overall on an average over days ("MEAN") are shown. An animal showing less thigmotaxic behaviour is less anxious.

Figure 12:
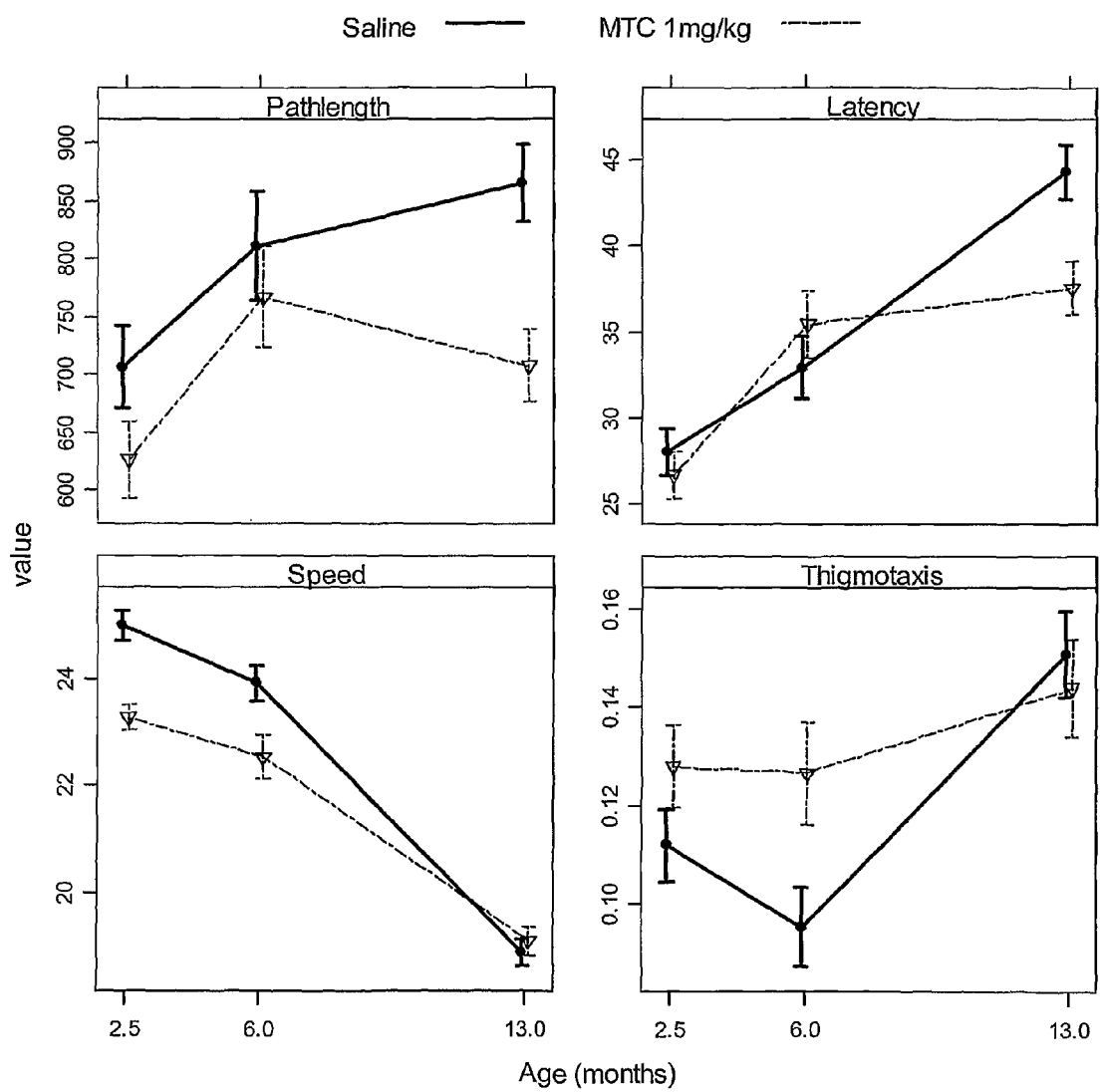

FIG. 12: Overall changes in pathlength (cm), latency (seconds), speed (cm/s) and thigmotaxis (fraction of time spent in zone) with age (months). Data have been averaged over the 4 days of the learning phase of the experiment, ignoring ceiling effects in pathlength for those mice not attaining the platform. Standard error bars are given.

Figure 13:
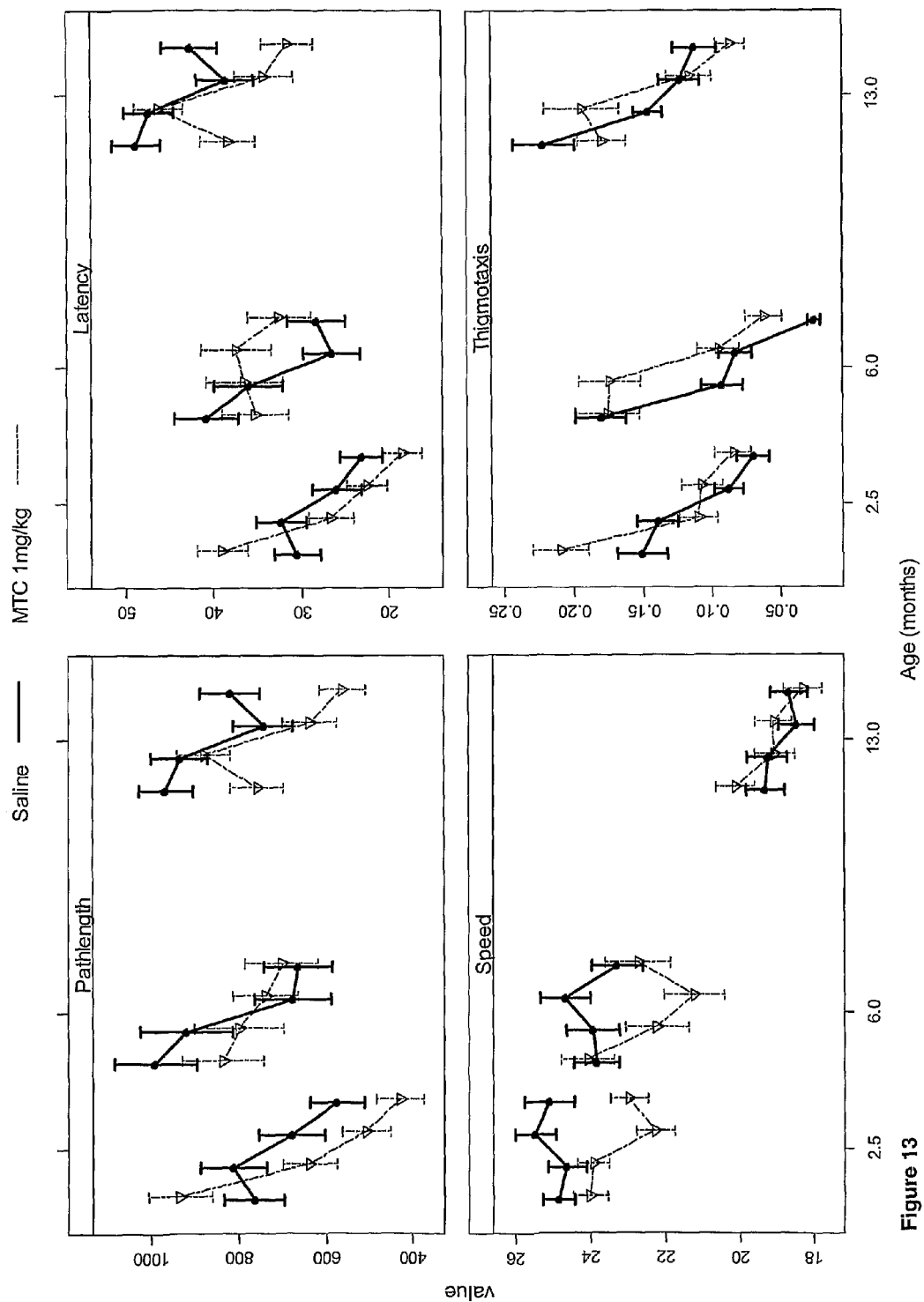

FIG. 13: Variation in day-wise averages of pathlength (cm), latency (seconds), speed (cm/s) and thigmotaxis (fraction of time in zone) with age (months). Ceiling effects in pathlength for those mice not attaining the platform are ignored. Standard error bars are given.

Figure 14:
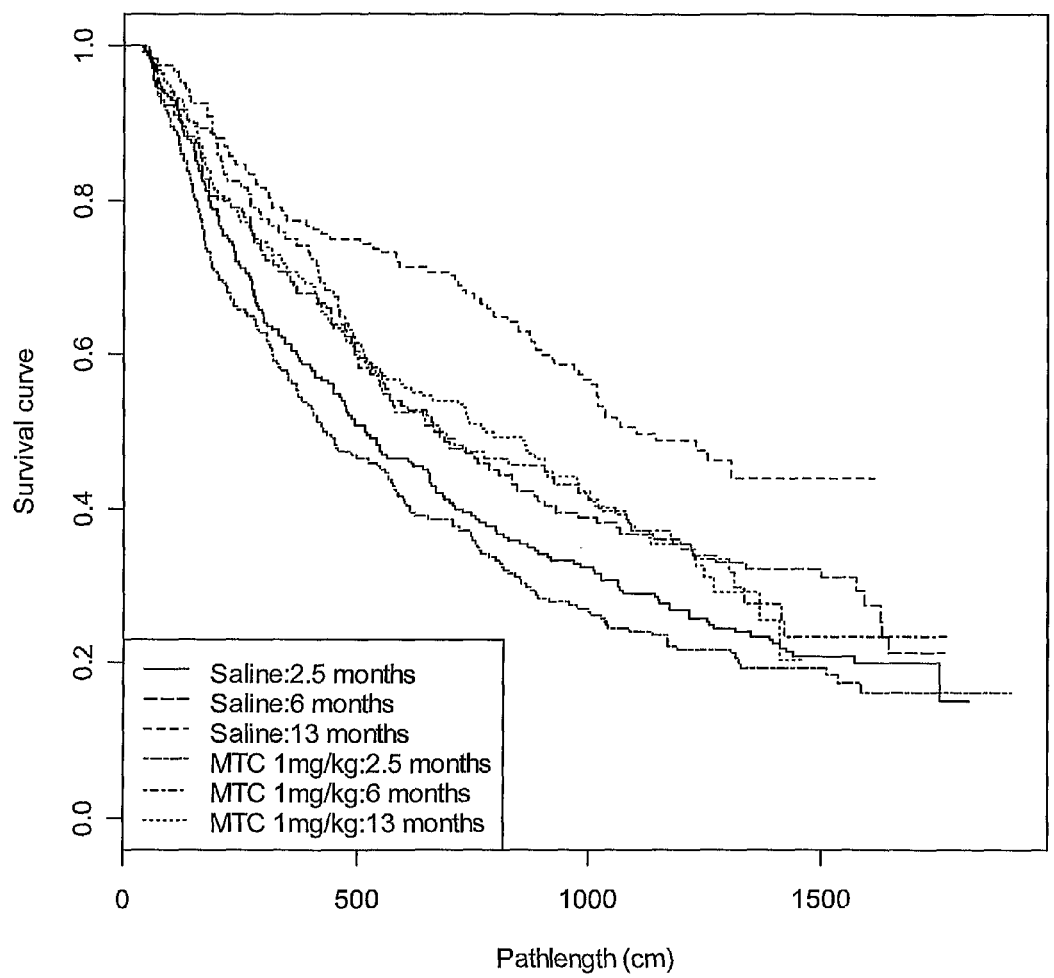

FIG. 14: Survival plot for swim status of animals in learning-phase of water-maze task. The vertical axis shows probability of remaining a swimmer (i.e. not having found the platform) against pathlength (i.e. distance swum) for different treatment groups.

Figure 15:
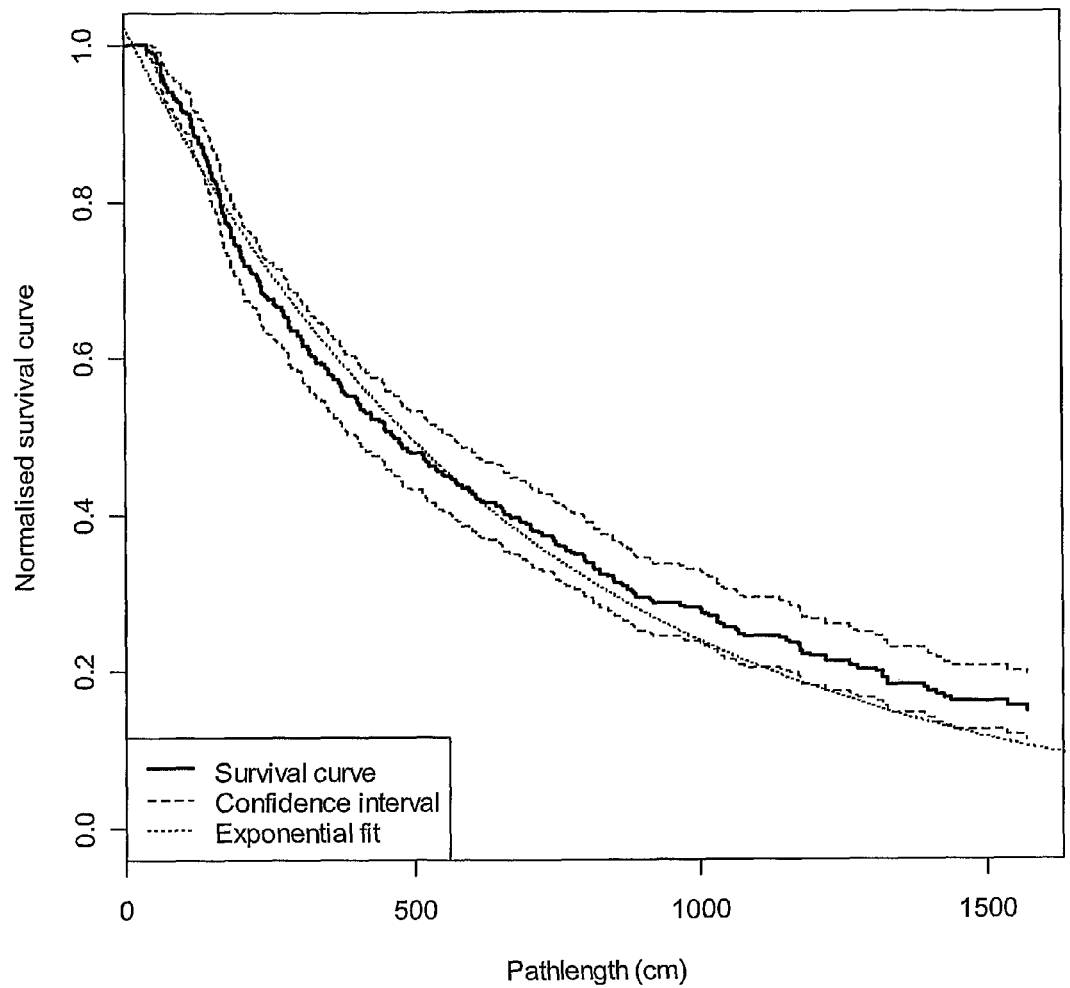

FIG. 15: After treatment effects have been normalised using the parameters determined from Cox proportional hazard analysis, the residual distribution shows that the pathlength is very close to a predicted underlying exponential function.

Figure 16:
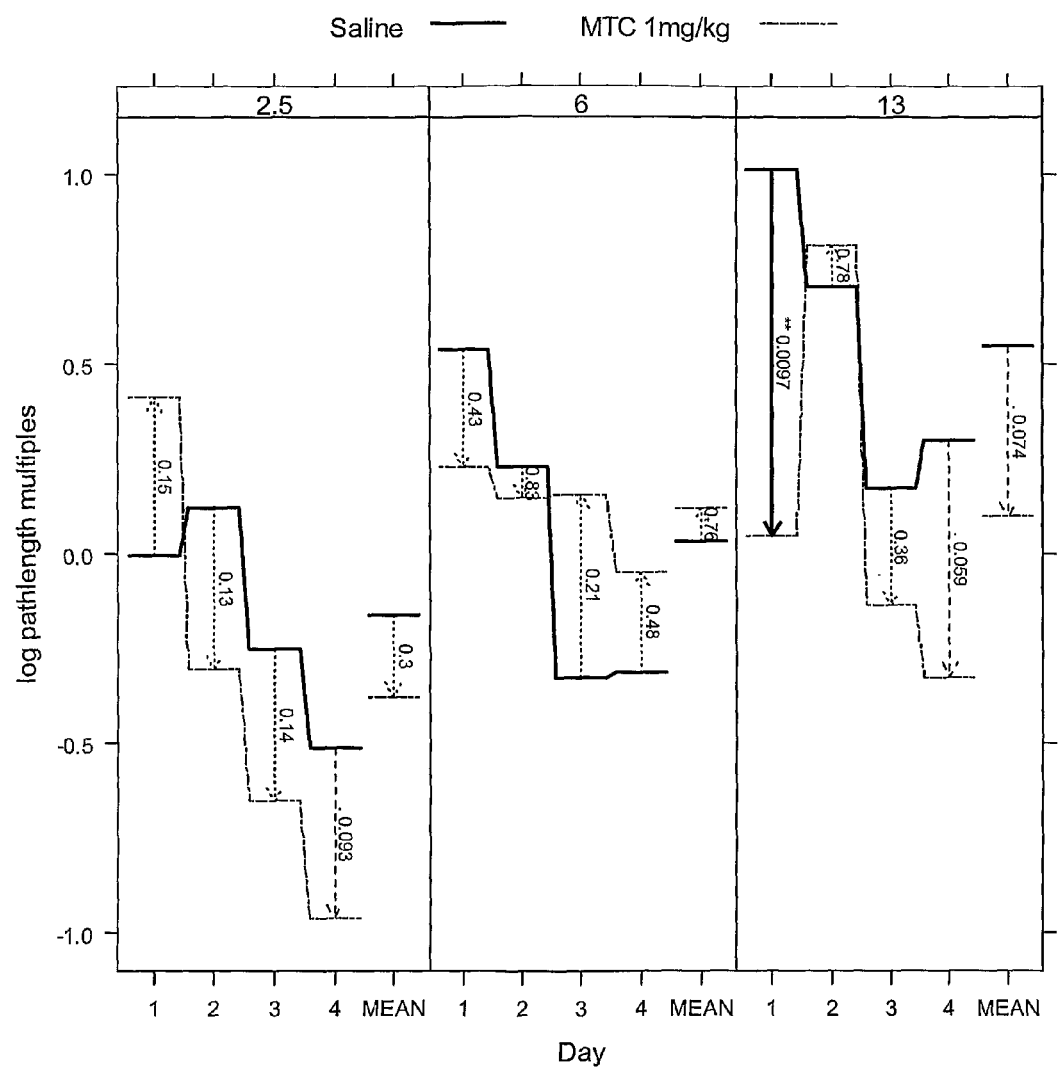

FIG. 16: In the graph, a measure representing pathlength is plotted for each treatment group over age, for each day and for an average over days. The p values corresponding to differences between the treatment groups are given.

Figure 17:
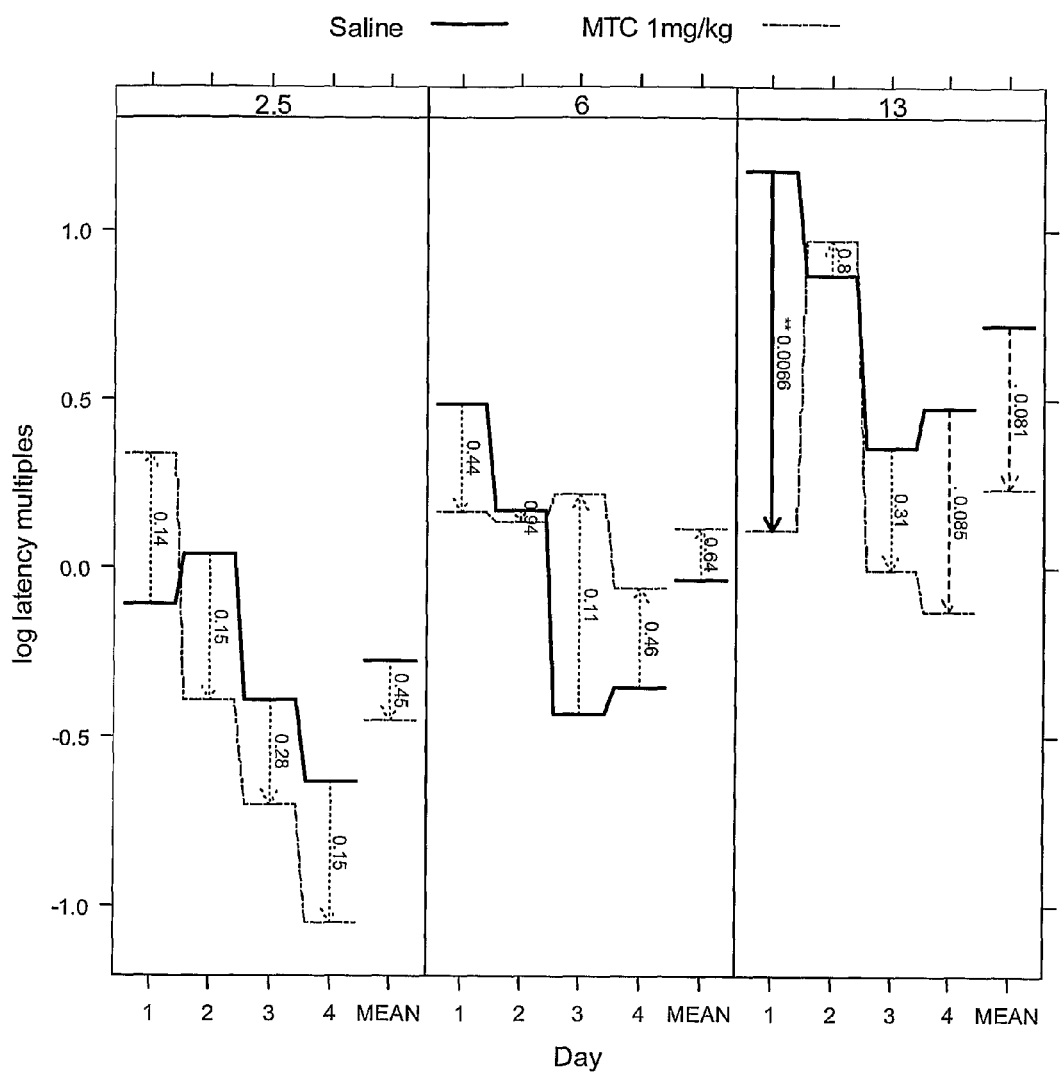

FIG. 17: In the graph, a measure representing latency is plotted for each treatment group over age, for each day and for an average over days. The p values corresponding to differences between the treatment groups are given.

Figure 18:
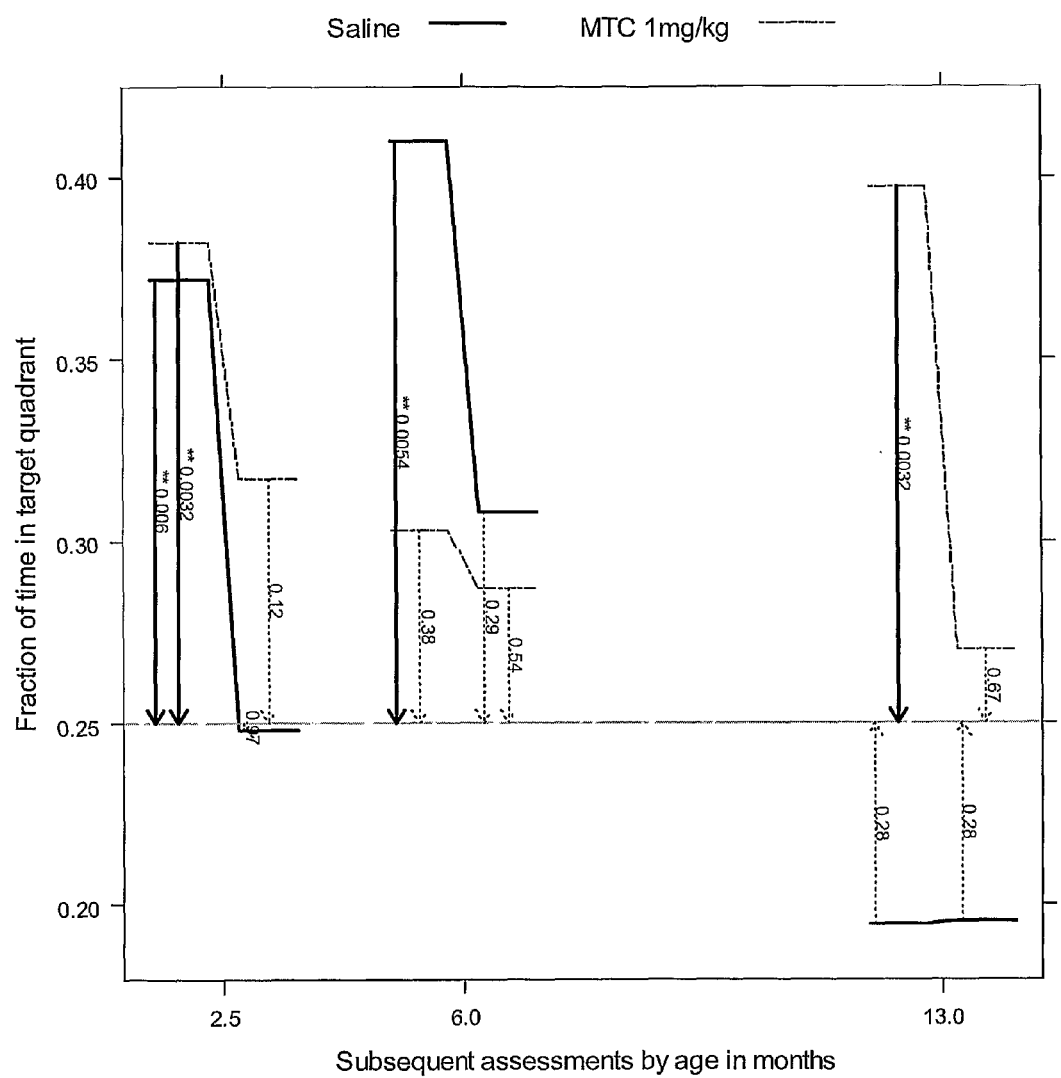

FIG. 18: Fraction of time spent in target quadrant after removal of the platform. Days 4 and 5 are shown for each age group (2.5, 6 and 13 months) and represent performance 1.5 hours and 24 hours after completion of the learning phase, respectively. p-values for the statistical significance of the difference between treatment groups and the chance level of 25% are shown.

Figure 19:
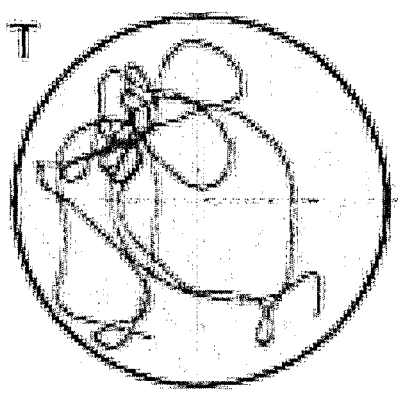
Figure 19:
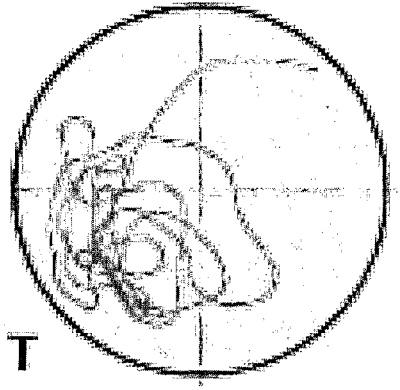
Figure 19:
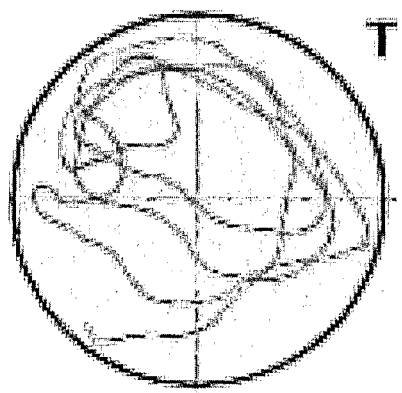
Figure 19:
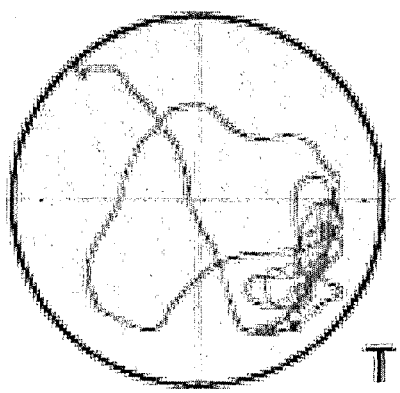

FIG. 19: Representative swim paths of a mouse in different age and treatment groups (T identifies the target quadrant).

Figure 20:
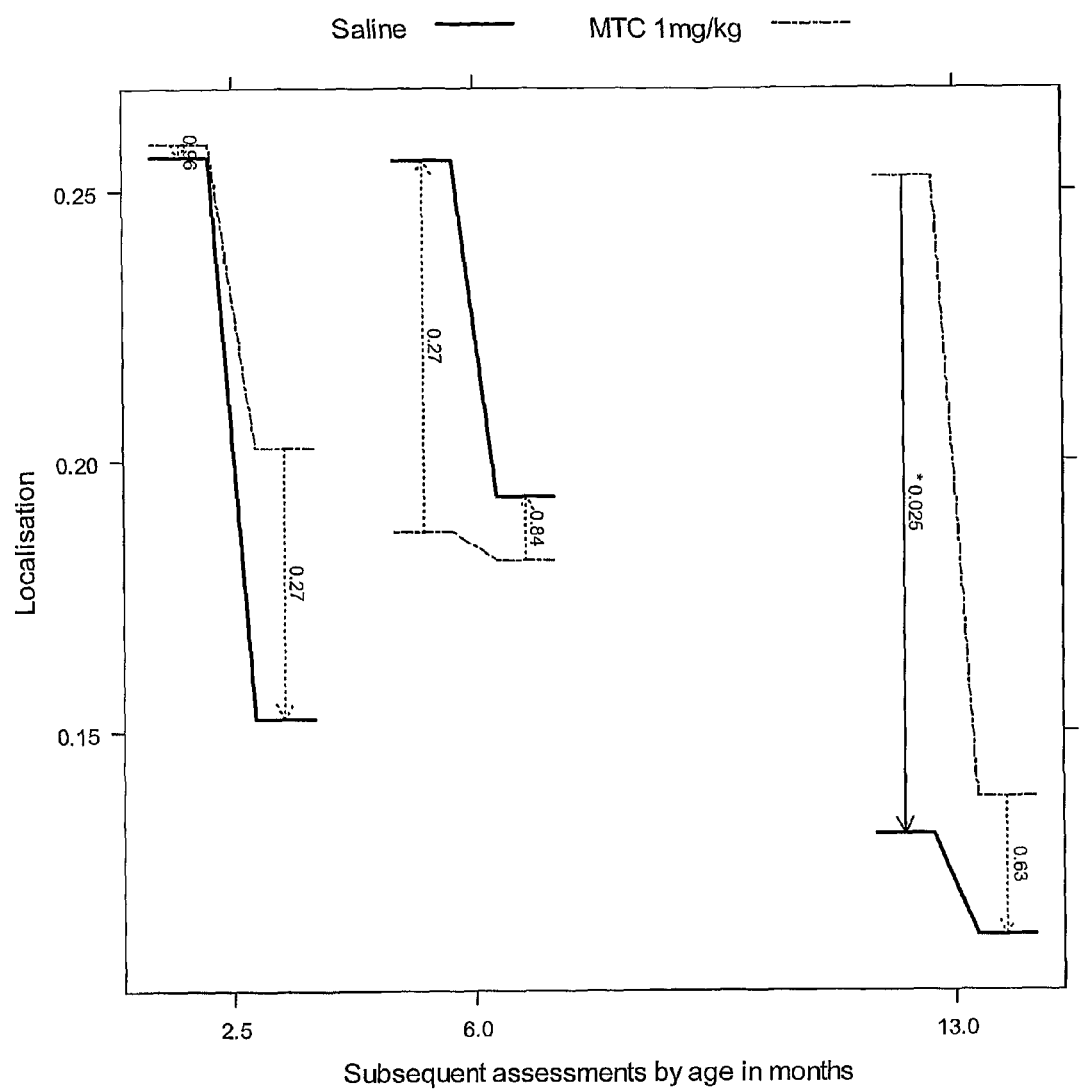

FIG. 20: Calculated "localisation", a composite parameter based on: number of visits to the previous platform location; number of visits to the surrounding area defined as an area twice the diameter of the platform; time in this surrounding area; and time in target quadrant. Two assessment time points (1.5 hours and 24 hours after completion of the learning phase) are shown for each age-group (2.5, 6 and 13 months). The p-values given are for the statistical significance of day-wise differences.

Figure 21:
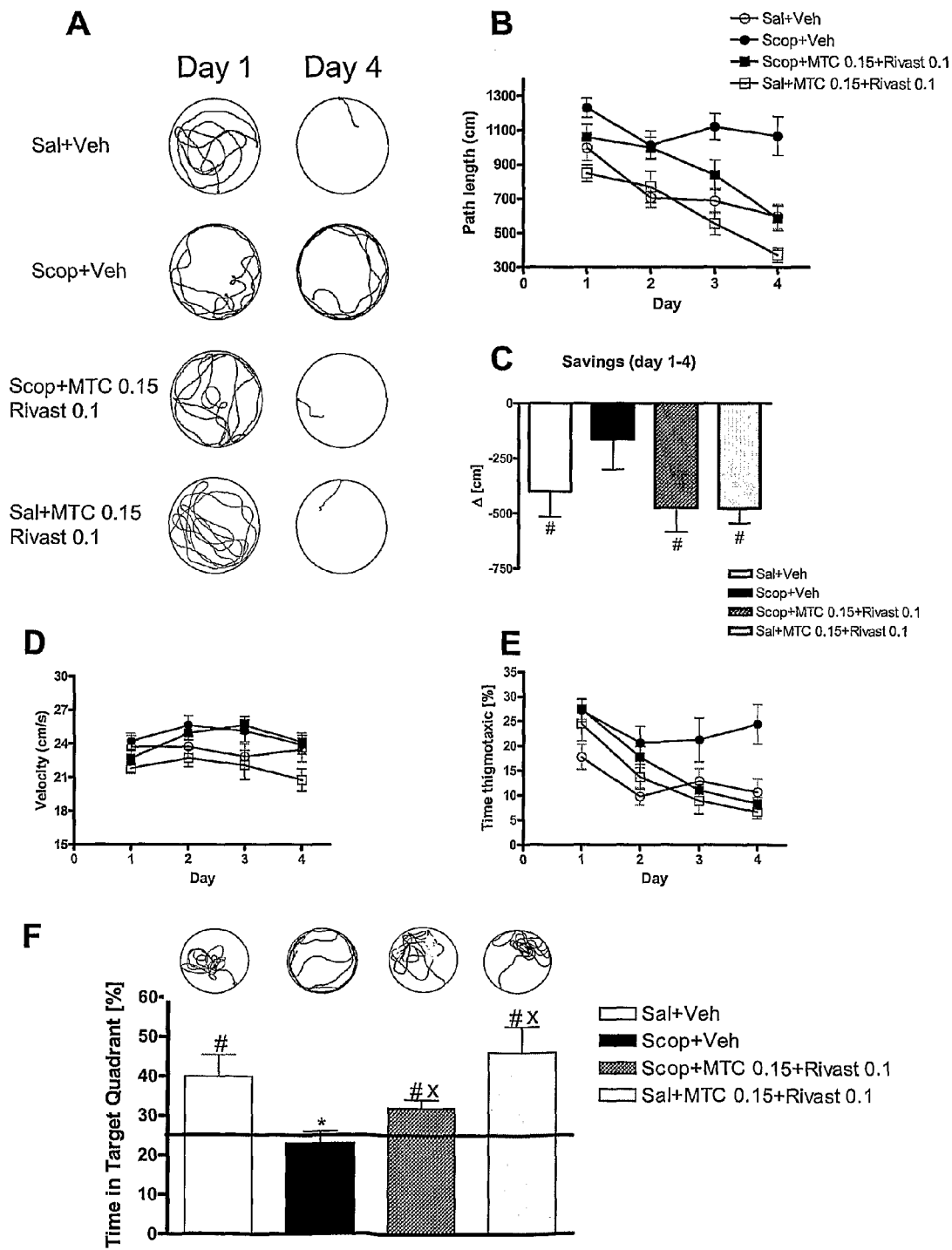

FIG. 21: Co-administration of sub-effective doses of drugs compared to controls: the figures shows comparison of the four groups on the measure of path length (A and B); reduction in path length (C); swim speed (D) thigmotaxis (E) and spatial memory (F).

EXAMPLES

Example 1

The Effect of MTC and Scopolamine in Cognition

1) Aim and Background to the Study

The aim was to investigate if MTC can reverse cognitive deficits induced by the acute injections of the muscarinic antagonist scopolamine. Scopolamine-induced memory impairments are widely used to mimic amnesia, such as may be found in MCI or dementia.

Scopolamine-Induced Memory Impairment

Pharmacologic blockade of central muscarinic receptors produces a short-term amnestic response in a wide variety of animal models performing a variety of tasks challenging learning and recall (Flood, T. and A. Cherkin, Scopolamine effects on memory retention on mice: A model of dementia? Behav. Neurol. Biol. 45 (1981), pp. 169-184). Scopolamine is particularly effective when administered just before task training.

Morris Water Maze

One of the most widely employed paradigms used to assess working memory in rodents is the Morris water maze spatial navigational task (Morris, R. Development of a water-maze procedure for studying spatial learning in rat. J. Neurosci. Methods 11 (1984), pp. 47-60).

Administration of low doses of scopolamine have been shown to effectively interfere with task performance. The effects of scopolamine on maze performance can be reversed by the administration of classical (centrally-acting) muscarinic receptor agonists, particularly inhibitors of acetylcholinesterase (Shannon, H. E. and Peters S. C. A comparison of effects of cholinergic and dopaminergic agents on scopolamine-induced hyperactivity in mice. J. Pharmacol. Exp. Ther. 255 (1990), pp. 549-553).

2) Materials and Methods

Test Compounds

The following test compounds were made up in vehicle consisting of saline (0.9% NaCl): MTC (Simpsons, UK); scopolamine hydrobromide, a non-specific muscarinic antagonist purchased from Sigma; and rivastigmine tartrate, used as a positive control.

Rivastigmine is an acetylcholinesterase inhibitor sold by Novartis as Exelon®. Donepezil, galantamine, and rivastigmine are similar inhibitors that have all been approved in many countries for the treatment of Alzheimer's disease, even though their efficacy, in the short term, is modest, symptomatic, and evident only in a subgroup of patients.

Female, NMRI mice aged 3-4 months were from Harlan, UK.

Mice were group housed (7-9 per cage) and maintained with light from 7 am-7 pm and experiments carried out in the light phase. There were 82 mice in total, of which 12 were excluded from the study for circling behaviour during the water maze test. They were separated into 6 groups to receive drug administrations as follows:

| Group | Number of mice | Treatment 1 | Treatment 2 |
| --- | --- | --- | --- |
| 1 | 13 | Saline | Saline |
| 2 | 12 | Scopolamine (0.5 mg/kg) | MTC (1 mg/kg) |
| 3 | 11 | Scopolamine (0.5 mg/kg) | MTC (4 mg/kg) |
| 4 | 11 | Saline | MTC (4 mg/kg) |
| 5 | 12 | Scopolamine (0.5 mg/kg) | Saline |
| 6 | 11 | Scopolamine (0.5 mg/kg) | Rivastigmine (0.5 mg/kg) |

Animals received two injections, the first (saline or scopolamine) 35 minutes prior to test and the second (saline, rivastigmine or one of two different doses of MTC) 5 minutes after the first injection so that MTC was always injected 30 min prior to test. The injection volume for drugs was 0.2 ml per 30 g animal weight and they were injected intraperitoneally. The doses were as indicated above.

Behavioural testing was undertaken using the Morris water maze spatial navigational task (Morris, 1984). The water maze consisted of a water-filled pool (1.5 m diameter; 20±2° C.) in which a platform submerged 1 cm below water surface was the only means of escape. Mice were released from 4 cardinal sites (South, West, North and East) facing the wall of the pool in random fashion and thus had to acquire spatial knowledge of the exact platform location by spatial mapping procedures using distal cues.

Each animal was given 6 trials/day and was allowed to swim for a maximum time of 60 seconds and stay 30 seconds on the platform. If the animal did not find the platform during the period time allotted (60 seconds) it was guided by the experimenter to the platform. An inter-trial interval of 10-20 minutes was given. The animals were trained for 4 consecutive days and received probe trials (free swim for 60 seconds without platform in the pool) approximately 1.5 and 24 hours post-training to test short and long-term memory, respectively. The behaviour of animals was recorded via an overhead camera and data transmitted to the PC for online storage and analysis (EthoVision basic version 3.0.8. Noldus Information Technology, Netherlands). The software was set up as follows: pool area, 150 cm diameter (240 pixels); thigmotaxis zone, 141 cm diameter (the outer 10% of pool area; 225 pixels); platform, 12 cm diameter (19 pixels) and counter area, 24 cm diameter (38 pixels).

3) Results

The learning phase results are presented as two analyses, conventional and advanced. The conventional analysis follows the statistical methodology commonly practiced in the field of behavioural neuropharmacology, making use of analysis of variance (ANOVA) which relies on the assumption that least-squares linear regression analysis of normally distributed data is appropriate. The advanced analysis develops a model based on the inherent properties of the data, and performs corresponding statistical comparisons. Broadly similar conclusions are reached, but the methodology of the advanced analysis is statistically more robust.

3.1—Learning Phase—Conventional Analysis

The length of the swim path over four days of training was pooled as a daily average per group and the results are shown in FIG. 1.

The mice treated with scopolamine, followed by saline, did not learn the task; the swim path length did not decrease over the 4 days, confirming a drug-induced learning impairment; there was no day effect ($F(3,33)=2.004$; $p=0.1325$) for the scopolamine group. An analysis by two-way ANOVA, with drug treatment and day as factors, yielded an overall effect of drug ($F(5,192)=9.305$; $p<0.0001$). This effect was due mainly to the [saline+scopolamine] group, since omission of this group from the analysis confirmed that all groups presented with excellent learning curves and showed a strong day effect ($F(3,159)=36.97$; $p<0.0001$) and no drug effect ($F<1$). This indicates that both MTC and rivastigmine reversed the learning-deficit induced by scopolamine. Furthermore, in contradiction to the findings of Callaway et al. (2004), MTC (4 mg/kg) had no effect on this spatial reference memory paradigm when given alone i.e. to otherwise unimpaired animals.

The two doses of MTC both completely reversed the scopolamine-induced learning deficit (1 mg/kg ($F(1,66)=13.65$; $p=0.0013$); 4 mg/kg ($F(1,63)=22.18$; $p=0.0001$) relative to the [saline+scopolamine] group). Rivastigmine also completely reversed the scopolamine-induced learning deficit ($F(1,63)=17.55$; $p=0.0004$).

The wall-hugging (thigmotaxis) behaviour of the mice is depicted in FIG. 2. Thigmotaxis is generally taken as an index of anxiety and is defined as the fraction of time spent in the outer 10% of the pool. Usually during the first day of training, thigmotaxis is high as the animal is naïve to the task and it has a natural tendency to seek to escape along the edge of the pool.

A two-way ANOVA analysis of the thigmotaxis data, with drug treatment and day as factors, revealed main effects of drug ($F(5,192)=5.954$; $p=0.0001$) and day ($F(3,192)=51.70$; $p<0.0001$). The group treated with [scopolamine+saline], showed the highest thigmotaxic activity over all the training phase and this did not decrease over the time. By contrast a decrease in thigmotaxis over days was observed in all the other groups. Therefore, both MTC and rivastigmine reversed the anxiety-inducing effects of scopolamine.

When the speed of the mice was analysed, a drug (F(5,192) =4.438; p=0.0016) and day (F(3,192)=6.261; p=0.0004) effect was found (FIG. 3). This was due mainly to the [scopolamine+rivastigmine] group, in which the speed decreased over the last two training days. This, however, did not affect their ability to learn and perform this spatial task. All other groups presented with similar swim speeds (F<1.4).

3.2—Learning Phase—Advanced Analysis

Pathlength data from all animals and treatments were analysed using a survival analysis paradigm, in which swim-distance is the variable considered as the survival parameter. That is, animals are considered to "survive" in the status of swimmer until they reach the platform. The results of this survival plot are shown in FIG. 4. As can be seen, the probability of an animal remaining a swimmer decreases to approximately 20% as the swim distance increases over 1500 cm. That is, animals have an increasing probability of finding the platform the greater the distance swum.

The treatment effects can be modelled formally using Cox proportional hazard methodology. Once the treatment effects have been accounted for by differing swim survival probabilities, the residual distribution is very close to that of an underlying exponential function, as shown in FIG. 5. The fact that the underlying distribution of pathlength data is exponential has the following behavioural interpretation. It appears that any given animal swims at random until there is moment when the animal recognises a spatial cue as to where the platform is. Once the animal has recognised this cue, it then swims directly for the platform. The differences in the parameters determined from the Cox proportional hazard analysis required to normalise the data reflect the differences associated with the various treatments which impact on the probability that at any given moment an animal will recognise a cue required to solve the problem of the water maze.

Recognising the underlying exponential distribution of the data, a statistical analysis was undertaken to determine treatment differences in terms of a logarithmic transform of pathlength. These are plotted in FIG. 6, with corresponding p-values for treatment condition differences on each day and on an average over days. As can be seen, all of the treatments have the effect of reversing the scopolamine-induced learning deficit by day 4. In particular, rivastigmine and MTC both reverse the deficit, returning the performance of animals to a level indistinguishable from controls. Therefore, MTC is at least equivalent to rivastigmine in reversing the scopolamine learning deficit. However, as can be seen from the plots in FIG. 6, there is no evidence that MTC improves learning over saline-treated mice. Therefore, in contradiction to Callaway et al. (2004), MTC does not improve learning in otherwise unimpaired mice.

An essentially identical pattern can be seen in the analysis of time-latency to find the platform, as shown in FIG. 7.

3.3 Memory Tests

Overall the behaviour on the probe trial on day 4 (i.e. memory tested at 1.5 hours) and on day 5 (i.e. memory tested at 24 hours) was essentially similar for the parameters described below. Therefore the conclusions are based on the pooled day 4 and day 5 data, although individual day-wise comparisons are shown in all the plots.

The primary parameter analysed was the proportion of time spent by the animal in the quadrant in which the platform had been located during the learning phase of the experiment. The analysis is shown in FIG. 8. The model used for statistical analysis was a linear mixed-effects model, allowing for treatment and day interaction and per-subject variability (i.e. some mice may inherently perform differently in the memory task irrespective of treatment grouping). Scopolamine-treated mice were found to perform no better than chance (i.e. the time spent in the target quadrant was not significantly different from 25%). Rivastigmine treatment did not reverse the scopolamine deficit. By contrast, MTC at doses of 1 mg/kg and 4 mg/kg reversed the memory defect produced by scopolamine, and returned animals to levels of performance indistinguishable from saline-treated controls. MTC alone had no discernible effect on memory relative to saline-treated control mice.

A composite parameter, "localisation" was calculated, based on: the number of visits to the area in which the platform was located; number of visits to the surrounding area, defined as an area twice the diameter of the platform; time in this surrounding area; and time in target quadrant. These parameters are all similar in principle, in that all reflect the spatial accuracy of searching behaviour of the animal in the area in which the platform would have been expected from the learning phase. The results are shown in FIG. 9. MTC at doses 1 mg/kg and 4 mg/kg produced significant differences with respect to scopolamine. Thus the effect of MTC was to reverse the scopolamine deficit, whereas rivastigmine was not able to reverse the deficit. MTC alone had no discernible effect on spatial accuracy relative to saline-treated control animals.

A further parameter measured was "latency". This is a calculated composite parameter based on the latency to platform area and the latency to an area defined as twice the diameter of the platform. A shorter latency reflects accuracy in the time domain, and measures the length of time spent by the animal before it gets to the area where the platform would have been expected from the learning phase of the experiment. The results are shown in FIG. 10. When averaged over days, there is a highly significant difference between [scopolamine+MTC] and either scopolamine alone or [scopolamine+rivastigmine]. Although the deficit produced by scopolamine did not reach statistical significance relative to saline-treated animals, MTC was able to improve on the deficit significantly. Rivastigmine had no effect at all on the deficit. MTC alone had no discernible effect on temporal accuracy relative to saline-treated control animals.

Thigmotaxis was also examined during the memory phase of the experiment. Time spent in the thigmotaxis zone (defined as the outer 10% of the pool area) is a measure of anxiety. As can be seen from FIG. 11, scopolamine increased thigmotaxis relative to saline-treated controls (although this difference is not significant). However treatment with [scopolamine+MTC] and MTC alone significantly reduces the thigmotaxic behaviour when compared with the scopolamine-treated group. Mice treated with rivastigmine are not significantly different from either scopolamine or saline.

4 Conclusions from Example 1

The results confirm that a learning defect can be produced in mice by treatment with the cholinergic inhibitor scopolamine. As expected, rivastigmine, an acetylcholinesterase inhibitor which makes more acetylcholine available at nerve terminals, is able to reverse the learning defect produced by scopolamine. Rivastigmine is one of a widely used class of acetylcholinesterase inhibitor drugs used in the treatment of Alzheimer's disease and related dementias. Rivastigmine and related drugs are also used in the symptomatic treatment of MCI and can produce measurable benefits in this condition (see e.g. Feldman, H. H., Ferris, S., Winblad, B., Sfikas, N., Mancione, L., He, Y., Tekin, S., Burns, A., Cummings, J., del Ser, T., lnzitari, D., Orgogozo, J.-M., Sauer, H., Scheltens, P., Scarpini, E., Herrmann, N., Farlow, M., Potkin, S., Charles, N. C., Fox, N. C. & Lane, R. (2007) Effect of rivastigmine on delay to diagnosis of Alzheimer's disease from mild cognitive impairment: the InDDEx study. *Lancet Neurology* 6, 501-512; Grundman, M., Petersen, R. C., Ferris, S. H., Thomas, R. G., Aisen, P. S., Bennett, D. A., Foster, N. L., Jack, C. R., Jr, Galasko, D. R., Doody, R., Kaye, J., Sano, M., Mohs, R., Gauthier, S., Kim, H. T., Jin, S., Schultz, A. N., Schafer, K., Mulnard, R., van Dyck, C. H., Mintzer, J., Zamrini, E. Y., Cahn-Weiner, D. & Thal, L. J. (2004) Mild cognitive impairment can be distinguished from Alzheimer disease and normal aging for clinical trials. *Archives of Neurology* 61, 59-66.

Although rivastigmine reversed the learning deficit, this left no discernible trace in the memory of the animals. This can be seen from the analysis of the memory phase of the experiment looking at a range of parameters. The specific parameter, time in target quadrant, was not different from the 25% expected by chance seen either with scopolamine alone or after treatment with rivastigmine. A similar result was also seen using the broader composite parameter "localisation", which measures the spatial accuracy of the animal's behaviour in searching the area where the platform would have been expected. Rivastigmine did not reverse the loss of spatial accuracy produced by scopolamine. Likewise, rivastigmine did not reverse the loss of temporal accuracy, as measured by the composite parameter "latency". However, there was a suggestion that rivastigmine may have some calming influence in scopolamine-treated mice as determined by thigmotaxis behaviour.

The ability of rivastigmine to reverse the scopolamine-induced learning deficit is broadly consistent with the widely held notion that enhancement of cholinergic activity leads to improvements in attention during the learning phase of the task. That is, scopolamine-impaired mice are able to make better use of learning cues during the learning phase task, and this improvement persists from one day to the next, in that there is evidence of restoration of day-wise improvement after rivastigmine treatment which had been abolished by scopolamine. However, this effect of rivastigmine on learning leaves no apparent trace when tested specifically as an effect on memory. No evidence of memory for the platform location can be detected by any of a wide range of measures at either 1.5 or 24 hours after completion of learning. Therefore, rivastigmine does not enhance either short- or long-term memory, although it improves operational or performance memory during the acquisition phase of the task.

MTC had equivalent ability to restore performance during the learning phase of the experiment, in that the ability to reverse the scopolamine-induced deficit was indistinguishable from controls. The marked difference between MTC and rivastigmine emerged only during the memory phase of the experiment. Here, there was evidence of memory retention in a broad range of parameters. Specifically, the time spent in the target quadrant was significantly higher than the chance level, i.e. 25%, after treatment with either 1 mg/kg or 4 mg/kg. The broader localisation parameter also showed restoration of scopolamine-treated animals back to the control level of performance. Likewise, there was restoration of performance as measured by temporal accuracy. Finally, MTC produced a complete reversal of the severe impairment in ability to escape from the thigmotaxis zone produced by scopolamine.

Therefore, MTC is substantially better at reversing scopolamine-induced deficits than the cholinergic drug rivastigmine. Although broadly similar in terms of operational performance during the learning phase of the experiment, qualitative differences between rivastigmine and MTC emerge during the memory phase of the experiment. Whereas rivastigmine produced no evidence of memory retention of the task learned on any of the parameters measured, MTC showed evidence of memory retention. The MTC effect was not dose-dependent, in that there were no differences between MTC administered at 1 mg/kg or 4 mg/kg. There were also no significant time differences, in that evidence of memory retention could be demonstrated at both 1.5 and 24 hours after completion of the learning phase of the experiment.

It is unlikely in view of the results obtained that MTC acts via a cholinergic mechanism, since rivastigmine even at higher doses (data not shown) was not able to reverse the amnestic effect of scopolamine. Therefore, MTC acts via a qualitatively distinct mechanism to reverse the amnestic effect of scopolamine. The nature of this mechanism is unknown. Since the deficits seen in amnestic MCI are primarily in the domain of memory, it follows that MTC represents a candidate symptomatic treatment of MCI, particularly amnestic forms of MCI.

Rivastigmine is already used in the symptomatic treatment of MCI. Based on the results herein, the potential benefits of rivastigmine depend largely on effects on attention during task acquisition and not on memory, it follows that a drug such as MTC, which has effects which can be demonstrated both during task acquisition and on memory, would be expected to have superior efficacy over rivastigmine and other cholinergic-enhancing drugs in the treatment of amnestic MCI.

A recent concensus of international opinion has formulated two forms of MCI: amnestic and non-amnestic (Winblad, B., Palmer, K., Kivipelto, M., Jelic, V., Fratiglioni, L., Wahlund, L. O., Nordberg, A., Backman, L., Albert, M., Almkvist, O., Arai, H., Basun, H., Blennow, K., deLeon, M., De Carli, C., Erkinjuntti, T., Giacobini, E., Graff, C., Hardy, J., Jack, C., Jorm, A., Ritchie, K., van Duijn, C., Visser, P. & Petersen, R. C. (2004) Mild cognitive impairment—beyond controversies, towards a consensus: report of the International Working Group on Mild Cognitive Impairment. Journal of Internal Medicine 256, 240-246). Since operational deficits in non-cognitive domains are characteristic features of non-amnestic forms of MCI, it would be expected that MTC would represent a possible symptomatic treatment of non-amnestic forms of MCI. Specifically, MTC exerts a strong effect on thigmotaxis induced by scopolamine, which is generally taken as an index of anxiety. Rivastigmine however did not significantly exhibit this action. It is therefore likely that MTC could have beneficial effects on anxiety and other non-cognitive components of MCI, such as apathy, social withdrawal, loss of confidence and decision-making ability, as well as general social engagement.

Example 2

Effects of MTC on Water Maze Learning in Young and Aged NMRI Mice

1) Aim and Background to the Study

This study was designed to assess the effects of MTC on cognitive performance in a spatial reference learning and memory water maze task in NMRI mice at three different ages: 2-3, 6 and 13 months.

2) Methods

MTC (Simpsons, UK.) was dissolved in water. Female NMRI mice aged 2-3, 6 and 13 months were grouped after excluding any animals with abnormal swimming behaviour in the water maze task. MTC (1 mg/kg) was given intraperitoneally (i.p.) at 5 ml/kg. The number of animals at the end of study was as follows.

| Group | Age (months) | | |
|---|---|---|---|
| treatment | 2-3 | 6 | 13 |
| Saline | 10 | 6 | 7 |
| MTC (1 mg/kg) | 10 | 5 | 8 |

Behavioural testing was undertaken using the Morris water maze spatial navigational task (Morris, 1984) [as described in Example 1]. Mice were first habituated to the water maze before treatment and reference memory training. Mice were treated with MTC or vehicle 30 min before trial 1 of each daily session. Probe trials at the end of training assessed short-term and long-term memory (1.5 and 24 hours, respectively).

3 Results 3.1—Learning Phase—Conventional Analysis

FIGS. 12 and 13 show the path lengths, latency, speed and thigmotaxis across days and averaged over days for 2-3, 6 and 13-month old mice treated with saline or MTC (1 mg/kg). Aged mice were impaired in acquiring the reference memory water maze task. Examining only the data of the control (saline-treated) mice across the three age groups, 13-month old mice were impaired in the task relative to 2-3-month old mice. The older mice had longer path lengths across all days. Escape path lengths of 6-month old mice did not differ from those of either 2-3 or 13-month old mice.

MTC-treated, 13-month old mice had significantly shorter path lengths than 13-month old saline-treated mice. There was no significant difference between 2-3 month old MTC- and saline-treated mice, nor were the two MTC-treated groups different with respect to their escape path lengths. The 13-month old saline-treated group failed to improve (decreasing path lengths) across training days; the other groups had acquired the reference memory water maze task. All groups started at the same level as the path lengths in trial 1 did not differ.

The parameter of swim speed enabled motor performance to be assessed between the two age groups and to determine whether treatment with MTC yielded a motor effect on the task. Aged NMRI mice swam consistently slower than young mice, and this trait was independent of treatment.

In 13-month old mice, treatment with MTC did not alter swim speed; however, in 2-3 month old mice, those treated with MTC swam slower than age-matched controls during later training sessions.

The wall hugging behaviour (thigmotaxis) was evident in all mice at the start of training, but all groups showed a progressive decrease with successive training sessions.

Learning Phase—Advanced Analysis

Age-related changes were examined as in Example 1 in terms of the parameters pathlength, latency, speed and thigmotaxis, comparing animals treated with saline or MTC at 1 mg/kg. These are summarised in FIG. 12. Examining the crude means, there is a general deterioration in all four quantities with age. There is a beneficial treatment effect of MTC only in the 13-month mice, and only in respect of pathlength and latency. In the case of thigmotaxis, MTC causes a worsening at 2-3 months and 6 months, and has no benefit at 13 months.

The day-wise changes are plotted in FIG. 13. Younger mice improve more from day 1 to day 4 than older mice. It is unclear if MTC has any systematic impact on learning, although there is a suggestion that MTC improves the day-wise change in older mice.

As in Example 1, the pathlength and latency data were analysed using a survival model. As previously, the survival analysis calculates the probability of survival in the status of "swimmer" with respect to pathlength. The survival plots of the pathlength data are shown in FIG. 14. The 13-month-old saline-treated mice achieve only a 56% probability of finding the platform even after swimming 1500 cm. When the data were normalised to remove differences due to treatment, the residual distribution was very close to exponential (see FIG. 15). In younger mice, relatively more probability mass was found at low values of pathlength. This can be interpreted as follows. Older mice swim randomly until they detect a spatial cue, after which they swim directly to the platform. Younger mice are more likely to have already recognised a cue very early, and so spend less of the initial period swimming randomly before swimming directly to the platform.

The survival curves were parameterised using Cox proportional hazards estimates. These are shown as log pathlength multiples in FIG. 16. There is a strong aging effect seen in the saline-treated animals. There is no effect of MTC in younger mice. The effect of MTC on the 13-month mice is to substantially reduce the overall pathlength, bringing the performance of the older mice back to a level of performance observed with 6-month old mice. The overall difference approaches statistical significance ($p=0.074$). A similar analysis was undertaken for the latency data. The results for latency are essentially identical to those for pathlength (FIG. 17). As can be seen from FIGS. 16 and 17, the effects approach statistical significance for 13-month-old mice on day 4 for both pathlength and latency (p values 0.059 and 0.085 respectively).

3.2 Memory Tests

As in Example 1, animals were tested either at 1.5 hours after completion of the learning phase ("Day 4") or 24 hours after completion of the learning phase ("Day 5").

The first parameter analysed is the time spent in the target quadrant. This is shown for days 4 and 5 with and without treatment with MTC in FIG. 18. As in Example 1, the statistical analysis used a linear mixed-effects model, allowing for treatment and day interaction and per-subject variability (i.e. some mice may inherently perform better in the memory task irrespective of treatment grouping).

As can be seen in FIG. 18, saline-treated mice aged 2-3 months and 6 months were able to recall the platform location at 1.5 hours. At the 24-hour time point, their time in the target quadrant was not significantly different from the chance level (25%). It appears unlikely that this is due to failure to recall, as there was evidence of recall at 24 hours in Example 1. Rather, this may reflect extinction of the searching behaviour in the target quadrant due to presentation at 1.5 hours of no platform in the target quadrant. Younger animals may learn more efficiently that there is no longer a platform in what was previously the target quadrant, and modify their search strategy accordingly. There is no effect of MTC at 1.5 hours in the 2-3 month mice (i.e. they do spend significantly more than 25% time in the target quadrant, like the saline group). In the 6-month old mice, MTC appears to produce an impairment of recall at this time point.

The 13-month saline treated mice show complete incompetence at both 1.5 and 24 hours. Treatment with MTC restores recall at 1.5 hours. It is not possible to determine from this experiment whether MTC failed to restore recall at 24 hours, or whether MTC produced more efficient extinction in the 13-month mice comparable to the saline-treated 2-3 month and 6-month old mice. Representative swim paths given in FIG. 19 show complete restitution of swim path directionality in a 13-month old mouse after treatment with MTC.

An analysis of localisation was undertaken, which is shown in FIG. 20. As in Example 1, "localisation" is a composite parameter reflecting spatial accuracy of search, calculated from: number of visits to the previous platform location; number of visits to the surrounding area defined as an area twice the diameter of the platform; time in this surrounding area; and time in target quadrant. As can be seen from FIG. 20, localisation is significantly improved by MTC in 13-month old mice at the 1.5 hour probe time. There are no other significant differences, although directionally MTC appears to impair localisation at 1.5 hours in 6-month old mice.

A similar analysis of latency failed to reveal any significant effect of MTC.

4 Conclusions from Example 2

This study has demonstrated an age-related spatial learning impairment in NMRI mice. This could be demonstrated from the data for both pathlength and latency. In the water maze reference memory task, 13-month old mice were unable to acquire the task. Furthermore, they showed no evidence of recall of the task at 1.5 hours after completion of the fourth day of learning. Therefore, by 13 months of age, NMRI mice show significant cognitive deficits. There is also some evidence of worsening of the non-cognitive parameter, thigmotaxis, with aging. This is taken to be a measure of anxiety. However, it was not possible to establish a model fit to this data set using the Cox proportional hazard parameterisation because between-subject variability overwhelmed the treatment effects in the analysis.

As in the Example 1 data, MTC showed no evidence of improvement in cognitive function in 2-3 month and 6-month old animals. Specifically, there was no improvement in the Cox proportional hazard parameterisation of pathlength or latency. Analysis of the thigmotaxis data was inconclusive. Similarly MTC failed to produce any evidence of improvement either at 1.5 or 24 hours in the memory phase of the experiment. These findings therefore reiterate those of Example 1 in failing to confirm the claims made by Callaway et al. (2004) and Riha et al. (2005) that MTC is able to improve memory function in the absence of pre-existing impairment.

Indeed, MTC impaired memory performance as measured by time in target quadrant and localisation at 1.5 hours in 6-month animals. This pattern is quite different from that observed at 2-3 months, when MTC had no effect at all on memory. There is also a suggestion in the data that MTC impaired learning as measured by the localisation parameter on days 4 and 5. Therefore, MTC is able to impair both learning and memory in adult mice.

The most striking effect of MTC was to produce an improvement in performance during the memory phase of the experiment. This could be seen particularly in the analysis of time in target quadrant. At 13 months, saline-treated animals were entirely incompetent and showed no evidence of having acquired target quadrant discrimination when tested only 1.5 hours after completion of learning. After treatment with MTC, time in target quadrant was indistinguishable from the performance seen at 2-3 months. Likewise, the composite parameter localisation showed essentially complete restoration of performance to that seen in saline-treated animals at 2-3 months of age at the 1.5-hour probe trial. Similarly, during the acquisition phase, the positive effects of MTC approached significance on day 4 in 13-month old mice for the parameters of pathlength and latency.

The age-related defects seen at 13 months in these animals can be taken as a model for MCI and age-related cognitive decline in humans. The ability of MTC to restore cognitive function in this model indicates that MTC may be useful therapeutically in the treatment of age-related cognitive decline and MCI syndromes.

Example 3

General Conclusions

As shown in Example 1, MTC can restore performance in a scopolamine-induced deficit model in both the learning phase and memory phase of the experiment. Additionally, MTC produced a complete reversal of the severe impairment in ability to escape from the thigmotaxis zone produced by scopolamine.

As shown in Example 2, MTC was able to produce an improvement in performance during the memory phase of the experiment. The age-related defects seen at 13 months in these animals can be taken as a model for MCI and age-related cognitive decline in humans.

The ability of MTC to restore cognitive function in these models indicates that MTC may be useful therapeutically in the treatment of age-related cognitive decline and MCI syndromes.

However in both Example 1 and Example 2, MTC showed no evidence of improvement in cognitive function in unimpaired animals.

It is claimed in two of the studies enumerated (Callaway et al., 2004; Riha et al., 2005) that memory consolidation can be improved in otherwise unimpaired animals. That is, the claim is made that otherwise unimpaired animals can be made to have better than normally expected memory by treatment with MTC.

The present findings therefore fail to confirm the claims made by Callaway et al. (2004) and Riha et al. (2005) that MTC is able to improve memory function in the absence of pre-existing impairment. That is, repeated treatment with MTC at the doses proposed (namely 1 mg/kg and 4 mg/kg) did not produce enhancement of learning and memory in otherwise unimpaired animals in a well validated behavioural paradigm of spatial reference memory, namely the Morris water maze.

Furthermore, it is shown in Example 2 that in certain circumstances, repeated treatment with MTC can impair learning in otherwise unimpaired animals. Therefore, it cannot be accepted that the studies enumerated provide a basis for the treatment of memory disorders on the grounds that MTC has intrinsic and universally applicable memory-improving properties.

There are further ambiguities in these earlier studies. For example, they generally do not suggest, and indeed specifically argue against the proposal, that MTC could be used to enhance learning, as the authors argue that the effects of MTC are specifically restricted to memory consolidation and not learning. However, it would be expected that the supposed memory consolidation effects must also occur in the course of learning, as the drug is administered repeatedly over a prolonged time-course in the experiments described.

Furthermore, there are contradictions as to the timing of administration required to produce supposed memory effects. Specifically, MTC apparently did not have an effect if given before training, but only after training. However it is difficult to reconcile how a drug could have utility for treatment of disorders of memory if such administration were to be restricted only to times after those for which enhanced memory is desired. This set of circumstances could only be envisaged in the context of specific training regimes, such as the extinction of conditioned fear as an adjunct to exposure therapy. There would be no expectation from the teaching enabled by the studies enumerated that MTC could be used to enhance learning and memory more generally, without reference to the timing of doses.

Thus these earlier studies do not credibly teach whether MTC, or any of the diaminophenothiazine compounds disclosed herein, are agents which could enhance learning and memory by mechanisms other than specific neurotransmitter systems, and specifically via enhancement of mitochondrial metabolism. They further do not teach whether MTC could have more general utility, other than if given at specific times with respect to training tasks, and if given at certain specific doses.

By contrast, it is shown in Example 1 that MTC is able to rectify defects of learning and memory in a model which is unrelated to mitochondrial energy metabolism. Therefore, it cannot be accepted that the effects of MTC have anything to do with the rectification of defects in mitochondrial energy metabolism. Furthermore, the potential utility of MTC is not circumscribed or restricted by the presence or absence of disorders of mitochondrial energy metabolism. Rather, MTC may be able to demonstrate positive effects on learning an memory when there are demonstrable deficits produced in any way whatsoever and irrespective of any presumption as to the underlying mechanism of the defect.

Example 4

Combination Therapy of MTC and ChEI

As noted above, the treatment of MCI via DAPTZ compounds is believed to act not through an action on the cholinergic system.

A further Experiment was performed to demonstrate the utility of DAPTZ compounds along with ChEI therapy.

The materials and methods (drugs, and behavioural apparatus and testing protocol) was generally as described in the Examples above.

The Experimental Design was as Follows:

The present study was performed in 8 replications. In these, multiple treatment groups were present and animal numbers of each group were small. For the sake of clarity, we here split the analysis into three arms:

Exp. 1 confirmed the ability and dose-response relationship of different doses of rivastigmine to reverse scopolamine-induced cognitive deficits;

Exp. 2 established whether and at what doses MTC effectively reversed cognitive deficits induced by scopolamine; and Exp. 3 tested the effects of co-administration of sub-effective doses of rivastigmine and MTC in reversing scopolamine effects.

The data from Exp. 1 and 2. is based in part on that described in Example 1 above, but is set out again and re-analysed for ease of comparison with the model used in Exp. 3.

Animals were randomly allocated to one of the treatment groups as summarised in Table 4-1. Subjects received the first i.p. injection 35 minutes prior to test; this injection consisted of either saline or scopolamine and was followed 5 minutes later by a second and/or in some groups third i.p. injections of vehicle, rivastigmine and/or MTC.

MTC was injected 5 minutes after scopolamine and 30 minutes prior to test. The timing and dose for scopolamine were chosen to enable pharmacological occupation of muscarinic ACh receptors prior to treatment reversal, based upon its pharmacokinetics.

Scopolamine has a Tmax of 20-40 minutes following i.p. administration (Kim et al., 2006; Janas et al., 2005). Initial experiments in our laboratories established peak brain levels for MTC 30-60 minutes after i.p. administration (unpublished data). MTC was injected after scopolamine with the intention of acting as a reversing agent on a pre-existent condition of cholinergic disruption. After drug administration, animals were kept in their home cage until behavioural testing.

A low dose of scopolamine (0.5 mg/kg) devoid of sensory side effects (Robinson et al., 2004) but known to induce a spatial memory deficit when injected i.p. (Steckler and Holsboer, 2001; Noda et al., 1991; Roloff et al., 2007) was used, and rivastigmine was given at 0.5 mg/kg as previously described (Bejar et al., 1999). Active doses for MTC were based on literature (Callaway et al., 2004, supra) and efficacy for reversal of tau aggregation in vitro (Wischik et al., 1996). Side-effect profiling was conducted only with highest effective and safe doses of MTC (4 mg/kg) and rivastigmine (0.125 mg/kg) in saline treated mice in order to reduce the number of animals used. Initial studies with rivastigmine at doses of 0.5 and 0.25 mg/kg, in the absence of scopolamine treatment were discontinued due to severe adverse effects in mice (motor coordination problems, ataxia, brief episodes of convulsions).

Data Analysis was as Follows:

Behavioural data of acquisition learning were analysed by conventional statistics (Graph Pad Prism version 4.01) using factorial repeated measures analysis of variance (ANOVA) with treatment as between-subject and day/trial as within-subject factor followed by planned comparisons between selected groups. Probe trial data were analysed by one-way ANOVA and the appropriate post-hoc tests (Bonferroni's multiple comparison test or Newman Keuls) were carried out to determine the source of a significant main effect or interaction. Analyses were performed two-tailed and the null hypothesis was accepted at probability levels of 5% ($p<0.05$). Only terms for reliable differences are mentioned in the text for simplicity.

Results:

Exp. 1: Rivastigmine Reverses Spatial Learning Deficits Induced by Scopolamine

Acquisition Learning

Rivastigmine was administered in a dose range of 0.1-0.5 mg/kg to establish its efficacy in reversing the scopolamine-induced cognitive impairment. In addition, the dose of 0.125 mg/kg was administered after saline to perform side-effect profiling of the drug. Analysis of the swim path length (data not shown) revealed a main effect of treatment ($F_{(6,207)}=7.408$; $p<0.0001$), an overall day effect ($F_{(3,207)}=25.6$; $p<0.001$), but no interaction ($F<1$). Performance achieved in trial one was also analysed and an overall effect of drug treatment was found ($p=0.0067$), however post hoc analysis showed that none of the treatment groups differed from controls.

This clearly supports the view that scopolamine treatment impaired learning throughout the training period, and that rivastigmine is able to reverse this deficit. Further planned comparisons of individual groups supported this impression of a dose-related reversal. Rivastigmine at doses of 0.5 and 0.125 mg/kg fully reversed the learning deficit ($F's>2.5$; $p<0.05$ compared with scopolamine, no difference with saline); by contrast 0.1 mg/kg rivastigmine was ineffective (no different from scopolamine, $F_{(3,63)}=9.6$; $p=0.003$ relative to saline).

Strangely, reversal of the 0.25 mg/kg group was only partial as the time course differed from both scopolamine ($F_{(3,60)}=5.2$; $p=0.035$) and saline ($F_{(3,63)}=4.9$; $p=0.039$). Close inspection of the individual performances, however, revealed that this was probably due to one animal in the group, which showed no learning at all. Omission of this individual confirmed full reversal of this rivastigmine dose.

Finally, rivastigmine alone did not alter spatial learning in this task. Similar results were observed for the overall learning between day 1 and 4. This is expressed as an overall reduction in path length and showed significant improvements in all groups (t values>2.3; p values<0.05) apart from the scopolamine (t=1.2) and the 0.25 mg/kg rivastigmine+scopolamine group (t=2.1; p=0.07). The same mouse identified above was again an outlier in the latter group. Interestingly, animals treated with 0.1 mg/kg rivastigmine presented with a substantial overall improvement despite a lack of reversal for the overall daily performance. This was mainly due to the poor learning on day one in this group. Swim speed was also altered as a function of drug treatment (F(6,207)=8.395; p<0.0001). Relative to control, low doses of rivastigmine (0.125 mg/kg alone or 0.1 mg/kg in conjunction with scopolamine) significantly differed from controls (F values>7; p values<0.02). By contrast to swim speed, the main effect of drug treatment for thigmotaxis (F(6,207)=4.059; p=0.0015) was primarily due to the scopolamine alone group, which differed from controls (F(3,69)=9.2; p=0.006). Although all other groups started with high proportion of wall hugging on day one, this progressive declined and was not different from controls.

Spatial Memory

Short-term memory was recorded 1.5 hours after the last training trial as time spent in the target quadrant (data not shown). A spatial bias was established for controls and scopolamine+rivastigmine 0.125 mg/kg treated mice (p values<0.5 relative to 25% chance); all other groups failed to show this preference. Comparison to controls confirmed the memory deficit in the scopolamine groups as well as scopolamine+rivastigmine 0.5 mg/kg and 0.25 mg/kg (p values<0.05; Student's t-test).

Exp. 2: MTC Reverses Scopolamine-Induced Cognitive Deficits in a Dose-Related Manner Acquisition Learning As described in Example 1 above, analysis of the swim path length revealed an overall effect of drug treatment (F(7, 240)=6.531; p<0.0001), a day effect (F(3,240)=32; p<0.0001) and an interaction (F(21,240)=1.7; p=0.03). Trial one was separately analysed and no between-group difference was found (data not shown). Planned group comparisons confirmed a learning deficit in scopolamine-treated mice relative to controls (F(3,69)=24; p<0.0001). MTC reversed this learning deficit in a dose-related manner: 4 and 1 mg/kg MTC achieved full reversal (F values>13.6; p values<0.002 compared with scopolamine alone group, not significant compared with saline); 0.5 mg/kg produced partial reversal (F(1, 60)=4.8; p=0.04 compared with scopolamine, F(1,63)=4.6; p=0.04 compared with saline); 0.25 and 0.15 mg/kg failed to reverse the scopolamine deficits (not significant with scopolamine, F values>8; p values<0.01 compared with saline).

MTC 4 mg/kg was also administered together with saline, but did not affect normal acquisition learning. Overall learning calculated as reduction of swim path over days confirmed this data.

There was no overall improvement in the scopolamine and the scopolamine+MTC 0.15 and 0.25 mg/kg groups while all other treatment groups (including scopolamine with higher doses of MTC) showed reliable learning (all t values>2.2; p values<0.05). Swim speed did not differ between groups (p>0.05). By contrast, thigmotaxis was higher in the scopolamine group but was reversed by MTC treatment independent of dose The overall factorial analysis confirmed a main effect of treatment (F(7,243)=3.9; p=0.001), a day effect (F(3,243)=60; p<0.0001), and a day by treatment interaction (F(21, 243)=2.096; p=0.0042). Only the scopolamine group was impaired relative to saline (F(1,69)=9.2; p=0.006), all other groups were not.

Spatial Memory

Spatial short-term memory was assessed by means of the probe trial 1.5 hr post training. As for acquisition learning, controls and the two high doses of MTC in conjunction with scopolamine supported memory formation and mice spent reliably more than chance in the target quadrant (t values>2.3; p values<0.05). Scopolamine alone and the lower MTC doses were not effective.

Exp. 3: Co-Administration of Sub-Effective Doses of Rivastigmine and MTC

As established in Exp. 1 and 2, rivastigmine and MTC dose-dependently reversed the cognitive impairment induced by scopolamine. Since the mechanism of action for MTC in vivo differs from rivastigmine, we reasoned that sub-effective doses of both compounds may act additively or even synergistically leading to full reversal of the deficits. Doses for rivastigmine and MTC were 0.1 mg/kg and 0.15 mg/kg respectively.

Acquisition Learning

Comparison of the four groups on the measure of path length (FIGS. 21A and B). revealed an overall effect of treatment (F(3,132)=15.52; p<0.0001), of day (F(3,132)=22; p<0.0001) and an interaction of these factors (F(9,132)=2.3; p=0.02).

The combination treatment of rivastigmine and MTC significantly improved the spatial learning deficit induced by scopolamine (F values>4, p values<0.09 for analysis with treatment as factor) and although acquisition appeared slower than in controls, this was not reliable (F values<4; p values>0.05 with treatment as factor). Similarly, rivastigmine and MTC administered in conjunction did not significantly improve controls suggesting that combination of the two drugs did not enhance normal animals. When calculated as savings (reduction in path length from day 1 to day 4; FIG. 21C), only the scopolamine alone group had not improved, while all other treatments did learn the spatial task (t values>3.4; p<0.005). While swim speed (FIG. 21D) was not affected by any drug administration, combination therapy fully reversed the scopolamine-dependent increase in thigmotaxis (FIG. 21E) (F values>4; p values<0.0031 for overall analysis with treatment as factor; F(1,69)=9.2; p=0.006 for scopolamine versus saline, all other groups not different from saline).

Spatial Memory

Rivastigmine and MTC also reversed the memory deficit induced by scopolamine (t=2.5; p=0.02 compared with scopolamine; not significant to saline), but combined administration did not alter normal spatial memory per se (FIG. 21F). All groups apart from scopolamine-treated mice presented with a spatial bias (t values>2.7; p values<0.02) confirming that reversal of the learning deficit was also transformed into short-term memory.

Discussion of Example 4

Scopolamine has been widely used in animal models to mimic muscarinic decline characteristic of ageing and dementia (Drachman and Leavitt, 1974).

As described in the Examples above, MTC provides a dose-dependent reversal of cognitive deficits of our scopolamine model. It was also effective when administered in a sub-effective dose in conjunction with a sub-effective dose of rivastigmine suggesting that it may be useful in a combination therapy. This makes MTC a cognition enhancing drug and a potential treatment for MCI. A detailed summary of the results are presented in Table 4-1.

MTC and Rivastigmine Differentially Reverse Cognitive Deficits Induced by Scopolamine in the Water Maze Task Spatial working and short-term memory is particularly sensitive to blockage of cholinergic transmission (Buxton et al., 1994; Han et al., 2000; Ballard and McAllister, 1999) leading to an inability to temporarily store information. This was readily obvious in our task in that scopolamine-treated mice showed persistently high levels of thigmotaxis possible due to an impairment of sensory filtering and enhanced anxiety (Smythe et al., 1996). Moreover, swimming away from the edge of the pool requires procedural memory and indeed striatal cholinergic activation (Blokland, 1998). This appears to be compromised in scopolamine-treated mice and particularly relevant during early stages of spatial training. We therefore suggest that both rivastigmine and MTC may act on reversal of short-term procedural memory initially to restore the animal's capacity to learn the location of the concealed platform. Non-specific motor effects induced by scopolamine were not observed, since there were no differences in swim speed, and we have previously excluded visual impairments for low doses of scopolamine (Robinson et al., 2004).

Rivastigmine at low doses readily reversed scopolamine-induced spatial short-term memory deficits (Bejar et al., 1999; this study). This effect is dose-dependent and required doses>0.125 mg/kg administered acutely to fully restore spatial learning and this is the first demonstration of such an effect in NMRI mice; chronic treatment may be efficient at lower concentrations. Our data offer the interpretation that ChEIs enhance attention (Lindner et al., 2006), reduce anxiety (van der Zee and Luiten, 1999; reduced thigmotaxis in this paper), and affect to some extent procedural learning or cognitive function, i.e. short-term memory.

Our previous work suggests that muscarinic activity is critical for all these parameters (von Linstow Roloff et al. 2007) and that they can be dissociated by means of time-consuming modifications of experimental designs. Here, we were only interested in the net effect of the drug treatment. Given that rivastigmine-induced cognitive improvement was coincident with reduced thigmotaxis indicates that anxiety, procedural learning and spatial cognition are tightly linked (Micheau et al., 2004) and may indeed all be regulated by cholinergic activity in the hippocampo-cortical system (Niewiadomska et al., 2008).

Whether normalisation of procedural learning leads to reversal of cognitive deficits, or vice versa remains unexplored. Consistent with previous reports, however, is the observation that over-stimulation of the cholinergic system by high doses of ChEIs is detrimental for memory formation in both preclinical models and humans (Bejar et al., 1999; Milivojevic et al., 2001, Beglinger et al., 2004, 2005; Van Dam et al., 2005), possibly because of hyper-stimulation of M2 muscarinic autoreceptors (Braida et al., 1996). This explains the narrow therapeutic window and possibly the short-lasting effects of ChEI treatment in dementia.

MTC

In contrast to rivastigmine, MTC presented with a different pharmacological and psychological profile and proved safe and without observable side effects even at doses of up to 4 mg/kg or higher (not shown). This offers a wider therapeutic window and may also prove safer for continuous treatment regimes. The dose-response relationship for learning and memory formation was linear with saturation at about 4 mg/kg. This may originate from different properties of MTC which include cholinesterase inhibition (Pfaffendorf et al., 1997), anti-oxidant activity, anti-tau aggregation, NOS inhibition and COX activation (Salaris et al., 1991; Martin et al., 1985; Mayer et al., 1993a, b; Volke et al., 1999; Callaway et al., 2004, supra; Wischik et al., 1996). These mechanisms fail in different forms of dementia and neurodegenerative diseases so that MTC may prove to become a novel cognitive enhancer for their treatment. Indeed, scopolamine can trigger the production of free radicals (Fan et al., 2005) and increased brain oxidative stress (El-Sherbiny et al., 2003). Consequently, several antioxidants such as acteoside (extract from *Callicarpa dichotoma*, Lee et al., 2006), acidic oligosaccharide sugar chain (Fan et al., 2005), ascorbic acid, (de Angelis and Furlan, 1995; Parle and Dhingra, 2003), and oroxylin A, (Kim et al., 2007), reversed scopolamine-induced cognitive deficits.

This Experiment therefore shows that MTC also enhances memory formation in hypo-cholinergic subjects. COX activity declines in dementia (Gonzalez-Lima et al., 1997; Kish et al., 1992; Valla et al., 2001) and in fimbria/formix transected rats with lowered cholinergic tone in hippocampus (Krügel et al., 2001). Also, COX decreases significantly after ChEI administration (Ito et al., 1989) explaining some of the pharmacological differences between MTC and rivastigmine. A corollary of enhanced COX activity is enhanced glucose metabolism i.e. ATP production.

It is thus possible that MTC is a more global cognitive enhancer owing to its universal enhancement of brain glucose and ATP generation in agreement with findings that glucose administration can enhance cognition in scopolamine models (Parsons and Gold, 1992; Micheau et al., 1995; Parkes and White, 2000).

Overall, MTC presents with a pharmacological profile that differs from the commonly prescribed ChEIs and may provide a novel approach for the treatment of cognitive impairments in neurodegenerative diseases.

Co-Administration of MTC and Rivastigmine

The combination of sub-effective doses of two or more drugs can lead to an additive or synergistic therapeutic outcome coincident with fewer adverse effects.

For the combination of rivastigmine and MTC, we observed synergistic reversal given that each constituent contributed to the final effect above its own potency. We observed full reversal of the scopolamine-induced deficit with a late onset (after day 2 of training) whereas additive effects of equivalent doses of both drugs would only result in partial reversal (rivastigmine) or no reversal (MTC). A time-related normalisation of learning, however, also occurred when rivastigmine and MTC were administered individually in cognitively effective doses and cannot be attributed to the combined drug effects. An important point to make here is that synergism of rivastigmine and MTC might arise from, their differential cellular actions. While rivastigmine at low doses may contribute to normalisation of cholinergic tone, MTC could more globally provide nutrients and energy for neurones that are activated in a task-dependent manner. If this were the case, one would expect a beneficial outcome of longer term combination therapy. MTC co-treatment may also widen the therapeutic window for rivastigmine while reducing toxicity.

TABLE 4-1

| Injection 1 | Injection 2 | Injection 2 | n | Learning | Swim speed | Thigmotaxis | S-T memory |
|---|---|---|---|---|---|---|---|
| saline | vehicle | | 13 | — | — | — | — |
| scopolamine (0.5) | vehicle | | 12 | ↓ | — | ↓ | ↓ |
| scopolamine (0.5) | MTC (4) | | 11 | ↑ | — | ↑ | ↑ |
| scopolamine (0.5) | MTC (1) | | 12 | ↑ | — | ↑ | ↑ |
| scopolamine (0.5) | MTC (0.5) | | 10 | ↑↓ | — | ↑ | ↑ |
| scopolamine (0.5) | MTC (0.25) | | 10 | ↓ | — | ↑ | ↓ |
| scopolamine (0.5) | MTC (0.15) | | 10 | ↓ | — | ↑ | ↓ |
| saline | MTC (4) | | 11 | — | — | — | — |
| scopolamine (0.5) | Rivast (0.5) | | 11 | ↑ | — | ↑ | ↓ |
| scopolamine (0.5) | Rivast (0.25) | | 10 | ↑↓ | — | ↓ | ↓ |
| scopolamine (0.5) | Rivast (0.125) | | 10 | ↑ | — | ↑ | ↑ |
| scopolamine (0.5) | Rivast (0.1) | | 10 | ↓ | ↑ | ↓ | ↓ |
| saline | Rivast (0.125) | | 10 | — | ↓ | — | ↑↓ |
| scopolamine (0.5) | MTC (0.15) | Rivast (0.1) | 14 | ↑ | — | ↑ | ↑ |
| saline | MTC (0.15) | Rivast (0.1) | 9 | — | — | — | — |

References for Example 4

2. Ballard T M, McAllister K H, (1999). The acetylcholinesterase inhibitor, ENA 713 (Exelon), attenuates the working memory impairment induced by scopolamine in an operant DNMTP task in rats. Psychopharmacology (Berl), 146(1): 10-18
4. Beglinger U, Gaydos B L, Kareken D A, Tangphao-Daniels O, Siemers E R, Mohs R C, (2004). Neuropsychological test performance in healthy volunteers before and after donepezil administration. J Psychopharmacol ar, 18(1): 102-108
5. Beglinger L J, Tangphao-Daniels O, Kareken D A, Zhang L, Mohs R, Siemers E R, (2005). Neuropsychological test performance in healthy elderly volunteers before and after donepezil administration: a randomized, controlled study. J Clin Psychopharmacol, 25(2):159-165
6. Bejar C, Wang R H, Weinstock M, (1999). Effect of rivastigmine on scopolamine-induced memory impairment in rats. Eur J Pharmacol, 383(3):231-40
9. Blokland A, (1998). Involvement of striatal cholinergic receptors in reaction time and fixed interval responding in rats. Brain Res Bull, 45:21-25
10. Braida D, Paladini E, Griffini P, Lamperti M, Maggi A, Sala M, (1996). An inverted U-shaped curve for heptylphysostigmine on radial maze performance in rats: comparison with other cholinesterase inhibitors. Eur J Pharmacol, 302: 13-20
11. Buxton A, Callan O A, Blatt E J, Wong E H, Fontana D J, (1994). Cholinergic agents and delay-dependent performance in the rat. Pharmacol Biochem Behav, 49(4):1067-1073
16. de Angelis L, Furlan C, (1995). The effects of ascorbic acid and oxiracetam on scopolamine-induced amnesia in a habituation test in aged mice. Neurobiol Learn Mem, 64(2):119-124
21. Drachman D A, Leavitt J, (1974). Human memory and the cholinergic system: a relationship to aging? Arch Neurol, 30:113-121
22. El-Sherbiny D A, Khalifa A E, Attia A S, Eldenshary Eel D, (2003). Hypericum perforatum extract demonstrates antioxidant properties against elevated rat brain oxidative status induced by amnestic dose of scopolamine. Pharmacol Biochem Behav, 76:525-533
26. Fan Y, Hu J, Li J, Yang Z, Xin X, Wang J, Ding J, Geng M, (2005). Effect of acidic oligosaccharide sugar chain on scopolamine-induced memory impairment in rats and its related mechanisms. Neu-rosci Lett, 374:222-226
28. Gonzalez-Lima F, Valla J, Matos-Collazo S, (1997). Quantitative cytochemistry of cytochrome oxidase and cellular morphometry of the human inferior colliculus in control and Alzheimer's patients. Brain Res, 752:117-126
30. Han C J, Pierre-Louis J, Scheff A, Robinson J K, (2000). A performance-dependent adjustment of the retention interval in a delayed non-matching-to-position paradigm differentiates effects of amnestic drugs in rats. Eur J Pharmacol, 403(1-2):87-93
32. Ito T, Akiyama N, Ogawa T, Satake T, Kato T, Sugiyama S, Ozawa T, (1989). Changes in myocardial mitochondrial electron transport activity in rats administered with acetylcholinesterase inhibitor. Biochem Biophys Res Commun, 164(3):997-1002
33. Janas A M, Cunningham S C, Duffy K B, Devan B D, Greig N H, Holloway H W, Yu Q S, Markowska A L, Ingram D K, Spangler E L, (2005). The cholinesterase inhibitor, phenserine, improves Morris water maze performance of scopolamine-treated rats. Life Sci, 76(10):10731081
35. Kim D H, Hung T M, Bae K H, Jung J W, Lee S, Yoon B H, Cheong J H, Ko K H, Ryu J H, (2006). Gomisin A improves scopolamine-induced memory impairment in mice. Eur J Pharmacol, 542(1-3):129-135
36. Kim D H, Jeon S J, Son K H, Jung J W, Lee S, Yoon B H, Lee J J, Cho Y W, Cheong J H, Ko K H, Ryu J H, (2007). The ameliorating effect of oroxylin A on scopolamine-induced memory impairment in mice. Neurobiol Learn Mem, 87(4):536-546
37. Kish S J, Bergeron C, Rajput A, Dozic S, Mastrogiacomo F, Chang U, Wilson J M, DiStefano L M, Nobrega J N, (1992). Brain cytochrome oxidase in Alzheimer's disease. J Neurochem, 59:776-779
39. Krügel U, Bigl V, Eschrich K, Bigl M, (2001). Deafferentation of the septo-hippocampal pathway in rats as a model of the metabolic events in Alzheimer's disease. Int J Dev Neurosci, 19(3):263-277
45. Lee J H, Park S Y, Shin Y W, Kim C D, Lee W S, Hong K W, (2007). Concurrent administration of cilostazol with donepezil effectively improves cognitive dysfunction with increased neuroprotection after chronic cerebral hypoperfusion in rats Brain Res, 1185:246-255
46. Lee K Y, Jeong E J, Lee H S, Kim Y C, (2006). Acteoside of *Callicarpa dichotoma* attenuates scopolamine-induced memory impairments. Biol Pharm Bull, 29(1):71-4
47. Lindner M D, Hogan J B, Hodges D B Jr, Orie A F, Chen P, Corsa J A, Leet J E, Gillman K W, Rose G M, Jones K M, Gribkoff V K, (2006). Donepezil primarily attenuates scopolamine-induced deficits in psychomotor function, with moderate effects on simple conditioning and attention, and small effects on working memory and spatial mapping. Psychopharmacology (Berl), 188(4):629-640
49. Martin W, Villani G M, Jothianandan D, Furchgott R F, (1985). Selective blockade of endothelium-dependent and glyceryl trinitrate-induced relaxation by hemoglobin and by methylene blue in the rabbit aorta. J Pharmacol Exp Ther, 232(3):708-716
51. Mayer B, Brunner F, Schmidt K, (1993a). Inhibition of nitric oxide synthesis by methylene blue. Biochem Pharmacol, 45(2):367-374
52. Mayer B, Brunner F, Schmidt K, (1993b). Novel actions of methylene blue. Eur Heart J, 14(1):22-26
53. Micheau J, Messier C, Jaffard R, (1995). Glucose enhancement of scopolamine-induced increase of hippocampal high-affinity choline uptake in mice: relation to plasma glucose levels. Brain Res, 685(1-2):99-104
54. Micheau J, Riedel G, Roloff E L, Inglis J, Morris R G, (2004) Reversible hippocampal inactivation partially dissociates how and where to search in the water maze. Behav Neurosci; 118(5):1022-32.
55. Milivojevic N, Babic K, Milatovic D, Dettbarn W D, Sket D, Zivin M, (2001). N-tert-butylalpha-phenylnitrone, a free radical scavenger with anticholinesterase activity does not improve the cognitive performance of scopolamine-challenged rats Int. J. Dev Neurosci, 19(3):319-325
58. Noda Y, Ochi Y, Shimada E, Oka M (1991) Involvement of central cholinergic mechanism in RU-24969-induced behavioral deficits Pharmacol Biochem Behav, 38(2):441-6
60. Parkes M, White K G, (2000). Glucose attenuation of memory impairments. Behav Neurosci, 114(2):307-319
61. Parle M, Dhingra D, (2003). Ascorbic Acid: a promising memory-enhancer in mice. J Pharmacol Sci, 93(2):129-135
62. Parsons M W, Gold P E, (1992). Scopolamine-induced deficits in spontaneous alternation performance: attenuation with lateral ventricle injections of glucose. Behav Neural Biol, 57(1):90-92
64. Pfaffendorf M, Bruning T A, Batnik H D, van Zwieten P A, (1997). The interaction between methylene blue and the cholinergic system. Br J Pharmacol, 122(1):95-98
69. Robinson L, Harbaran D, Riedel G, (2004). Visual acuity in the water maze: sensitivity to muscarinic receptor blockade in rats and mice. Behav Brain Res, 151(1-2):277-286
70. Salaris S C, Babbs C F, Voorhees W D 3$^{rd}$, (1991). Methylene blue as an inhibitor of superoxide generation by xanthine oxidase A potential new drug for the attenuation of ischemia/reperfusion injury. Biochem Pharmacol, 42(3):499-506
71. Scarpini E, Scheltens P, Feldman H, (2003). Treatment of Alzheimer's disease: current status and new perspectives. Lancet Neurol, 2:539-547
72. Small G W, Ercoli L M, Silverman D H, Huang S C, Komo S, Bookheimer S Y, Lavretsky H, Miller K, Siddarth P, Rasgon N L, Mazziotta J C, Saxena S, Wu H M, Mega M S, Cummings J L, Saunders A M, Pericak-Vance M A, Roses A D, Barrio J R, Phelps M E, (2000). Cerebral metabolic and cognitive decline in persons at genetic risk for Alzheimer's disease. Proc Natl Acad Sci, 97: 6037-6042
73. Smythe J W, Murphy D, Bhatnagar S, Timothy C, Costall B, (1996). Muscarinic antagonists are anxiogenic in rats tested in the black-white box. Pharmacol Biochem Behav, 54(1):57-63
74. Steckler T, Holsboer F, (2001). Interaction between the cholinergic system and CRH in the modulation of spatial discrimination learning in mice. Brain Res, 906(1-2):46-59
78. Valla J, Berndt J D, Gonzalez-Lima F, (2001). Energy hypometabolism in posterior cingulate cortex of Alzheimer's patients: superficial laminar cytochrome oxidase associated with disease duration. J Neurosci, 21:4923-4930
79. Van Dam D, Abramowski D, Staufenbiel M, De Deyn P P, (2005). Symptomatic effect of donepezil, rivastigmine, galantamine and memantine on cognitive deficits in the APP23 model. Psychopharmacology (Berl), 180(1):177-190
81. Van der Zee E A, Luiten P G, (1999). Muscarinic acetylcholine receptors in the hippocampus, neocortex and amygdala: A review of immunocytochemical localization in relation to learning and memory. Prog Neurobiol, 58:409-471
84. Volke V, Wegener G, Vasar E, Rosenberg R, (1999). Methylene blue inhibits hippocampal nitric oxide synthase activity in vivo. Brain Res, 826(2):303-305
85. von Linstow Roloff E, Harbaran D, Micheau J, Platt B, Riedel G, (2007). Dissociation of cholinergic function in spatial and procedural learning in rats. Neuroscience, 146, (3):875-889
86. Wischik C M, Edwards P C, Lai R Y, Roth M, Harrington C R, (1996). Selective inhibition of Alzheimer disease-like tau aggregation by phenothiazines. Proc Natl Acad Sci USA, 93(20):11213-11218

Example 5

Further Evidence of Efficacy of DAPTZ Compounds in the Treatment of Cognitive Impairment The foregoing Examples have been concerned with the ability of MTC to rapidly restore cognitive function in various models based on learning and memory in impaired mice. These included aged wild-type mice, in which no tau pathology, neurodegenerative disorder, vascular dementia, disease of impaired oxygen-consumption, or mitochondrial defect would exist.

This indicates that MTC may be useful therapeutically in the treatment of age-related cognitive decline and MCI syndromes irrespective of the mechanisms for those declines or the precise diagnosis.

This finding is corroborated by results from a phase 2, 24-week exploratory, dose-range finding, double blind, placebo controlled trial of MTC monotherapy. The study aimed at determining whether this therapy delayed cognitive decline in mild or moderate AD (using ADAS-cog change as a primary outcome measure).

However the study also employed FDG-PET (Fluoro-Deoxy Glucose Positron Emission Tomography) and $^{99}$Tc$^m$ HMPAO-SPECT (Hexamethyl-Propylene-Amine-Oxime Single Photon Emission Tomography) as a secondary outcome measure. Neuronal function (and hence cognitive performance) is known to be closely coupled with blood flow and glucose utilisation that can be measured by SPECT and PET, respectively.

These imaging methods were shown to be particularly useful in assessing the efficacy of pharmaceuticals for use in the treatment of a cognitive disorders (see U.S. provisional 60/996,177 (Wischik) filed on 5 Nov. 2007, the contents of which are specifically incorporated herein by reference).

Importantly, the study was stratified to permit analysis of the impact of baseline molecular imaging diagnosis (i.e. presence of more "AD-like" versus more vascular-like features) on therapeutic efficacy. In the study there was no evidence for a difference in treatment effect between these different underlying pathologies. Rather the suggestion was that DAPTZ therapy may be of benefit in the aging population in slowing or arresting neurofibrillary degeneration irrespective of Braak stage, risk factors and strictly defined diagnostic subtypes.

The results of the study are summarised as follows:

Molecular brain imaging was included in the trial, both as a baseline stratification variable, and as a surrogate efficacy marker. There were 138 subjects in the SPECT cohort who had images both at baseline and at visit 4 (18 weeks) as a response to treatment with MTC and 20 subjects in the PET cohort who had paired images.

When used diagnostically, SPECT and PET both reveal a characteristic bilateral temporo-parietal defect. However, the underlying biological mechanisms of action of these imaging modalities differ. SPECT reports a cerebral blood flow image obtained 'first pass' after intravenous injection. PET reports an image of glucose uptake over a period of 3 hours after injection. Both report neuronal function in different ways. SPECT depends on local blood flow over a short time-course, and so provides an indirect measure of neuronal function, since neuronal oxygen demand is closely linked to cerebral blood flow. PET measures metabolic function more directly, but integrates glucose uptake over a longer time-course.

SPECT Results

Analysis of the SPECT data showed that MTC at all doses prevents the decline in perfusion in the characteristically affected neocortical regions that can be measured objectively in untreated AD over a period of 6 months. The difference between placebo- and active-treated subjects was highly significant by both the Region of Interest ("ROI") and Statistical Parametric Mapping ("SPM") analyses. There was also a suggestion of improvement in perfusion in subjects who were CDR-mild at baseline treated with MTC at 60 mg tid, but this improvement (ie difference in change score from zero) did not reach statistical significance, although the difference with respect to placebo was highly significant in most brain regions.

PET Results

Decline in glucose uptake did not reach statistical significance in any brain region in placebo-treated subjects.

In contrast, however, in MTC-treated subjects, there was a region of significant increase in glucose uptake from the baseline image to the second PET scan at visit 4 (18 weeks) (correcting for multiple comparisons across the whole head). This increase was located in the left medial temporal lobe (hippocampus and entorhinal cortex). When the data were re-analysed, making the assumption that changes were expected only in the medial temporal lobe (ie a small volume correction for multiple comparisons), the increase in FDG uptake was significant in the MTL structures bilaterally.

Discussion

The PET data now show that treatment with MTC exerts its strongest metabolic effect in the medial temporal lobe (MTL) structures. This is expected to produce a corresponding increase in functional activity as measured by enhancement in glucose uptake. The fact that a statistically significant effect could be demonstrated with such a small number of cases indicates that the effect size is large relative to the inherent variability of the data, and leads to the expectation that the effect is robust and will be readily demonstrable in larger case series.

Further analysis is required to determine if SPECT scan perfusion changes can be also be demonstrated in MTL structures. Although SPECT scans have a lower resolution, it may be possible to determine if there are corresponding MTL blood flow changes by altering the planes in which image reconstruction and registration are undertaken. As discussed further below, the two imaging modalities may not provide the same results as they are dependent on different mechanisms of action of molecular imaging.

The relationships between regional loss of grey matter (as measured by MRI), loss of perfusion (as measured by SPECT) and loss of cognitive function in specific domains are complex. There is a strong correlation between cognitive decline and decline in cerebral blood flow, particularly for the frontal lobes and less for the temporal lobes (Brown et al., 1996). Furthermore, it is generally recognised that there is posterior to anterior spread of perfusion defects with advancing disease (Matsuda et al., 2002).

However there is not a simplistic relationship between regions of reduced perfusion and regions of loss of specific cognitive functions traditionally localised to those brain regions. Furthermore, there is not a simplistic relationship between regions of atrophy, measured by MRI, and SPECT perfusion defects. Thus, in affected areas, there is generally a greater reduction in volume than reduction in cerebral blood flow, and indeed there can be reductions in volume without any corresponding loss of cerebral blood flow (e.g. in hippocampus) in MCI/mild AD (Ibanez et al., 1998). Matsuda et al. (2002) found in a longitudinal study that there was discordance between areas of regional atrophy and areas of decreased blood flow. The explanations offered are that observed decline in blood flow in neocortex is in part explained by remote lesions (e.g. in entorhinal cortex), and secondly that in regions of primary damage, such as entorhinal cortex, loss of axons induces sprouting of the remaining nerve fibres replacing lost connections and maintaining synaptic activity, and hence blood flow.

Regardless of these potential complexities, the present discovery that MTL structures are metabolically highly responsive to MTC therapy is an important finding.

The present evidence that it is possible to demonstrate selective metabolic enhancement within the MTL structures raises the possibility of undertaking a trial to prove efficacy in MCI in which the use of PET as a surrogate end-point plays a major role.

Brown D R P, Hunter R, Wyper D J, Patterson J, Kelly R C, Montaldi D, et al. Longitudinal changes in cognitive function and regional cerebral function in Alzheimer's disease: A SPECT blood flow study. J Psychiatr Res 1996; 30: 109-26.

Matsuda H, Kitayama N, Ohnishi T, Asada T, Nakano S, Sakamoto S, et al. Longitudinal evaluation of both morphologic and functional changes in the same individuals with Alzheimer's disease. J Nuc Med 2002; 43: 304-11.

Ibanez, V., Pietrini, P., Alexander, G. E. et al. (1998) Regional glucose metabolic abnormalities are not the result of atrophy in Alzheimer's disease. Neurology 50, 1585-1593)

The invention claimed is:

1. A method for the symptomatic treatment of memory loss in a patient suffering from amnestic mild cognitive impairment (MCI) with no evidence of tau pathology, wherein the patient has a Mini-Mental State Examination Score of 25, 26, 27, 28 or 29 and is not diagnosed with Alzheimer's disease, which method comprises administering an effective amount of a diaminophenothiazine compound to said patient, wherein said compound is selected from compounds of the following formulae:

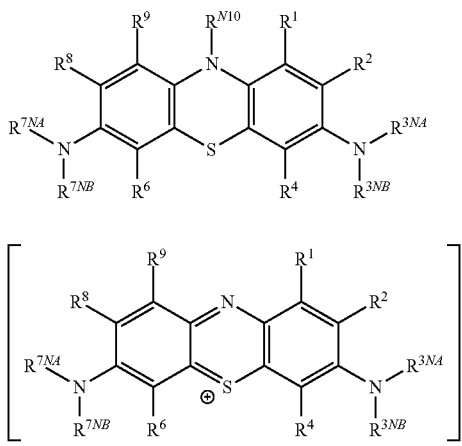

wherein each one of $R^1$, $R^2$, $R^4$, $R^6$, $R^8$, and $R^9$ is —H;

and wherein, in each group —$NR^{3NA}R^{3NA}$ each one of $R^{3NA}$ and $R^{3NB}$ is independently selected from: —H; and unsubstituted aliphatic $C_{1-6}$alkyl and wherein, in each group —$NR^{7NA}R^{7NA}$, each one of $R^{7NA}$ and $R^{7NB}$ is independently selected from: —H; and -unsubstituted aliphatic $C_{1-6}$alkyl;

and wherein $R^{N10}$, if present, is —H;

and wherein $X^-$, if present, is one or more anionic counter ions to achieve electrical neutrality, and pharmaceutically acceptable salts, mixed salts, and hydrates thereof.

2. The method of claim 1, wherein, in each group —$NR^{3NA}R^{3NB}$, each one of $R^{3NA}$ and $R^{3NB}$ is independently selected from: —H, -Me, -Et, -nPr, and -iPr.

3. The method of claim 1, wherein, in each group —$NR^{3NA}R^{3NB}$, each one of $R^{3NA}$ and $R^{3NB}$ is independently selected from: —H and -Me.

4. The method of claim 1, wherein, in each group —$NR^{7NA}R^{7NB}$, each one of $R^{7NA}$ and $R^{7NB}$ is independently selected from: —H, -Me, -Et, -nPr, and -iPr.

5. The method of claim 1, wherein, in each group —$NR^{7NA}R^{7NB}$, each one of $R^{7NA}$ and $R^{7NB}$ is independently selected from: —H and -Me.

6. The method of claim 1, wherein $R^{N10}$ is present.

7. The method of claim 1, wherein $X^-$, if present, is selected from $Cl^-$, or $Br^-$.

8. The method of claim 1, wherein the compound is selected from the group consisting of any of the following compounds A, B, G, H, M, N, P and Q, and pharmaceutically acceptable salts, mixed salts, and hydrates thereof:

A MTC
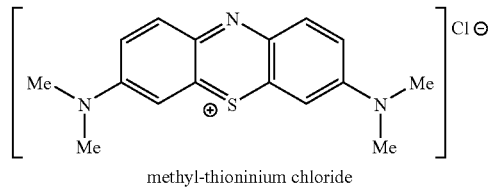
methyl-thioninium chloride

B ETC
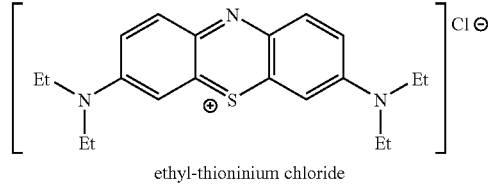
ethyl-thioninium chloride

G MTZ
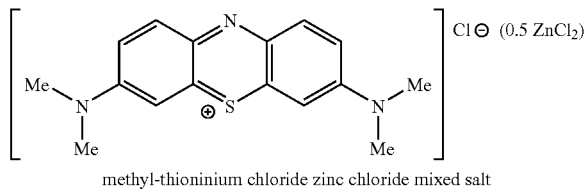
methyl-thioninium chloride zinc chloride mixed salt

H ETZ
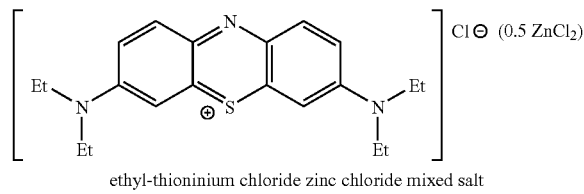
ethyl-thioninium chloride zinc chloride mixed salt

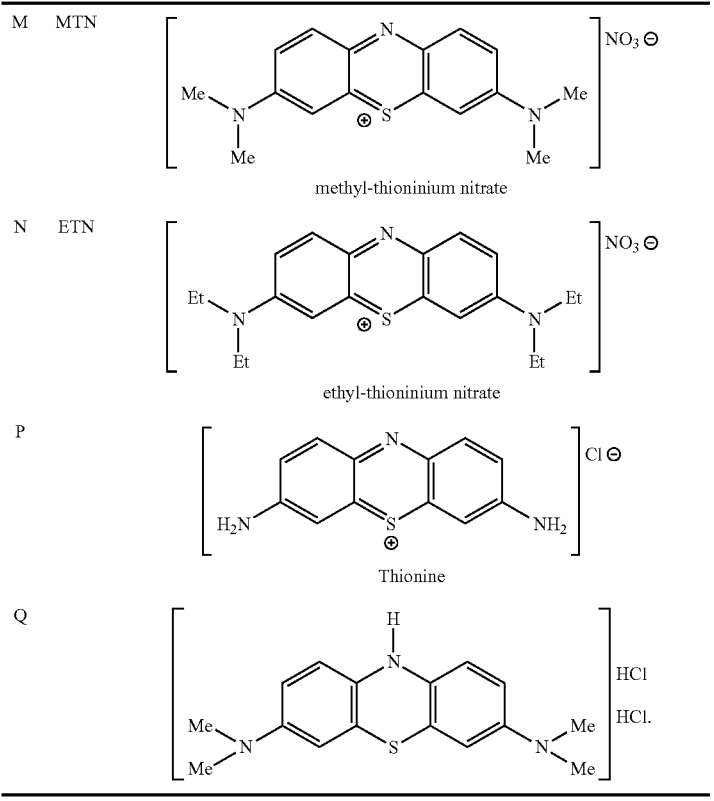

9. The method of claim 8, wherein the compound is

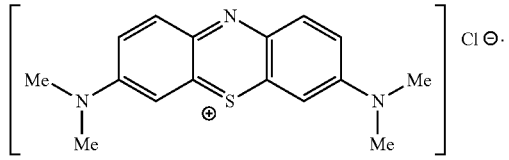

10. The method of claim 8, wherein the compound is

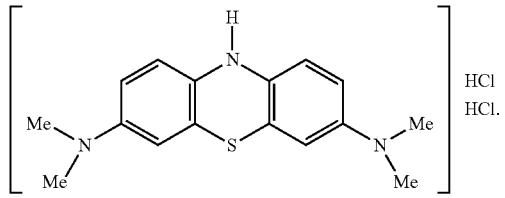

11. The method of claim 1 wherein said treatment comprises administering said diaminophenothizine compound in combination with a cholinergic drug that enhances or mimics the action of acetylcholine.

12. The method of claim 1 wherein said patient does not suffer from a defect in mitochondrial energy metabolism.

13. The method of claim 1 wherein less than or equal to 400, 300, 200, 100, 50, 40, 30, 20, 15, or 10 mg daily total dose is administered.

14. The method of claim 1 wherein less than 50% of the total amount of diaminophenothiazine compound in the medicament is either a compound of formula (I) or a pharmaceutically acceptable salt, mixed salt, or hydrate thereof.

* * * * *